United States Patent
Dhodapkar et al.

(10) Patent No.: US 11,213,546 B2
(45) Date of Patent: Jan. 4, 2022

(54) METHODS TO MOBILIZE TISSUE RESIDENT CELLS FOR ADOPTIVE T CELL THERAPY

(71) Applicant: Emory University, Atlanta, GA (US)

(72) Inventors: Madhav Dhodapkar, New Haven, CT (US); Venkata Naga Chandrasekhar Boddupalli, New Haven, CT (US)

(73) Assignee: Emory University, Atlanta, GA (US)

( * ) Notice: Subject to any disclaimer, the term of this patent is extended or adjusted under 35 U.S.C. 154(b) by 322 days.

(21) Appl. No.: 16/123,261

(22) Filed: Sep. 6, 2018

(65) Prior Publication Data

US 2019/0070221 A1    Mar. 7, 2019

Related U.S. Application Data

(60) Provisional application No. 62/555,124, filed on Sep. 7, 2017.

(51) Int. Cl.
| | |
|---|---|
| *A61K 35/17* | (2015.01) |
| *C12N 5/0783* | (2010.01) |
| *A61K 38/19* | (2006.01) |
| *A61P 35/00* | (2006.01) |
| *A61K 31/395* | (2006.01) |
| *A61P 37/04* | (2006.01) |
| *C07D 257/02* | (2006.01) |
| *C07D 403/10* | (2006.01) |

(52) U.S. Cl.
CPC ............ *A61K 35/17* (2013.01); *A61K 31/395* (2013.01); *A61K 38/193* (2013.01); *A61P 35/00* (2018.01); *A61P 37/04* (2018.01); *C07D 257/02* (2013.01); *C07D 403/10* (2013.01); *C12N 5/0636* (2013.01); *C12N 2501/22* (2013.01)

(58) Field of Classification Search
None
See application file for complete search history.

(56) References Cited

U.S. PATENT DOCUMENTS

| | | |
|---|---|---|
| 6,908,763 B1 | 6/2005 | Akashi |
| 2006/0263341 A1 | 11/2006 | Freyman |
| 2012/0003189 A1 | 1/2012 | Pelus |

FOREIGN PATENT DOCUMENTS

WO    2016120310    8/2016

OTHER PUBLICATIONS

Allam et al. The CD8 memory T-cell state of readiness is actively maintained and reversible, Blood. 2009, 114:2121-2130.
Boddupalli et al. ABC transporters and NR4A1 identify a quiescent subset of tissue-resident memory T cells, J Clin Invest. 2016, 126(10):3905-3916.
Fearon et al. Arrested Differentiation, the Self-Renewing Memory Lymphocyte, and Vaccination, Science, 2001, 293(5528):248-5.
Foundi et al. Defining Hematopoietic Stem and Progenitor Cell Turnover by Analysis of Histone 2B-GFP Dilution, Nat Biotechnol. 2009, 27(1): 84-90.
Galy et al. Human T, B, Natural Killer, and Dendritic Cells Arise from a Common Bone Marrow Progenitor Cell Subset Immunity, vol. 3, 459-473, 1995.
Land et al. The orphan nuclear receptor NR4A1 specifies a distinct subpopulation of quiescent myeloid-biased long-term HSCs, Stem Cells. 2015, 33(1): 278-288.
Li et al. Transcriptional Analysis of T Cells Resident in Human Skin, PLoS ONE, 2016, 11(1): e0148351.
Liu et al. p53 Regulates Hematopoietic Stem Cell Quiescence, Cell Stem Cell. 2009, 4(1): 37-48.
Luckey et al. Memory T and memory B cells share a transcriptional program of self-renewal with long-term hematopoietic stem cells, Proc Natl Acad Sci U S A. 2006, 103(9): 3304-3309.
Mackay et al. The developmental pathway for CD103+CD8+ tissue-resident memory T cells of skin, Nat Immunol, 2013, 14(12):1294-301.
Nakamura et al. The analysis, roles and regulation of quiescence in hematopoietic stem cells, Development (2014) 141, 4656-4666.
Rettig et al. Mobilization of Hematopoietic Stem and Progenitor Cells Using Inhibitors of CXCR4 and VLA-4, Leukemia. 2012, 26(1): 34-53.
Schenkel et al. Tissue-Resident Memory T Cells, Immunity. 2014, 41(6): 886-897.
Sekiya et al. Nr4a receptors are essential for thymic regulatory T cell development and immune homeostasis, Nat Immunol, 2013, 14(3):230-7.
Sirin et al. The Orphan Nuclear Receptor Nurr1 Restricts the Proliferation of Hematopoietic Stem Cells, Nat Cell Biol. 2010, 12(12): 1213-1219.
Tarling et al. Role of ABC transporters in lipid transport and human disease, Trends Endocrinol Metab. 2013, 24(7): 342-350.
Thome et al. Spatial map of human T cell compartmentalization and maintenance over decades of life, Cell. 2014, 159(4): 814-828.
Veiga et al. High expression of active CDK6 in the cytoplasm of CD8 memory cells favors rapid division, Nat Immunol 2004, 5(1):31-7.

(Continued)

*Primary Examiner* — Daniel C Gamett
(74) *Attorney, Agent, or Firm* — Emory Patent Group

(57) ABSTRACT

The present disclosure includes compositions, methods, and uses for a subset of T cells, SP T ($T_{SP}$) cells, which display a quiescent (G0) phenotype. Aspects of the disclosure include methods for obtaining and mobilizing $T_{SP}$ cells in a subject. Other aspects include methods of adoptive cell transfer in a subject utilizing $T_{SP}$ cells.

9 Claims, 39 Drawing Sheets

(56) References Cited

OTHER PUBLICATIONS

Watanabe et al. Human skin is protected by four functionally and phenotypically discrete populations of resident and recirculating memory T cells, Sci Transl Med, 2015, 7(279):279ra39.

Wilson et al. Hematopoietic Stem Cells Reversibly Switch from Dormancy to Self-Renewal during Homeostasis and Repair, Cell, 2008, 135(6):1118-29.

1. Primary metabolic process
2. Cellular metabolic process
3. Macromolecule metabolic process
4. Metabolic process
5. Apoptotic process
6. Nucleobase-containing compound metabolic process
7. Programmed cell death
8. Cell Cycle
9. Nitrogen compound metabolic process
10. Positive regulation of biological process

METHODS TO MOBILIZE TISSUE RESIDENT CELLS FOR ADOPTIVE T CELL THERAPY

CROSS-REFERENCE TO RELATED APPLICATIONS

This application claims the benefit of U.S. Provisional Application No. 62/555,124 filed Sep. 7, 2017. The entirety of this application is hereby incorporated by reference for all purposes.

STATEMENT REGARDING FEDERALLY SPONSORED RESEARCH OR DEVELOPMENT

This invention was made with government support under CA106802 and CA197603 awarded by the National Institutes of Health. The government has certain rights in the invention.

BACKGROUND

A fundamental property of human T cells is to provide lifelong immunity against pathogens lasting several decades. The complement of T cells within an individual is heterogeneous and includes naïve T cells that develop from thymic precursors, short lived effector cells, and memory T cells derived from naïve T cells following antigen exposure. Maintenance of each of these components for several decades of life is essential to host defense: memory T cells for defense against previously encountered antigens, and naïve T cells for responses to new antigens. T cell memory is mediated by coordinated action of distinct subsets. Initial pioneering studies classified human memory T cells into effector memory ($T_{EM}$) and central memory ($T_{CM}$) T cells based on rapid effector function and the expression of lymphoid homing receptors respectively. More recent studies have identified and characterized a subset of memory T cells resident in non-lymphoid tissues (NLT) that mediate regional immune surveillance against pathogens, tissue-resident memory ($T_{RM}$) T cells. $T_{RM}$ cells in NLTs outnumber memory CD8 T cells in lymphoid tissues and represent the primary steady-state surveillance mechanism in non-lymphoid tissues. Both $T_{CM}$ and $T_{RM}$ cells originate from a common clonal precursor, but following tissue localization, $T_{RM}$ cells maintain a highly regional network and persist over decades of life with apparently little homeostatic turnover. Little is known about the mechanisms that underlie the development, dormancy and maintenance of these long-lived $T_{RM}$ cells, particularly in humans, and investigation of these areas will have major implications for understanding immune homeostasis within tissues.

Homeostasis in adult tissues is maintained by the differentiation of a small population of adult stem cells. The capacity of T cells for long-term survival, quiescence, clonal differentiation and self-renewal has elicited comparisons between long-lived post-mitotic cells such as memory T cells and adult stem cells. Indeed, prior studies have shown that murine memory T cells share a transcriptional program of self-renewal with long-term hematopoietic stem cells. The ability to efflux lipophilic Hoechst dyes is a distinct property of a subset of hematopoietic stem cells, termed as side population (SP) cells with enhanced regenerative potential. The SP phenotype (i.e., dye efflux) is mediated by the expression of ATP-binding cassette (ABC) transporters (particularly ABCG2 in most HSCs and some adult stem cells) and cells with the SP phenotype have been identified in putative stem cells in diverse tissues. ABC transporters efflux diverse substrates and their expression in stem cells are postulated to protect these cells from xenotoxic, oxidative and metabolic stress. Human $CD8^+$ memory T cells expressing P-glycoprotein/ABCB1 were shown to persist following cancer chemotherapy; however, most human T cells with $ABCB1^+$ phenotype were later shown to be mucosa-associated invariant T (MAIT) cells.

Adoptive transfer of genetically modified T cells, either with chimeric antigen receptors (CAR) or anti-tumor T cell receptors is emerging as a promising therapeutic approach in hematologic malignancies. However, most of the clinical success with CAR T cells to date is limited to patients with leukemia. A need exists for compositions and methods that mobilize T cells and enhance their persistence and ability to infiltrate non-lymphoid tissues, in order to be able to target solid tumors.

SUMMARY OF THE INVENTION

As described herein, the present invention relates to compositions and methods comprising a novel subtype of tissue-resident memory ($T_{RM}$) T cells that display a quiescent (G0) phenotype: side population T ($T_{SP}$) cells.

One aspect of the invention includes a $T_{SP}$ cell in a non-naturally occurring container, wherein the $T_{SP}$ cell displays a quiescent (G0) phenotype.

Another aspect of the invention includes a method of obtaining a $T_{SP}$ cell from a subject. The method comprises administering to the subject a CXCR4 antagonist. The CXCR4 antagonist induces mobilization of the $T_{SP}$ cell from the subject's tissue or bone marrow into the subject's circulation. The $T_{SP}$ cell so mobilized from the subject's circulation is isolated.

Yet another aspect of the invention includes a method of adoptive T cell transfer in a subject. The method comprises administering to the subject a CXCR4 antagonist, wherein the CXCR4 antagonist induces mobilization of the $T_{SP}$ cell from the subject's tissue or bone marrow into the subject's circulation. The $T_{SP}$ cell so mobilized from the subject's circulation is isolated and modified ex vivo. The modified $T_{SP}$ cell is administered to the subject.

Still another aspect of the invention includes a method of adoptive T cell transfer in a subject. The method comprises isolating a $T_{SP}$ cell from a subject. The $T_{SP}$ cell displays a quiescent (G0) phenotype, and expresses at least one ABC transporter and at least one transcription factor from the NR4A family. The isolated $T_{SP}$ cell is modified ex vivo. The modified $T_{SP}$ cell is administered to the subject.

In various embodiments of the above aspects or any other aspect of the invention delineated herein, the $T_{SP}$ cell expresses at least one ATP binding cassette (ABC) transporter and at least one transcription factor from the nuclear receptor subfamily 4 (NR4A) family. In one embodiment, the at least one transcription factor is selected from the group consisting of: NR4A1(Nur77), NR4A2, and NR4A3. In one embodiment, the at least one transcription factor comprises NR4A1(Nur77).

In one embodiment, the $T_{SP}$ cell expresses at least one gene selected from the group consisting of: XCL1, PTGER4, PPP1R15A, GLA, NFKB1D, DUSP6, RASD1, SKIL, TNFSF9, TNF, SIK1, HSPA1A, NR4A3, GADD45B, PHLDA1, GEM, NR4A2, FOSB, EGR1, NR4A1, and ATF3.

In one embodiment, the $T_{SP}$ cell is $CD8^+$. In one embodiment, the $T_{SP}$ cell is $CD4^+$.

In one embodiment, the CXCR4 antagonist comprises plerixafor.

In one embodiment, the method further comprises administering granulocyte-colony stimulating factor (G-CSF) to the subject. In one embodiment, the method further comprises expanding the isolated $T_{SP}$ cell ex vivo.

In one embodiment, the $T_{SP}$ cell is isolated from the subject's gut, liver, skin or bone marrow.

BRIEF DESCRIPTION OF THE DRAWINGS

The following detailed description of exemplary embodiments will be better understood when read in conjunction with the appended drawings. It should be understood, however, that the disclosure is not limited to the precise arrangements and instrumentalities of the embodiments shown in the drawings.

FIG. 1A shows FACS analysis of Hoechst dye effluxing $T_{SP}$ cells from human blood, bone marrow, IEL and skin (right panel), and with SP inhibitor verapamil (left panel).

FIG. 1B is a bar graph that represents the frequency of $T_{SP}$ cells from blood, BM, IEL and skin.

FIG. 1C represents CD4$^+$/CD8$^+$ subsets in $T_{SP}$ cells from blood, BM, IEL and skin, (blood n=20, BM n=7, IEL n=6 and skin n=4).

FIG. 1D is a pie diagram that represents Vβ repertoire in CD8 $T_{SP}$ and MAIT CD8$^+$ T cells.

FIG. 1E shows FACS analysis documenting Human Flu-matrix peptide HLA A*0201-Tetramer$^+$ cells (left) and SP fraction on Flu Tet$^+$CD8 T cells.

FIG. 1F shows a representative FACS plot gated on CD8 $T_{SP}$ and NSP cells from IEL (representative of 6 independent experiments), and the same plotted in a bar graph.

FIG. 1G shows FACS analysis on CD8 $T_{SP}$ and NSP cells from skin. The bar graph represents compiled data from 4 independent skin samples.

FIG. 1H shows FACS analysis on blood $T_{SP}$, NSP cells that are gated on CD45RO$^+$CD62L$^-$ CCR7$^-$ CD8$^+$ T cells. The bar graph represents the compiled data (n=6). *P<0.05; ***P<0.001.

FIG. 2A shows representative CD8 $T_{SP}$ analysis on LCMV-arm infected mice. Results from spleen and IEL at day 8 (left) and day 30 (right) are shown.

FIG. 2B is a graph representing the same data as FIG. 2A (n=4 mice). Experiment was repeated twice and FIG. 2B represents one of the experiments.

FIG. 2C, top panels show the percentage of CD8 $T_{SP}$ and NSP gp33$^+$CD8$^+$ T cells at day 35 post-infection in different organs. FIG. 2C, bottom panel shows results gated on gp33$^+$CD8$^+$ TSP cells.

FIG. 2D shows the percent of gp33$^+$ $T_{RM}$ cells in CD8 $T_{SP}$ and NSP fractions. Bar graphs represent data from 7-10 mice. Data compiled from 3 independent experiments. *P<0.05; P<0.01; *P<0.001.

FIG. 3A shows Hoechst-PY cell cycle analysis on $T_{SP}$ and NSP fractions from human blood CD8 T cells (top panel), and IEL and skin CD8 $T_{RM}$ cells (middle and bottom panel). Results depicted are representative of 3 independent experiments.

FIG. 3B is a graph representing combined data of 3 independent experiments.

FIG. 3C is a bar graph displaying percent of G0 and G1 fractions in CD8$^+$ $T_{SP}$ and NSP gated on $T_{RM}$ compartment from PP, IEL in mice at day 35 (p.i) with LCMV-arm.

FIG. 3D is a schematic diagram showing the protocol for measuring GFP label retention in H2B-GFP mice upon LCMV-arm infection.

FIG. 3E shows data on FACS analysis on memory CD8 T cells from BM, Spleen, Liver, IEL and PP after 5 weeks of chase as shown in the bar graph (n=4-5 mice).

FIG. 3F shows FACS analysis of GFP label retention in SP and NSP CD8$^+$ $T_{RM}$ compartment at 5 weeks chase in H2B GFP mice infected with LCMV-arm.

FIG. 3G shows the percentages of GFP$^+$ cells in SP and NSP CD8$^+$ $T_{RM}$ cells. *P<0.05. Mice experiments were repeated twice, graphs represent analysis from one experiment (n=4 mice).

FIG. 4A is a PCA plot comparing CD8 naïve, CD8 effector memory (EM), CD8 central memory (CM) and CD8 $T_{SP}$.

FIG. 4B is a Venn diagram of differentially regulated transcripts (>4 fold) in CD8 $T_{SP}$ compared to naïve, EM and CM CD8 T cells.

FIG. 4C shows the top 10 GO (Gene Ontology) terms from Metacore pathway analysis of genes enriched in CD8 $T_{SP}$ cells.

FIG. 4D shows the relative expression of human skin $T_{RM}$ genes in blood CD8 $T_{SP}$ cells compared to nave, EM and CM CD8 T cells.

FIG. 5A is a series of FACS analysis plots showing CD45.2 (Nur77$^{-/-}$ OT-1) and CD45.1 (WT OT-1) cells in spleen, BM, liver, lung, PP and IEL.

FIG. 5B shows a series of bar graphs showing the absolute number of Nur77$^{-/-}$ OT-1 and WT OT-1 CD8$^+$ T cells from different organs. Experiments were repeated twice with 3-4 mice each; graphs represent data from one independent experiment (n=4 mice). *P<0.05.

FIG. 6A is a bar graph comparing WT and ABCG2$^{-/-}$ ABCB1 a/b$^{-/-}$ mice gut (PP, IEL and LPL) $T_{RM}$ compartments that are CD4$^+$, CD4$^+$CD8$^+$ and CD8$^+$.

FIG. 6B shows intracellular cytokine flow cytometry documenting IFN-γ production upon PMA+ionomycin activation of WT and ABCG2$^{-/-}$ ABCB1 a/b$^{-/-}$ mice IELs.

FIG. 6C is a bar graph showing IFN-γ production in different T cell populations from WT and ABCG2$^{-/-}$ ABCB1 a/b$^{-/-}$ mice. Experiments are repeated twice with 3 to 4 mice each; graphs represent data from one experiment (n=4 mice). *P<0.05; P<0.01; *P<0.001.

FIG. 7A is a FACS plot showing engraftment of human CD45 T cells, and the same is plotted in the bar graph.

FIG. 7B is a set of pictures comparing skin pathology, liver and skin histopathology in NSG mice receiving $T_{SP}$ and control T cells.

FIG. 7C shows GVHD scores for liver and skin. Experiments were repeated 3 times with 4 mice/group.

FIG. 7D is a series of FACS plots showing $T_{SP}$ phenotype on pre- and post-mobilized $CD8^+$ T cells and $CD34^+$ cells from human peripheral blood.

FIG. 7E shows the percent of $T_{SP}$ fractions in $CD8^+$ and $CD34^+$ cells at baseline and after mobilization (n=6). *P<0.05.

FIG. 8A shows proportions of $CD45RA^+$ and $CD45R0^+$ cells in $T_{SP}$ and NSP fractions of CD4 or CD8 T cells in human blood.

FIG. 8B shows proportions of $CD45RA^+$ and $CD45R0^+$ cells in $T_{SP}$ and NSP fractions of CD4 or CD8 T cells in bone marrow. Graphs represent compiled data from 4 to 5 human blood and BM samples.

FIG. 8C shows FACS analysis on skin CD8 $T_{SP}$ and NSP cells. The bar graph shows enrichment of effector memory phenotype ($CD45RO^+CCR7^- CD62L^-$) in CD8 $T_{SP}$ and NSP fractions; compiled data is shown (n=5).

FIG. 8D shows representative flow analysis on IEL CD8 $T_{SP}$ and NSP cells for effector phenotype. Experiments were repeated for 3-4 independent human IEL samples.

FIG. 9A is a bar graph showing kinetics of P14 CD8 $T_{SP}$ at days 5, 8, 15, 30 and 60 (p.i) in LN, spleen and BM of infected mice.

FIG. 9B shows FACS analysis detecting $P14^+ CD8^+ T_{SP}$ in different organs at day 30 (p.i) (bottom panel), and complete absence of P14 CD8 $T_{SP}$ when treated with inhibitor (top panel).

FIG. 9C shows SP analysis on $P14^+ CD8^+ T_{RM}$ and non $T_{RM}$ cells from liver, PP, IEL and LPL. Experiment was performed with n=3 mice for each group.

FIG. 9D shows detection of SP phenotype on human IEL CD8 $T_{RM}$ cells. Experiment repeated 6 times, representative FACS analysis is shown.

FIG. 10A is a FACS plot showing GFP label on blood CD8 T cells before chase, and the same is documented in the bar graph.

FIG. 10B shows GFP label retention in the bone marrow $c$-$Kit^+$ cells (left plot) and spleen nave $CD44^- CD62L^+$ cells (right plot).

FIG. 10C shows SP analysis of CD8 T cells from blood, liver, PP and IEL. Experiments were repeated twice with n=4, data presented here is from one of the two experiments.

FIG. 12A is a bar graph showing $V\alpha2 CD8^+$ T cell chimerism in blood at day 8 after Flu ova infection.

FIG. 12B documents $V\alpha2 CD8^+$ T cell chimerism in spleen at day 14 post infection. Experiment was repeated twice with n=3 mice for each group, compiled data from two experiments is shown.

FIG. 13A shows FACS plots comparing CD4 and CD8 frequency in WT and $ABCG2^{-/-} ABCB1a/b^{-/-}$ mice.

FIG. 13B shows a bar graph comparing CD4 and CD8 frequency in WT and $ABCG2^{-/-} ABCB1a/b^{-/-}$ mice.

FIG. 13C shows FACS plots of WT IEL CD4 and CD8 $T_{RM}$ cells with SP phenotype that is completely absent in IELs from $ABCG2^{-/-} ABCB1a/b^{-/-}$ mice.

FIG. 13D is a representative FACS analysis and a bar graph documenting the percent of SP cells in $CD8^+CD69^+ CD62L^-$ liver cells from WT and $ABCG2^{-/-} ABCB1a/b^{-/-}$ mice.

FIG. 13E shows IFN-γ production from blood and spleen $CD4^+$, $CD8^+$ T cells compared between WT and $ABCG2^{-/-} ABCB1a/b^{-/-}$ mice. Experiments were repeated twice with 3 to 4 mice each, graphs represent data from one experiment (n=4 mice).

FIG. 14A is a FACS plot showing the percent of $Thy1.1^+$ CD8 T cells in IEL $CD69^+ CD103^+ T_{RM}$ cells. A summary of the data is presented in the bar graph (n=5).

FIG. 14B shows FACS analysis of the percent $Thy1.1^+$ CD8 T cells in splenic $T_{EM}$ and $T_{CM}$ compartments. Combined analysis is shown in the bar graph (n=5).

DETAILED DESCRIPTION

Figure 1A:
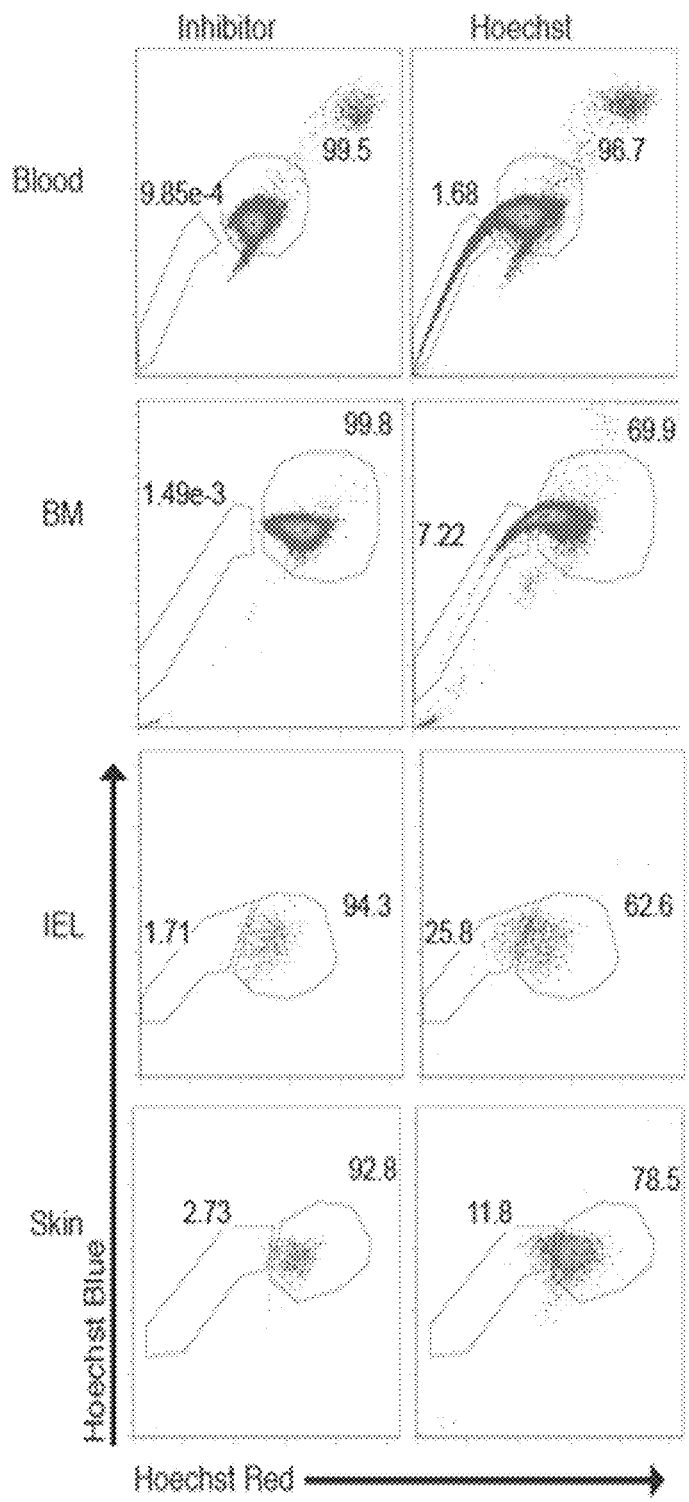
FIGS. 1A-1H are a series of graphs showing enrichment of $T_{SP}$ cells in human tissues with $T_{RM}$ phenotype.

Immune surveillance in tissues is mediated by a long-lived subset of tissue-resident memory T cells ($T_{RM}$ cells). A putative subset of tissue-resident long-lived stem cells is characterized by the ability to efflux Hoechst dyes and is referred to as side population (SP) cells. In the present disclosure, a subset of SP T cells ($T_{SP}$ cells) that exhibit a quiescent (G0) phenotype in humans and mice has been identified and characterized. Human $T_{RM}$ cells in the gut and bone marrow have been found to be enriched in $T_{SP}$ cells that were predominantly in the G0 stage of the cell cycle. Moreover, in histone 2B-GFP mice, the 2B-GFP label was found to be retained in $T_{SP}$ cells, indicating a slow-cycling phenotype. Moreover, human $T_{SP}$ cells displayed a distinct gene expression profile that was enriched for genes overexpressed in $T_{RM}$ cells. In mice, proteins encoded by $T_{SP}$ signature genes, including nuclear receptor subfamily 4 group A member 1 (NR4A1) and ATP binding cassette (ABC) transporters, influenced the function and differentiation of $T_{RM}$ cells. Responses to adoptive transfer of human $T_{SP}$ cells into immune-deficient mice and plerixafor therapy demonstrated that human $T_{SP}$ cell mobilization could be manipulated as a cellular therapy. The disclosure therefore includes a distinct subset of human T cells that display a quiescent/slow-cycling phenotype, propensity for tissue enrichment, and potential to mobilize into circulation, which may be harnessed for use in adoptive cellular therapy.

Definitions

Unless defined otherwise, all technical and scientific terms used herein have the same meaning as commonly understood by one of ordinary skill in the art to which the disclosure pertains. Although any methods and materials similar or equivalent to those described herein can be used in the practice for testing of the present disclosure, the preferred materials and methods are described herein. In describing and claiming the present disclosure, the following terminology will be used.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present disclosure includes, but is not limited to, the use of partial nucleotide sequences of more than one gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

As used herein, the term "autologous" is meant to refer to any material derived from the same individual to which it is later to be re-introduced into the individual.

"Allogeneic" refers to any material derived from a different animal of the same species.

"Xenogeneic" refers to any material derived from an animal of a different species.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

The term "downregulation" as used herein refers to the decrease or elimination of gene expression of one or more genes.

"Effective amount" or "therapeutically effective amount" are used interchangeably herein, and refer to an amount of a compound, formulation, material, or composition, as described herein effective to achieve a particular biological result or provides a therapeutic or prophylactic benefit. Such results may include, but are not limited to, anti-tumor activity as determined by any means suitable in the art.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expand" as used herein refers to increasing in number, as in an increase in the number of T cells. In one embodiment, the T cells that are expanded ex vivo increase in number relative to the number originally present in the culture. In another embodiment, the T cells that are expanded ex vivo increase in number relative to other cell types in the culture. The term "ex vivo," as used herein, refers to cells that have been removed from a living organism, (e.g., a human) and propagated outside the organism (e.g., in a culture dish, test tube, or bioreactor).

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., Sendai viruses, lentiviruses, retroviruses, adenoviruses, and adeno-associated viruses) that incorporate the recombinant polynucleotide.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

The term "immune response" as used herein is defined as a cellular response to an antigen that occurs when lymphocytes identify antigenic molecules as foreign and induce the formation of antibodies and/or activate lymphocytes to remove the antigen.

When "an immunologically effective amount," "an autoimmune disease-inhibiting effective amount," or "therapeutic amount" is indicated, the precise amount of the compositions of the present disclosure to be administered can be determined by a physician or researcher with consideration of individual differences in age, weight, tumor size, extent of infection or metastasis, and condition of the patient (subject).

As used herein, an "instructional material" includes a publication, a recording, a diagram, or any other medium of expression which can be used to communicate the usefulness of the compositions and methods of the disclosure. The instructional material of the kit of the disclosure may, for example, be affixed to a container which contains the nucleic acid, peptide, and/or composition of the disclosure or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide or a cell naturally present in a living animal is not "isolated," but the same nucleic acid or peptide or cell partially or completely separated from the coexisting materials of its natural state is "isolated." An isolated nucleic acid or protein can exist in substantially purified form, or can exist in a non-native environment such as, for example, a host cell. In another non-limiting example, a $T_{SP}$ cell removed from a subject is "isolated".

The term "limited toxicity" as used herein, refers to the peptides, polynucleotides, cells and/or antibodies of the disclosure manifesting a lack of substantially negative biological effects, anti-tumor effects, or substantially negative physiological symptoms toward a healthy cell, non-tumor cell, non-diseased cell, non-target cell or population of such cells either in vitro or in vivo.

By the term "modified" or "modifying" as used herein, is meant a changed state or structure of a molecule or cell of the disclosure. Molecules may be modified in many ways, including chemically, structurally, and functionally. Cells may be modified through the introduction of nucleic acids. For example, a $T_{SP}$ cell can be modified to contain a chimeric antigen receptor (CAR).

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

As used herein, "quiescent (G0) phenotype" refers to a resting/slow-cycling state the cell cycle wherein a cell is not dividing or preparing to divide.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-beta, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an APC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an WIC Class I molecule loaded with a peptide, an anti-CD3 antibody, a superagonist anti-CD28 antibody, and a superagonist anti-CD2 antibody.

The term "subject" is intended to include living organisms in which an immune response can be elicited (e.g., mammals). A "subject" or "patient," as used therein, may be a human or non-human mammal. Non-human mammals include, for example, livestock and pets, such as ovine, bovine, porcine, canine, feline and murine mammals. Preferably, the subject is human.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

When whole blood is centrifuged, cells are separated in density layers. Plasma will be on the top. Red blood cells on the bottom. A buffy coat, which contains platelets and white blood cells, sits in between the plasma and red blood cells. The white blood cells contain T cells. The process may be automated using an apheresis machine. Inside an apheresis machine, there is a blood chamber that centrifuges the blood, separating it into layers. Red cells are heaviest and sit at the bottom, platelets and white cells are in the middle (buffy coat), plasma is at the top as it is the lightest.

One can positively isolate T cells from whole blood, buffy coat, mononuclear cells or bone marrow by using antibodies that bind T cells markers bound to magnetic material. One can remove the beads using a magnet, and use an agent to release the T cells from the beads. One can also isolate purified T cells, e.g., directly from human whole blood, by immunomagnetic negative selection. Non-T cells can be targeted for removal with antibodies conjugated to magnetic material recognizing specific surface markers. Unwanted cells are labelled with antibodies and may be separated using a magnet.

This disclosure contemplates methods of isolating side population T cells comprising, obtaining human T cells from a sample, e.g., bone marrow or peripheral blood, mixing the T cells with Hoechst dye under conditions such that the Hoechst dye enters the T cells and isolating cells that efflux the Hoechst dye from the T cells. This disclosure contemplates methods disclosed herein, wherein T cells are obtained by positive or negative selection of T cells with T cell markers or non T cell markers. This disclosure contemplates methods disclosed herein, wherein the T cell markers are CD3, CD4, CD8, or combinations thereof.

As used herein a "Hoechst dye" refers to a dye with a 5-(4-methylpiperazin-1-yl)-2'-phenyl-1H,1'H-2,5'-bibenzo[d]imidazole core structure or salt thereof. This disclosure contemplates methods disclosed herein, wherein the Hoechst dye contains one or more compounds having of the following formula

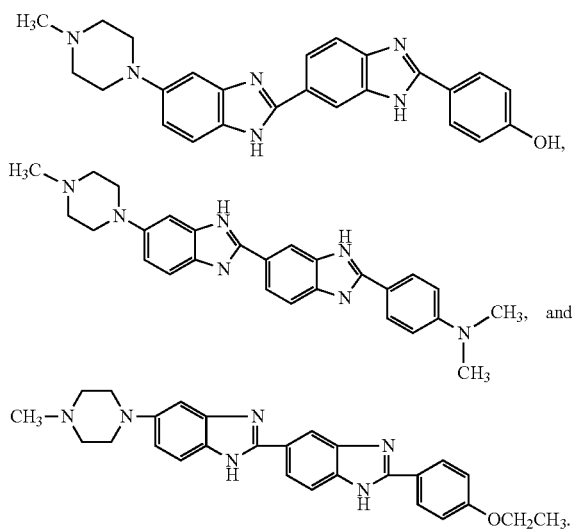

(also called Hoechst 33342).

Hoechst 33342 is a bis-benzimide derivative that binds to AT-rich sequences in the minor grove of double-stranded DNA. Hoechst 33342 is detected at two emission wavelengths after UV excitation: Hoechst Red (630-650 nM) and Hoechst Blue (405-450 nM).

A "target site" or "target sequence" refers to a genomic nucleic acid sequence that defines a portion of a nucleic acid to which a binding molecule may specifically bind under conditions sufficient for binding to occur.

As used herein, the term "T cell receptor" or "TCR" refers to a complex of membrane proteins that participate in the activation of T cells in response to the presentation of antigen. The TCR is responsible for recognizing antigens bound to major histocompatibility complex molecules. TCR is composed of a heterodimer of an alpha ($\alpha$) and beta ($\beta$) chain, although in some cells the TCR consists of gamma and delta ($\gamma/\delta$) chains. TCRs may exist in alpha/beta and gamma/delta forms, which are structurally similar but have distinct anatomical locations and functions. Each chain is composed of two extracellular domains, a variable and constant domain. In some embodiments, the TCR may be modified on any cell comprising a TCR, including, for example, a helper T cell, a cytotoxic T cell, a memory T cell, regulatory T cell, natural killer T cell, and gamma delta T cell.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

To "treat" a disease as the term is used herein, means to reduce the frequency or severity of at least one sign or symptom of a disease or disorder experienced by a subject.

As used herein, a "side population T cell" or "$T_{SP}$ cell" refers to a distinct subset of tissue resident memory ($T_{RM}$) cells that display a quiescent/G0/slow-cycling phenotype.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, Sendai viral vectors, adenoviral vectors, adeno-associated virus vectors, retroviral vectors, lentiviral vectors, and the like.

Ranges: throughout this disclosure, various aspects of the disclosure can be presented in a range format. It should be understood that the description in range format is merely for convenience and brevity and should not be construed as an inflexible limitation on the scope of the disclosure. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present disclosure relates to compositions comprising and methods for use of a novel subtype of tissue-resident memory ($T_{RM}$) T cells that display a quiescent (G0) phenotype: side population T ($T_{SP}$) cells. In one embodiment, $T_{SP}$ cells are mobilized from a subject's tissue or bone marrow into the circulation. In other embodiments, $T_{SP}$ cells are useful for methods of adoptive T cell transfer.

Side Population T ($T_{SP}$) Cells

In the present disclosure, data are presented that illustrate that the SP phenotype marks a discrete subset of human and murine T cells that display distinct biologic and functional properties. $T_{RM}$ cells in human and murine tissues such as the gut are highly enriched in SP T ($T_{SP}$) cells, and these cells particularly mark a $T_{RM}$ subset with a quiescent/slow-cycling phenotype. Human $T_{SP}$ cells share overlapping transcriptional gene expression programs with $T_{RM}$ cells (Mackay et al. Nat Immunol. 2013; 14(12):1294-301) including several members of NR4A orphan nuclear receptor family, also implicated in HSC quiescence. As demonstrated herein, two key signature gene families identified in human $T_{SP}$ cells, ABC transporters and NR4A1, impact the biology of $T_{RM}$ cells. Harnessing the properties of $T_{SP}$ cells may therefore allow manipulation of tissue resident memory in humans. As shown herein, their quiescence, propensity for tissue localization, and potential to mobilize into circulation also makes them attractive candidates for adoptive cellular therapies targeting cancer.

One aspect of the present disclosure relates to a $T_{SP}$ cell or population of $T_{SP}$ cells displaying a quiescent phenotype. A quiescent phenotype refers to a slow-cycling phenotype wherein cells are in the G0 stage of the cell cycle. In the G0 stage of the cell cycle, the cells are neither dividing nor preparing to divide. In certain embodiments, the $T_{SP}$ cell expresses at least one ATP binding cassette (ABC) transporter and at least one transcription factor from the nuclear receptor subfamily 4 (NR4A) family.

ATP-binding cassette (ABC) transporters make up the largest transporter gene family and are essential for many processes in the cell. These proteins translocate a wide variety of substrates including sugars, amino acids, metal ions, peptides, and proteins, and a large number of hydrophobic compounds and metabolites across extra- and intracellular membranes.

Examples of ABC transporter genes useful in the present disclosure include, but are not limited to, ABCA1 (ABC1), ABCA2 (ABC2), ABCA3 (ABC3, ABCC), ABCA4 (ABCR), ABCA5, ABCA6, ABCA7, ABCA8, ABCA9, ABCA10, ABCA12, ABCA13, ABCB1 (PGY1, MDR), ABCB2 (TAP1), ABCB3 (TAP2), ABCB4 (PGY3), ABCB5, ABCB6 (MTABC3), ABCB7 (ABC7), ABCB8 (MABC1), ABCB9, ABCB10 (MTABC2), ABCB11 (SPGP), ABCC1 (MRP1), ABCC2 (MRP2), ABCC3 (MRP3), ABCC4 (MRP4), ABCC5 (MRP5), ABCC6 (MRP6), CFTR (ABCC7), ABCC8 (SUR), ABCC9 (SUR2), ABCC10 (MRP7), ABCC11, ABCC12, ABCD1 (ALD), ABCD2 (ALDL1, ALDR), ABCD3 (PXMP1, PMP70), ABCD4 (PMP69, P70R), ABCE1 (OABP, RNS4I), ABCF1 (ABC50), ABCF2, ABCF3, ABCG1 (ABC8, White), ABCG2 (ABCP, MXR, BCRP), ABCG4 (White2), ABCG5 (White3), and ABCG8.

Nur (nuclear receptor subfamily 4) is a family of orphan nuclear receptors which act as transcription factors. Members of the NR4A family useful in the present disclosure include, but are not limited to, NR4A1(Nur77), NR4A2, and NR4A3. In one embodiment, $T_{SP}$ cell expresses NR4A1 (Nur77).

In another embodiment the $T_{SP}$ cell expresses at least one gene selected from the group consisting of XCL1, PTGER4, PPP1R15A, GLA, NFKB1D, DUSP6, RASD1, SKIL, TNFSF9, TNF, SIK1, HSPA1A, NR4A3, GADD45B, PHLDA1, GEM, NR4A2, FOSB, EGR1, NR4A1, and ATF3.

In certain embodiments, $T_{SP}$ cells are characterized by their core transcriptome signature comprising EGR1 (early growth response 1), EGR3 (early growth response 3), CCL20 (chemokine (C—C motif) ligand 20), CCL4 (chemokine (C—C motif) ligand 4), TNF (tumor necrosis factor), EGR2 (early growth response 2), TUBB2A (tubulin, beta 2A class IIa), NR4A2 (nuclear receptor subfamily 4, group A, member 2), NR4A2 (nuclear receptor subfamily 4, group A, member 2), NR4A2 (nuclear receptor subfamily 4, group A, member 2), EGR1 (early growth response 1), NR4A3 (nuclear receptor subfamily 4, group A, member 3), EGR1 (early growth response 1), CA2 (carbonic anhydrase II), MIR22/MI R22HG (microRNA 22/MIR22 host gene (non-protein coding)), IER3 (immediate early response 3), CKS2 (CDC28 protein kinase regulatory subunit 2), LOC284454 (uncharacterized LOC284454), HSPA2 (heat shock 70 kDa protein 2), FOSB FBJ murine osteosarcoma viral oncogene homolog B), EMP1 (epithelial membrane protein 1), GADD45A (growth arrest and DNA-damage-inducible, alpha, ADAM12/ADAM12-OT1 (ADAM metallopeptidase domain 12/ADAM12 overlapping transcript 1) (non-protein coding)), ATF3 (activating transcription factor 3), ZNF165 (zinc finger protein 165), AREG/AREGB (amphiregulin/amphiregulin B), NR4A3 (nuclear receptor subfamily 4, group A, member 3), ERFFI1 (ERBB receptor feedback inhibitor 1), SPRY1 (sprouty homolog 1, antagonist of FGF signaling), LYZ (lysozyme), ULBP2 (UL16 binding protein 2), IL4I1 (interleukin 4 induced 1), CDKN1A (cyclin-dependent kinase inhibitor 1A (p21, Cip1)), ATXN1 (ataxin 1), NCR3 natural cytotoxicity triggering receptor 3, NCR3 (nuclear factor of kappa light polypeptide gene enhancer in B-cells inhibitor, delta), SERTAD1 (SERTA domain containing 1), PLK2 (polo-like kinase 2), GEM (GTP binding protein overexpressed in skeletal muscle), NCR3 (natural cytotoxicity triggering receptor 3), C15orf48 (chromosome 15 open reading frame 48) APOBEC3A/APOBEC3A_B (apolipoprotein B mRNA editing enzyme, catalytic polypeptide-like 3A/APOBEC3A and APOBEC3B deletion hybrid), RGS16 (regulator of G-protein signaling 16), OTTHUMG0 0000178019/RP11-199F11.2, TNFRSF12A (tumor necrosis factor receptor superfamily, member 12A), TUBB3 (tubulin, beta 3 class III), CCNB1 (cyclin B1), TUBB4B (tubulin, beta 4B class IVb), UBE2S (ubiquitin-conjugating enzyme E2S EGR1 early growth response 4), SNORD3A/SNORD3B-1/SNORD3B-2/SNORD3C/SNORD3D (small nucleolar RNA, C/D box 3A/3B-1/3B-2/3C/3D), TUBB3 (tubulin, beta 3 class III), SPRY2 sprouty homolog 2 (Drosophila), NEU1 (sialidase 1 (lysosomal sialidase)), MAFF v-maf musculoaponeurotic fibrosarcoma oncogene homolog F (avian), H2AFX (H2A histone family, member X), EMP1 (epithelial membrane protein 1), BRE-ASI (BRE antisense RNA 1), VIM (vimentin) CDT1 (chromatin licensing and DNA replication factor 1), THAP2 (THAP domain containing, apoptosis associated protein 2), SIK1 (salt-inducible kinase 1), SGK1 (serum/glucocorticoid regulated kinase 1), TP53INP2 (tumor protein p53 inducible nuclear protein 2, IL1RN (interleukin 1 receptor antagonist), ADM (adrenomedullin), SUB1 (SUB1 homolog (S. cerevisiae)), GPR84 (G protein-coupled receptor 84), TRAF4 (TNF receptor-associated factor 4), NECAP2 (NECAP endocytosis associated 2), ABCA1 (ATP-binding cassette, subfamily A (ABC1), member 1), KLF10 (Kruppel-like factor 10), NR4A3 (nuclear receptor subfamily 4, group A, member 3), ARL5B (ADP-ribosylation factor-like 5B), ZBTB10 (zinc finger and BTB domain containing 10), SLC16A14 (solute carrier family 16, member 14 (monocarboxylic acid transporter 14)), TIGD2 (trigger transposable element derived 2), MED7 (mediator complex subunit 7), BRWD1 (bromodomain and WD repeat domain containing 1), ZBTB3 (zinc finger and BTB domain containing 3), FRAT1 (frequently rearranged in advanced T-cell lymphomas), IL16 (interleukin 16), ZNF623 (zinc finger protein 623), TCEANC (transcription elongation factor A (SII) N-terminal and central domain containing), KBTBD7 (kelch repeat and BTB (POZ) domain containing 7), BOLA1 (bolA homolog 1 (E. coli)), GIN1 (gypsy retrotransposon integrase 1), MALSU (mitochondrial assembly of ribosomal large subunit 1), CPT2 (carnitine palmitoyltransferase 2), JRKL (jerky homolog-like (mouse)), CASP4 (caspase 4, apoptosis-related cysteine peptidase), ZKSCAN7 (zinc finger with KRAB and SCAN domains 7), PPAPDC2 (phosphatidic acid phosphatase type 2 domain containing 2), GSPT2 (G1 to S phase transition 2), FANCF (Fanconi anemia, complementation group F), OTTHUMG0 0000175805/RP1-39G22.7, WDR5B (WD repeat domain 5B), ZNF792 (zinc finger protein 792), GIMAP4 (GTPase, IMAP family member 4), KATNBL1 (katanin p80 subunit B-like 1), CCDC71L (coiled-coil domain containing 71-like), and GIMAP8 (GTPase, IMAP family member 8).

The $T_{SP}$ cell can be CD8$^+$ and/or CD4$^+$. In certain embodiments, $T_{SP}$ cells are enriched for the $T_{RM}$ phenotype (CD69$^+$CD103$^+$).

In some aspects of the disclosure, the $T_{SP}$ cell is in a container comprising at least one non-naturally occurring component. The non-naturally occurring container may be any vessel holding or capable of holding a $T_{SP}$ cell or composition comprising a $T_{SP}$ cell. The non-naturally occurring component may be, without limitation, glass, plastic, metal, or a composite material. The non-naturally occurring container may be, without limitation, a tube, capsule, dish, plate, flask, packet, vial, pouch, jar, or bottle.

Another aspect of the disclosure includes a kit comprising a $T_{SP}$ cell in a non-naturally occurring container. The $T_{SP}$ cell expresses at least one ATP binding cassette (ABC) transporter and at least one transcription factor from the nuclear receptor subfamily 4 (NR4A) family. The kit includes instructional material for use thereof.

Methods

One aspect of the disclosure includes a method of mobilizing a $T_{SP}$ cell in a subject. The method comprises administering to subject a CXCR4 antagonist. The CXCR4 antagonist induces mobilization of the $T_{SP}$ cell from the subject's tissue or bone marrow into the subject's circulation.

Another aspect of the disclosure includes a method of obtaining a $T_{SP}$ cell from a subject comprising administering to the subject a CXCR4 antagonist. The CXCR4 antagonist induces mobilization of the $T_{SP}$ cell from the subject's tissue or bone marrow into the subject's circulation. The $T_{SP}$ cell so mobilized from the subject's circulation is isolated.

In one embodiment, the CXCR4 antagonist comprises plerixafor. Plerixafor (AMD3100, Mozobil; Genzyme, Cambridge, Mass., USA), a novel small-molecule antagonist of CXCR4, was approved by the United States Food and Drug Administration (FDA) for use with G-CSF in 2008 to mobilize hematopoietic stem cells to the peripheral blood for collection and subsequent autologous transplantation in patients with non-Hodgkin's lymphoma (NHL) and multiple myeloma (MM) (Rettig et a. Leukemia (2012) 26, 34-53; doi:10.1038/leu.2011.197). However, the present disclosure should not be construed to be limited solely to the use of plerixafor, but rather to include any and all other CXCR4 antagonists that have the property of mobilizing cells in a manner similar to plerixafor.

In certain embodiments, the methods described herein further comprise administering granulocyte-colony stimulating factor (G-CSF) to the subject. Granulocyte-colony stimulating factor (G-CSF) can be used alone or in combination with plerixafor to mobilize $T_{SP}$ cells.

Another aspect of the disclosure provides a method of obtaining a $T_{SP}$ cell from a subject. The method comprises administering to the subject a CXCR4 antagonist, wherein the CXCR4 antagonist induces mobilization of the $T_{SP}$ cell from the subject's tissue or bone marrow into the subject's circulation, and isolating the $T_{SP}$ cell so mobilized from the subject's circulation.

In another aspect, the disclosure includes a method of obtaining a $T_{SP}$ cell from a subject. The method comprises isolating a $T_{SP}$ cell from a subject, wherein the $T_{SP}$ cell displays a quiescent (GO) phenotype, and expresses at least one ABC transporter and at least one transcription factor from the NR4A family. In certain embodiments, the $T_{SP}$ cell can be obtained from a subject's gut, liver, skin, or bone marrow.

Another aspect of the disclosure includes a method of adoptive cell transfer in a subject. The method comprises administering to the subject a CXCR4 antagonist. The CXCR4 antagonist induces mobilization of the $T_{SP}$ cell from the subject's tissue or bone marrow into the subject's circulation. The $T_{SP}$ cell so mobilized from the subject's circulation is isolated and modified ex vivo. The modified $T_{SP}$ cell is administered to the subject.

In another aspect, the disclosure includes a method of adoptive cell transfer in a subject comprising isolating a $T_{SP}$ cell from a subject, wherein the $T_{SP}$ cell displays a quiescent (GO) phenotype, and expresses at least one ABC transporter and at least one transcription factor from the NR4A family, modifying the isolated $T_{SP}$ cell ex vivo, and administering the modified $T_{SP}$ cell to the subject.

In Certain Embodiments, the Mobilized $T_{SP}$ Cell Differentiates into a $T_{RM}$ Cell.

Certain embodiments of the present disclosure further comprise expanding the isolated $T_{SP}$ cell ex vivo.

Sources of T Cells

In certain aspects of the present disclosure, a $T_{SP}$ cell is obtained or isolated from a subject. Non-limiting examples of subjects include humans, dogs, cats, mice, rats, and transgenic species thereof. Preferably, the subject is a human. $T_{SP}$ cells can be obtained from a number of sources, including but not limited to tissues, peripheral blood mononuclear cells, bone marrow, gut, liver, lymph nodes, spleen, umbilical cord, skin, blood, plasma, serum, intestinal epithelium, intestinal epithelial lymphocytes (IEL), Peyer's patches (PP), lamina propria lymphocytes (LPL), and mucosa.

In certain embodiments, $T_{SP}$ cells can be obtained from a unit of blood collected from a subject using any number of techniques known to the skilled artisan, such as Ficoll separation. In one embodiment, cells from the circulating blood of an individual are obtained by apheresis or leukapheresis. The apheresis product typically contains lymphocytes, including T cells, monocytes, granulocytes, B cells, other nucleated white blood cells, red blood cells, and platelets. The cells collected by apheresis may be washed to remove the plasma fraction and to place the cells in an appropriate buffer or media, such as phosphate buffered saline (PBS) or wash solution lacks calcium and may lack magnesium or may lack many if not all divalent cations, for subsequent processing steps. After washing, the cells may be resuspended in a variety of biocompatible buffers, such as, for example, Ca-free, Mg-free PBS. Alternatively, the undesirable components of the apheresis sample may be removed and the cells directly resuspended in culture media.

In another embodiment, $T_{SP}$ cells are isolated from peripheral blood by lysing the red blood cells and depleting the monocytes, for example, by centrifugation through a PERCOLL™ gradient. Alternatively, $T_{SP}$ cells can be isolated from bone marrow. $T_{SP}$ cells can be further isolated by positive or negative selection techniques. In one embodiment, $T_{SP}$ cells are selected and isolated based on their ability to efflux Hoechst dye.

Enrichment of a T cell population by negative selection can be accomplished using a combination of antibodies directed to surface markers unique to the negatively selected cells. A preferred method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion.

T cells can also be frozen after the washing step, which does not require the monocyte-removal step. While not wishing to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, in a non-limiting example, one method involves using PBS containing 20% DMSO and 8% human serum albumin, or other suitable cell freezing media. The cells are then frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

Expansion of T Cells

As demonstrated by the data disclosed herein, expanding the $T_{SP}$ cells by the methods disclosed herein can be multiplied by about 10 fold, 20 fold, 30 fold, 40 fold, 50 fold, 60 fold, 70 fold, 80 fold, 90 fold, 100 fold, 200 fold, 300 fold, 400 fold, 500 fold, 600 fold, 700 fold, 800 fold, 900 fold, 1000 fold, 2000 fold, 3000 fold, 4000 fold, 5000 fold, 6000 fold, 7000 fold, 8000 fold, 9000 fold, 10,000 fold, 100,000 fold, 1,000,000 fold, 10,000,000 fold, or greater, and any and all whole or partial integers therebetween. In one embodiment, the $T_{SP}$ cells expand in the range of about 20 fold to about 50 fold.

Following culturing, the $T_{SP}$ cells can be incubated in cell medium in a culture apparatus for a period of time or until the cells reach confluency or high cell density for optimal passage before passing the cells to another culture apparatus. The culturing apparatus can be of any culture apparatus commonly used for culturing cells in vitro. Preferably, the level of confluence is 70% or greater before passing the cells to another culture apparatus. More preferably, the level of confluence is 90% or greater. A period of time can be any time suitable for the culture of cells in vitro. The $T_{SP}$ cell medium may be replaced during the culture of the $T_{SP}$ cells at any time. Preferably, the $T_{SP}$ cell medium is replaced about every 2 to 3 days. The $T_{SP}$ cells are then harvested from the culture apparatus whereupon the $T_{SP}$ cells can be used immediately or cryopreserved to be stored for use at a later time. In one embodiment, the disclosure includes cryopreserving the expanded $T_{SP}$ cells. The cryopreserved $T_{SP}$ cells are thawed prior to introducing nucleic acids into the $T_{SP}$ cell.

Another procedure for ex vivo expansion cells is described in U.S. Pat. No. 5,199,942 (incorporated herein by reference). Expansion, such as described in U.S. Pat. No. 5,199,942 can be an alternative or in addition to other methods of expansion described herein. Briefly, ex vivo culture and expansion of T cells comprises the addition to the cellular growth factors, such as those described in U.S. Pat. No. 5,199,942, or other factors, such as flt3-L, IL-1, IL-3 and c-kit ligand. In one embodiment, expanding the T cells comprises culturing the T cells with a factor selected from the group consisting of flt3-L, IL-1, IL-3 and c-kit ligand.

The culturing step as described herein (contact with agents as described herein or after electroporation) can be very short, for example less than 24 hours such as 1, 2, 3, 4, 5, 6, 7, 8, 9, 10, 11, 12, 13, 14, 15, 16, 17, 18, 19, 20, 21, 22, or 23 hours. The culturing step as described further herein (contact with agents as described herein) can be longer, for example 1, 2, 3, 4, 5, 6, 7, 8, 9, 10, 11, 12, 13, 14, or more days.

Various terms are used to describe cells in culture. Cell culture refers generally to cells taken from a living organism and grown under controlled condition. A primary cell culture is a culture of cells, tissues or organs taken directly from an organism and before the first subculture. Cells are expanded in culture when they are placed in a growth medium under conditions that facilitate cell growth and/or division, resulting in a larger population of the cells. When cells are expanded in culture, the rate of cell proliferation is typically measured by the amount of time required for the cells to double in number, otherwise known as the doubling time.

Each round of subculturing is referred to as a passage. When cells are subcultured, they are referred to as having been passaged. A specific population of cells, or a cell line, is sometimes referred to or characterized by the number of times it has been passaged. For example, a cultured cell population that has been passaged ten times may be referred to as a P10 culture. The primary culture, i.e., the first culture following the isolation of cells from tissue, is designated P0. Following the first subculture, the cells are described as a secondary culture (P1 or passage 1). After the second subculture, the cells become a tertiary culture (P2 or passage 2), and so on. It will be understood by those of skill in the art that there may be many population doublings during the period of passaging; therefore, the number of population doublings of a culture is greater than the passage number. The expansion of cells (i.e., the number of population doublings) during the period between passaging depends on many factors, including but not limited to the seeding density, substrate, medium, and time between passaging.

In one embodiment, the cells may be cultured for several hours (about 3 hours) to about 14 days or any hourly integer value in between. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-gamma, IL-4, IL-7, GM-CSF, IL-10, IL-12, IL-15, TGF-beta, and TNF-α, or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

In one embodiment, the method of expanding the T cells can further comprise isolating the expanded T cells for further applications. In another embodiment, the method of expanding can further comprise a subsequent electroporation of the expanded T cells followed by culturing. The subsequent electroporation may include introducing a nucleic acid encoding an agent, such as a transducing the expanded T cells, transfecting the expanded T cells, or electroporating the expanded T cells with a nucleic acid, into the expanded population of T cells, wherein the agent further stimulates the T cell. The agent may stimulate the T cells, such as by stimulating further expansion, effector function, or another T cell function.

Pharmaceutical Compositions

Pharmaceutical compositions of the present disclosure may comprise the modified T cell as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present disclosure are preferably formulated for intravenous administration.

Pharmaceutical compositions of the present disclosure may be administered in a manner appropriate to the disease to be treated (or prevented). The quantity and frequency of administration will be determined by such factors as the condition of the patient, and the type and severity of the patient's disease, although appropriate dosages may be determined by clinical trials.

The cells of the disclosure to be administered may be autologous, allogeneic or xenogeneic with respect to the subject undergoing therapy.

Cells of the disclosure can be administered in dosages and routes and at times to be determined in appropriate preclinical and clinical experimentation and trials. Cell compositions may be administered multiple times at dosages within these ranges. Administration of the cells of the disclosure may be combined with other methods useful to treat the desired disease or condition as determined by those of skill in the art.

It can generally be stated that a pharmaceutical composition comprising the modified T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

The administration of the modified T cells of the disclosure may be carried out in any convenient manner known to those of skill in the art. The cells of the present disclosure may be administered to a subject by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In other instances, the cells of the disclosure are injected directly into a site of inflammation in the subject, a local disease site in the subject, a lymph node, an organ, a tumor, and the like.

It should be understood that the method and compositions that would be useful in the present disclosure are not limited to the particular formulations set forth in the examples. The following examples are put forth so as to provide those of ordinary skill in the art with a complete disclosure and description of how to make and use the cells, expansion and culture methods, and therapeutic methods of the disclosure, and are not intended to limit the scope of what the inventors regard as their disclosure.

The practice of the present disclosure employs, unless otherwise indicated, conventional techniques of molecular biology (including recombinant techniques), microbiology, cell biology, biochemistry and immunology, which are well within the purview of the skilled artisan. Such techniques are explained fully in the literature, such as, "Molecular Cloning: A Laboratory Manual", fourth edition (Sambrook, 2012); "Oligonucleotide Synthesis" (Gait, 1984); "Culture of Animal Cells" (Freshney, 2010); "Methods in Enzymology" "Handbook of Experimental Immunology" (Weir, 1997); "Gene Transfer Vectors for Mammalian Cells" (Miller and Calos, 1987); "Short Protocols in Molecular Biology" (Ausubel, 2002); "Polymerase Chain Reaction: Principles, Applications and Troubleshooting", (Babar, 2011); "Current Protocols in Immunology" (Coligan, 2002). These techniques are applicable to the production of the polynucleotides and polypeptides of the disclosure, and, as such, may be considered in making and practicing the disclosure. Particularly useful techniques for particular embodiments will be discussed in the sections that follow.

EXPERIMENTAL EXAMPLES

The disclosure is further described in detail by reference to the following experimental examples. These examples are provided for purposes of illustration only, and are not intended to be limiting unless otherwise specified. Thus, the disclosure should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present disclosure and practice the claimed methods. The following working examples therefore, specifically point out the exemplary embodiments of the present disclosure, and are not to be construed as limiting in any way the remainder of the disclosure.

The Materials and Methods Employed in these Experiments are Now Described.

Mice:

C57BL/6j mice from Jackson laboratory and Thy-1.1$^+$ TCR transgenic mice (Pircher et al. *Nature.* 1989, 342 (6249):559-61) that recognize the H-2D$^b$ gp33 epitope were used where indicated. H2B GFP mice were purchased from Jackson laboratory. ABCG2$^{-/-}$ ABCB1a/b$^{-/-}$ mice and FVB-N mice were purchased from Taconic.

Mice Infections:

For LCMV infections mice were intraperitoneally (i.p) infected with 2×10$^5$ plaque forming units (p.f.u) LCMV Armstrong (Arm). For Flu infections, mice were inoculated intranasally (i.n) with 0.8×10$^5$ TCID50 recombinant x31-OVA influenza virus expressing OVA$_{257-262}$ (SIINFEEKL).

Human Samples:

Peripheral blood mononuclear cells (PBMCs) from healthy donors were isolated from buffy coats purchased from New York Blood Center. Gut T cells were obtained from uninvolved intestine in patients undergoing surgery for diverticular disease or gut biopsies. Bone marrow aspirates were obtained from patients with cancer undergoing diagnostic bone marrow biopsies. In some patients, blood samples were collected before and after stem cell mobilization protocol with plerixafor.

Isolation of Intestinal and Skin T Cells:

Peyer's patches (PP) were first isolated, followed by isolation of IEL and lamina propria lymphocytes (LPL). After removal of PP, intestines were cut longitudinally and the intestinal contents along with mucus were removed by gentle scrapping. The intestines were then cut into small pieces and incubated in PBS buffer containing 1 mM EDTA, 1 mM dithiothreitol (DTT) and 5% FBS at 37° C. in an incubator-shaker at 250 RPM for 15 min. The supernatant was collected to isolate the IELs while remaining intestinal pieces were incubated further in LPL/collagenase (1 mg/ml)/DNase (1U/ml) in PBS solution at 37° C. in an incubator shaker for 10 min for the isolation of LPLs. Skin T cells were obtained from human skin following methods previously described (Watanabe et al. *Sci Transl Med.* 2015; 7(279): 279ra39).

Flow Cytometry:

Single cell suspensions were made from human and mouse tissues. Cell surface FACS staining was performed in FACS buffer (PBS+2% FBS) by incubating cells with with fluorochrome-conjugated antibodies for 30 minutes on ice in dark. After staining, the cells were washed with FACS buffer and analyzed with BD LSR-II. Intracellular staining was performed using BD reagents following manufacturer's protocol. Flow cytometry antibodies for human and mouse were purchased from BD, ebiosciences, Biolegend and Cell signaling. Flow cytometry data was acquired on BD LSRII with Diva software and analyzed with FlowJo 9.7.7 software (Treestar).

Detection of Side Population T Cells:

Hoechst staining was performed on single cell suspensions of mouse and human cells at 1 to 2 million cells/ml by following a previously described method (Goodell et al. *J Exp Med.* 1996; 183(4):1797-806). In brief, the cells were incubated with Hoechst 33342 (5 µg/ml) (Sigma-Aldrich) in 2% FCS, 1 mM HEPES with or without Verapamil (50 µM) (Sigma-Aldrich) for 90 min at 37° C. in darkness with intermittent shaking. The cells were then washed in ice-cold Hoechst wash buffer and analyzed with BD LSR-II containing UV laser.

Hoechst-PY Staining:

G0/G1 analysis was performed as previously described (Liu et al. *Cell stem cell.* 2009; 4(1):37-48). In brief, cells were incubated in Hoechst 33342 buffer for 1h at 37° C. After that Pyronin Y (5 µg/ml; Sigma-Aldrich) was added and incubated for additional 30 min. Subsequently, cells were washed with ice-cold buffer and analyzed using BD-LSRII.

Adoptive Transfer of Human T Cells into NSG Mice:

Human SP T cells and control T cells were FACS sorted and adoptively transferred via intravenous (i.v.) injection with 50-100×1000 T cells/mouse. To reduce the variability in each experiment 3 replicate mice from each group received the sorted SP T cells or control T cells from the same donor. Mice were sacrificed at 8-10 weeks. Organs like skin, liver and small intestine were tested for tissue pathology. Spleen was harvested and single cell suspensions were made and stained for FACS to detect human T cell engraftment.

Adoptive Transfer of Murine SP CD8+ T Cells:

P14 (Thy 1.1) chimeras were generated and infected with LCMV. At 30 days post infection, SP CD8$^+$ T cells (containing both SP Thy 1.1$^+$ as well as polyclonal SP CD8$^+$ T cells) were sorted and adoptively transferred to RAG mice.

At 3 weeks following transfer, the presence of $T_{RM}$ cells in the gut and $T_{CM}/T_{EM}$ cells in the spleen was analyzed by flow cytometry.

TCR Sequencing:

Genomic DNA was isolated from peripheral blood SP CD8+ T cells or MAIT cells (CD8+CD161+IL18Rα+) and the diversity of TCR was profiled using high-throughput sequencing of rearranged TCR β loci from genomic DNA by Adaptive Biotechnologies (Seattle, Wash.) as previously described (Nair et al. *Blood.* 2015; 125(8): 1256-71).

Microarray Analysis:

RNA from sorted human SP CD4+ and CD8+ T cells was amplified, labeled and hybridized on the Affymetrix Human Genome U133 Plus 2.0 microarray chips. The data were analyzed with Gene Spring GX12.5 (Agilent Technologies) and Partek Genomics Suite (6.6) software, as previously described (Sehgal et al. *Blood.* 2015; 125(26):4042-51). Microarray data have been deposited under GEO with accession number GSE85074.

Immunohistochemistry:

Four to five mice per group (8-12 weeks) were studied in each experiment. Mice were adoptively transferred with $T_{SP}$ and control T cells. After 4 weeks of transfer, mice were euthanized and organs (skin, liver and small intestine) were examined for GVHD. Briefly, tissue sections were prepared from formalin-fixed tissues are used for Hematoxylin and Eosin staining. Severity score were generated based on tissue pathology.

Histone 2BGFP Mice:

H2B-GFP mice (Foudi et al. *Nat Biotechnol.* 2009; 27(1): 84-90) were purchased from Jackson laboratory. Six-week-old mice were fed with doxycycline (Sigma D9891, 2 mg/ml, supplemented with sucrose at 10 mg/ml) added to the drinking water for 2-3 weeks. Mice were then infected with LCMV-arm and kept on doxycycline for 5 more weeks. After 8 weeks of doxycycline treatment, chase was initiated by discontinuing doxycycline for 5 more weeks. Then mice were euthanized and analyzed for label retaining cells.

Statistics:

Two tailed Student's t test was used to compare data between two groups. A p value of less than 0.05 was considered significant.

The Results of the Experiments are Now Described.

Example 1: Detection of Human $T_{SP}$ Cells

Figure 1B:
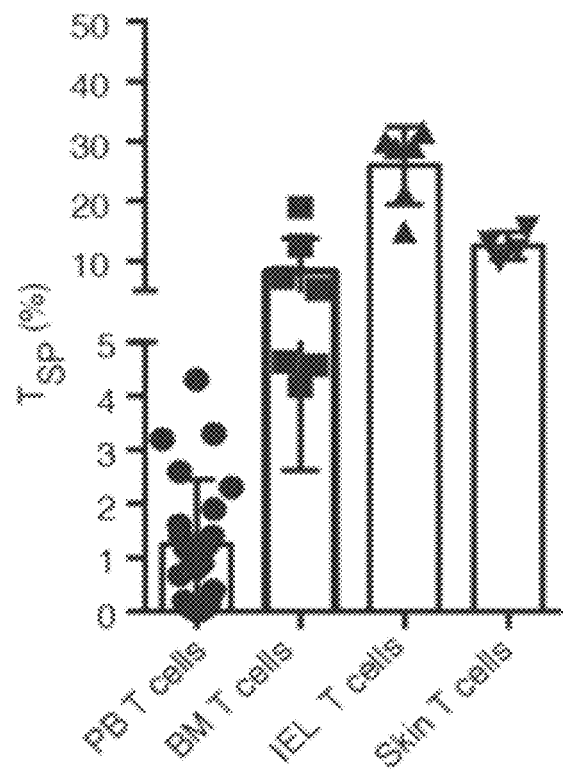
Figure 1C:
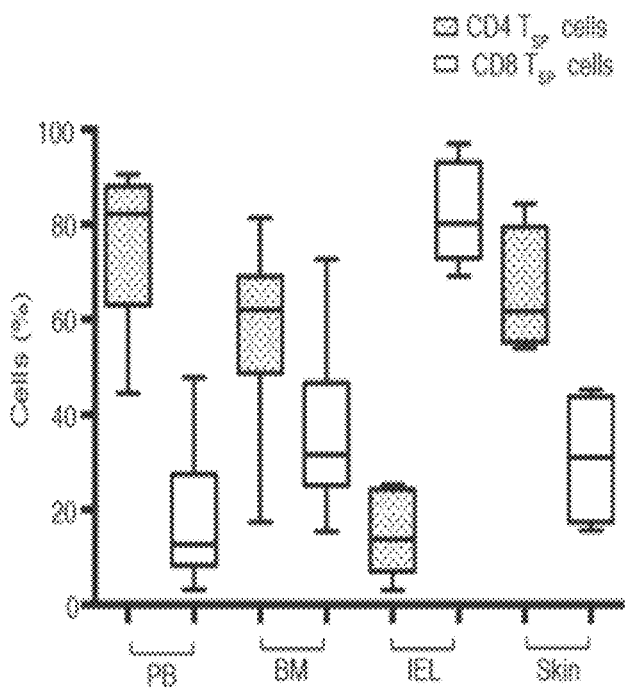
Figure 1D:
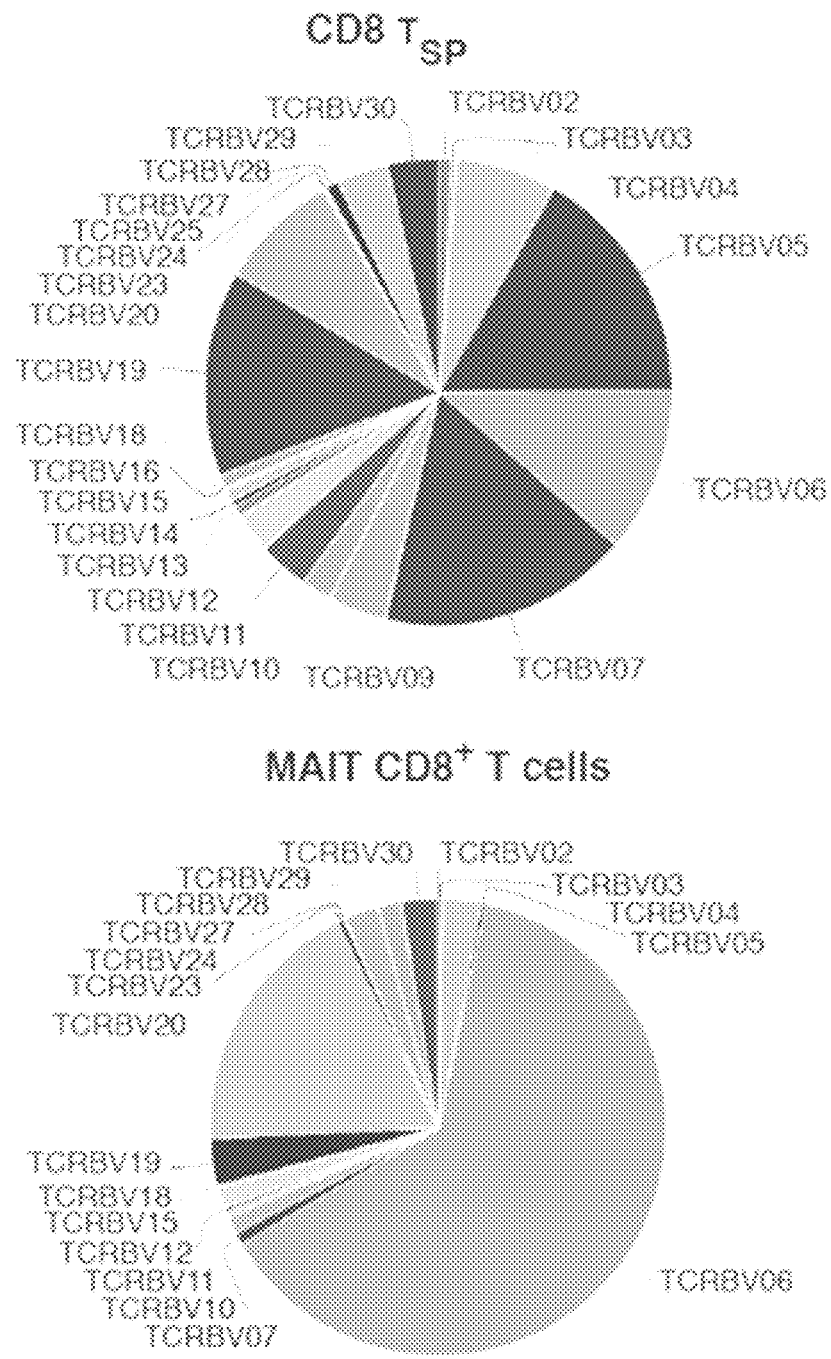
Figure 1E:
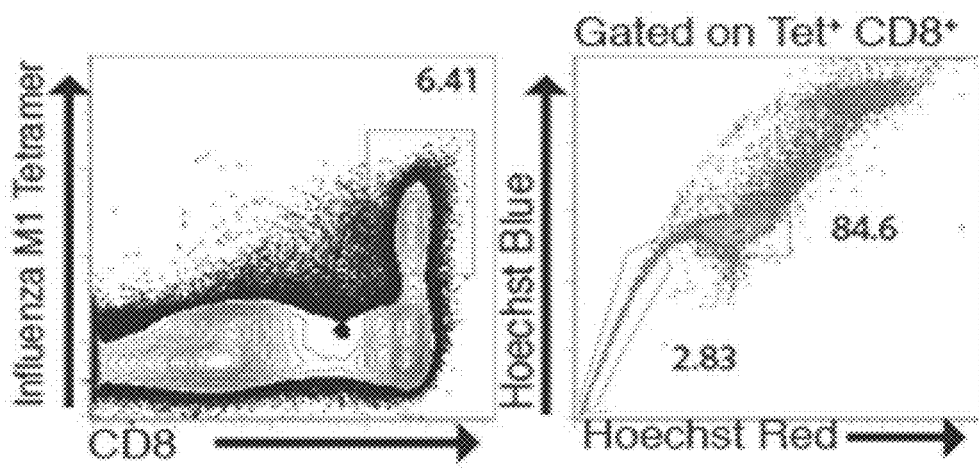
Figure 1F:
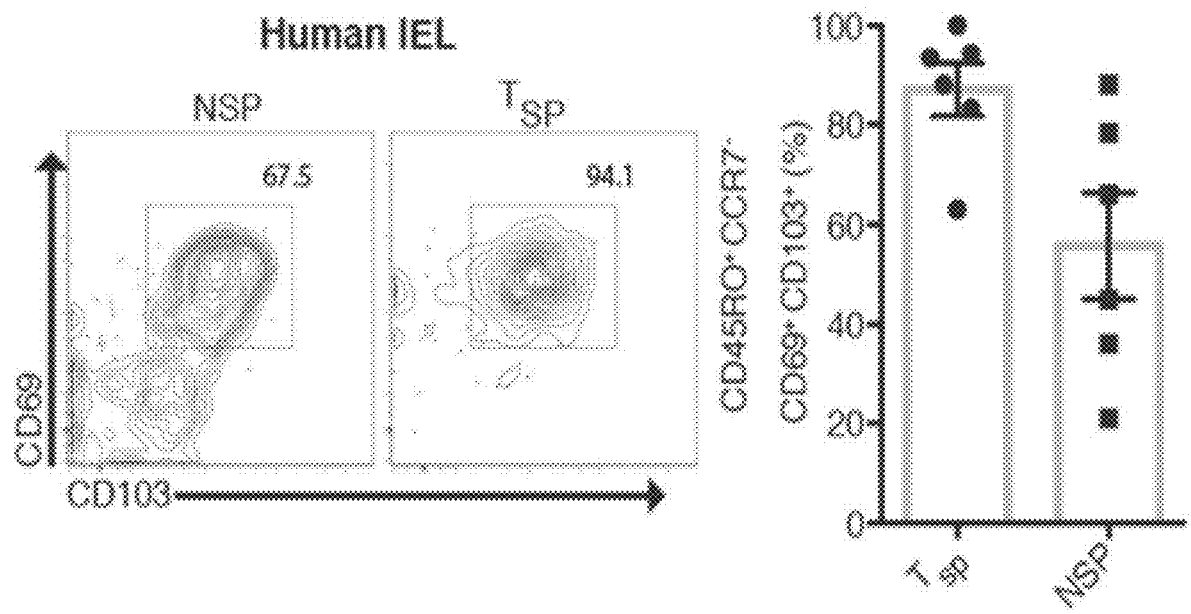
Figure 1G:
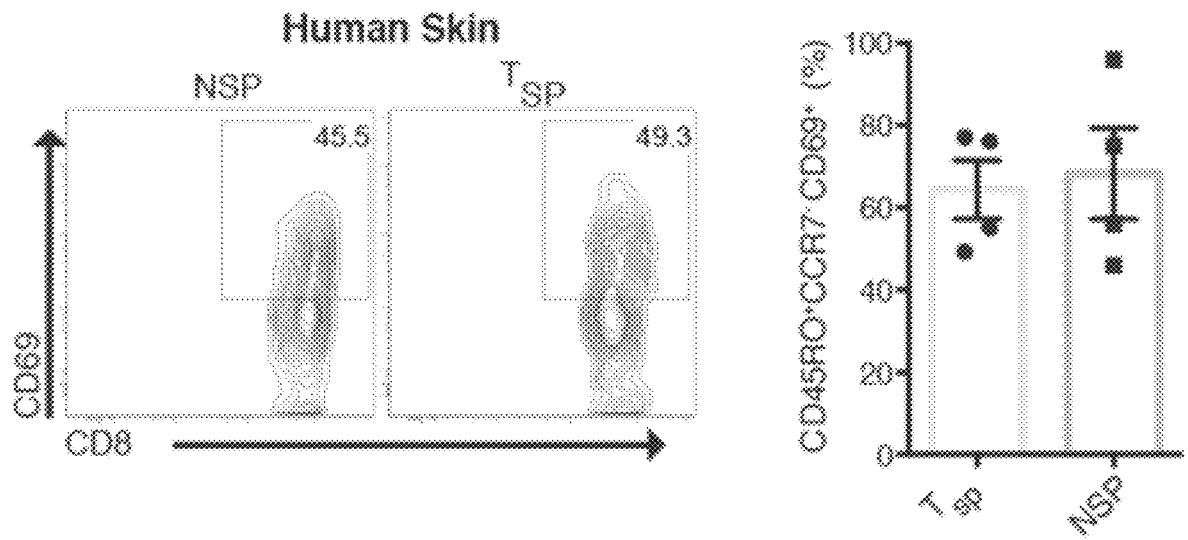
Figure 1H:
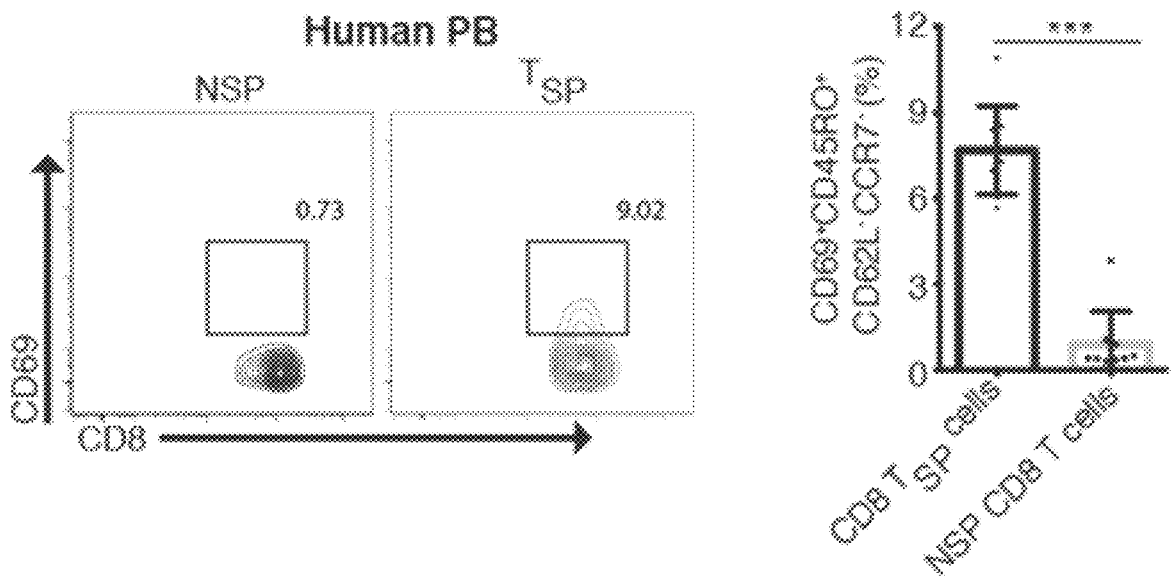

In order to detect human SP T ($T_{SP}$) cells, freshly isolated human T cells from blood, bone marrow (BM), gut and skin were analyzed for the ability to efflux Hoechst dye. Prior treatment with verapamil prevented dye efflux and was utilized as a control. $T_{SP}$ cells could be identified in circulating T cells, but were detected at a much higher frequency in the bone marrow, intestinal epithelium and skin (FIGS. 1A-1B). The proportion of CD4/CD8+ $T_{SP}$ cells with naïve/memory phenotype in blood, BM, skin and intestinal epithelial lymphocytes (IEL) was similar to non-side population (NSP) cells (FIG. 1C and FIGS. 8A-8D). TCR sequencing of purified $T_{SP}$ cells documented the presence of diverse repertoire as opposed to mucosa associated invariant T cell (MAIT) cells with restricted TCRs (FIG. 1D). The presence of $T_{SP}$ phenotype was also detected within human influenza-matrix peptide specific memory T cells (FIG. 1E). Nearly all $T_{SP}$ cells in the gut were CD69+CD103+, consistent with tissue resident memory ($T_{RM}$) T cell phenotypes (FIG. 1F). Similar enrichment of CD69+CCR7− $T_{RM}$ cells was not observed in skin CD8 $T_{SP}$ cells (FIG. 1G). In contrast to T cells within tissues, only a small fraction of T cells within human PBMCs express CD69. Interestingly, these circulating CD69+ human T cells are enriched within $T_{SP}$ cells, and have a phenotype of CCR7−, CD62L− CD45RO+ CD45RA− and IL7R$^{low}$ T cells (FIG. 1H). Taken together, these results show that human $T_{SP}$ cells have a diverse phenotype and can be detected in several tissues but are particularly enriched in $T_{RM}$ cells in tissues such as the gut.

Example 2: Enrichment of $T_{RM}$ Phenotype within Murine $T_{SP}$ Cells

Figure 2A:
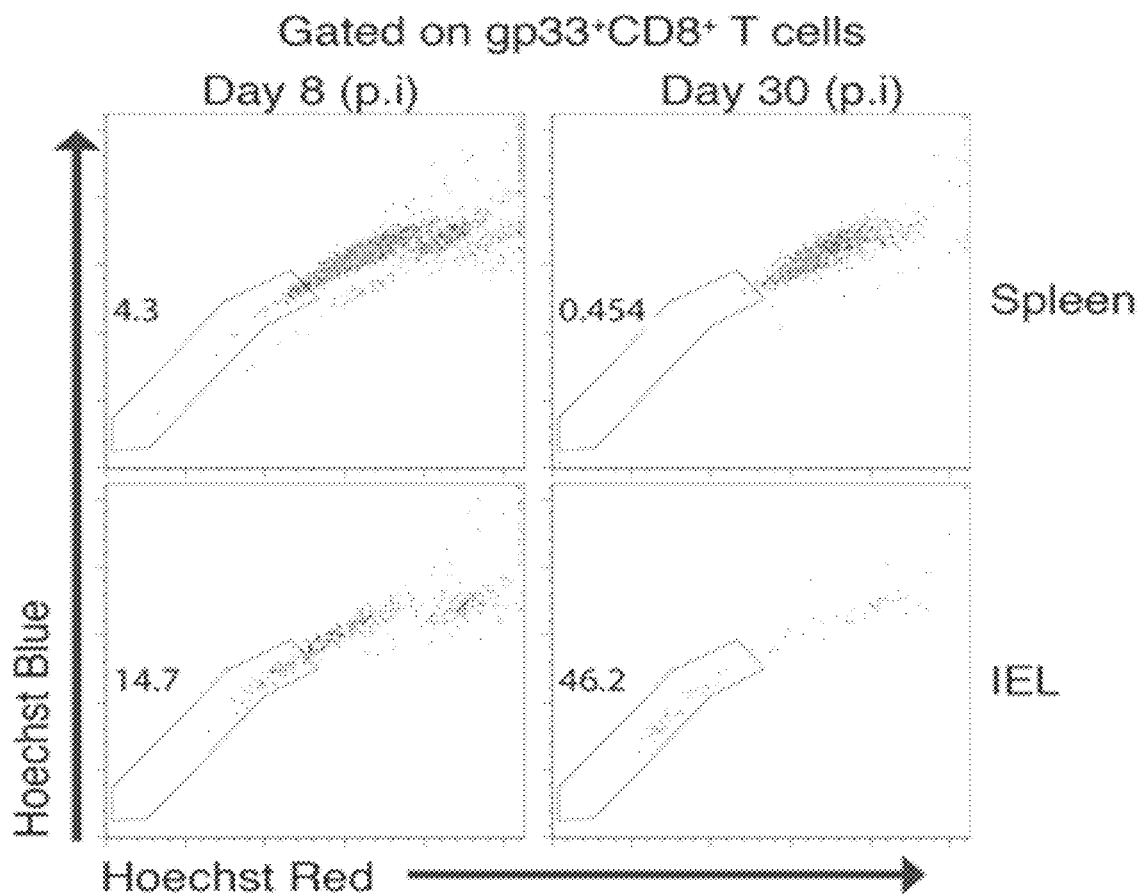
FIGS. 2A-2D are a series of plots showing SP phenotype marks LCMV specific CD8 $T_{RM}$ cells.
Figure 2B:
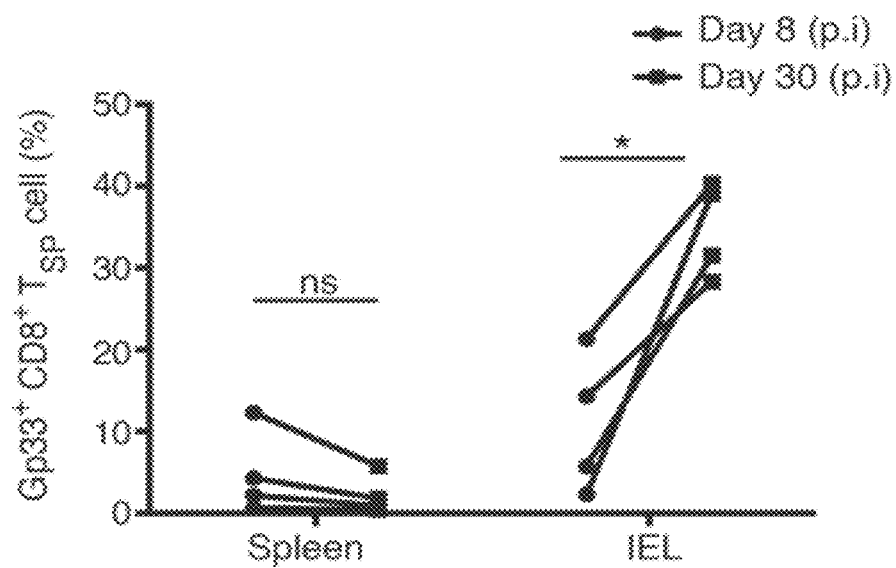
Figure 2C:
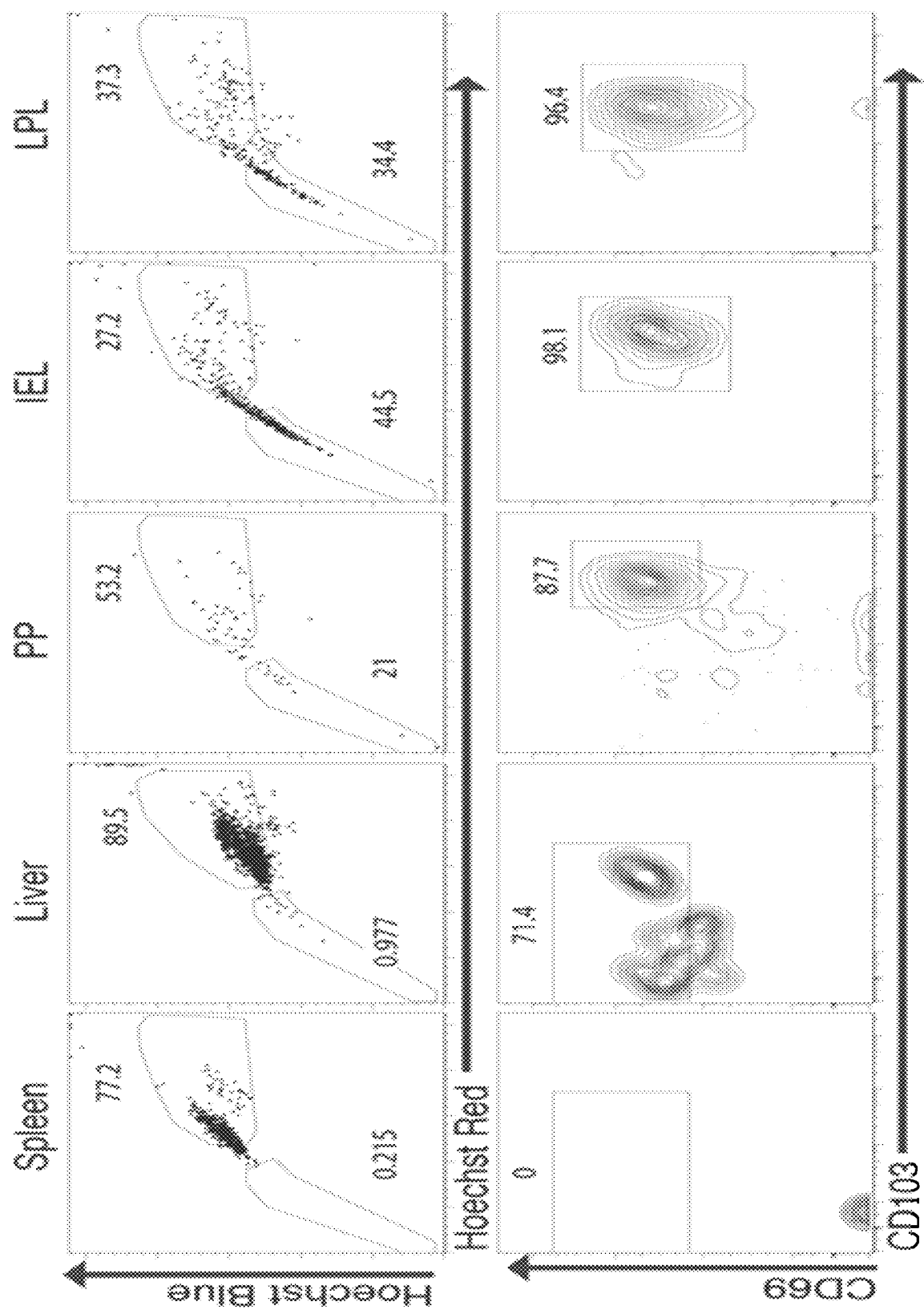
Figure 2D:
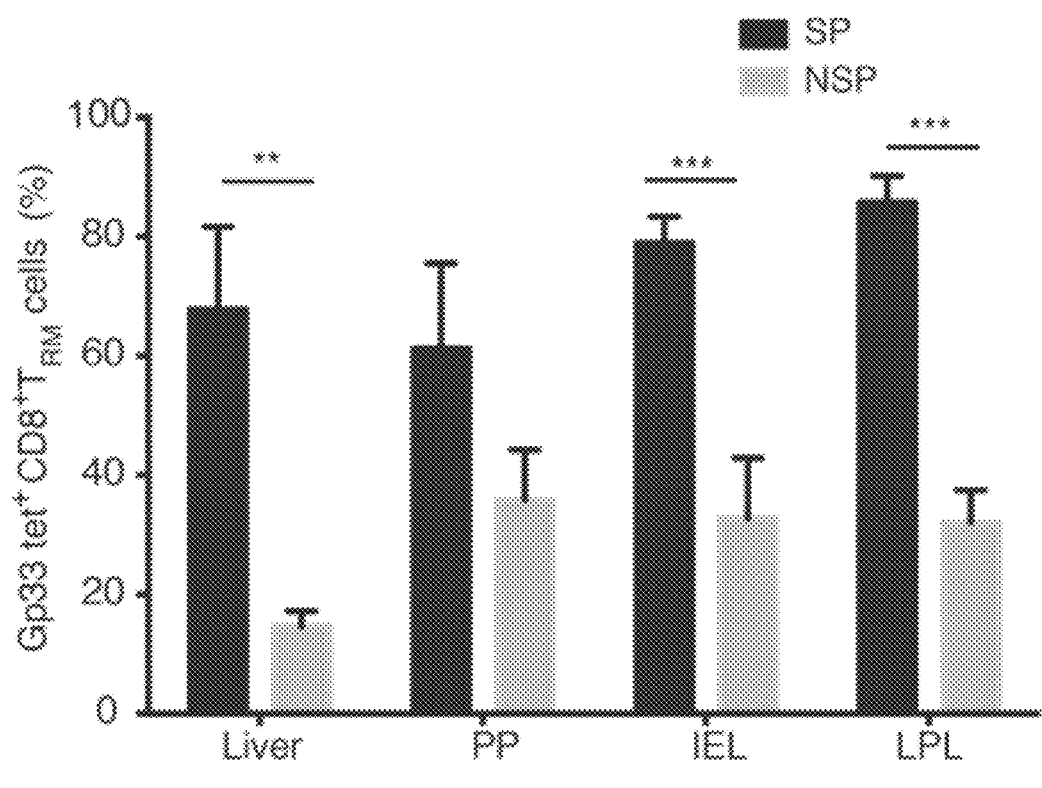
Figure 9A:
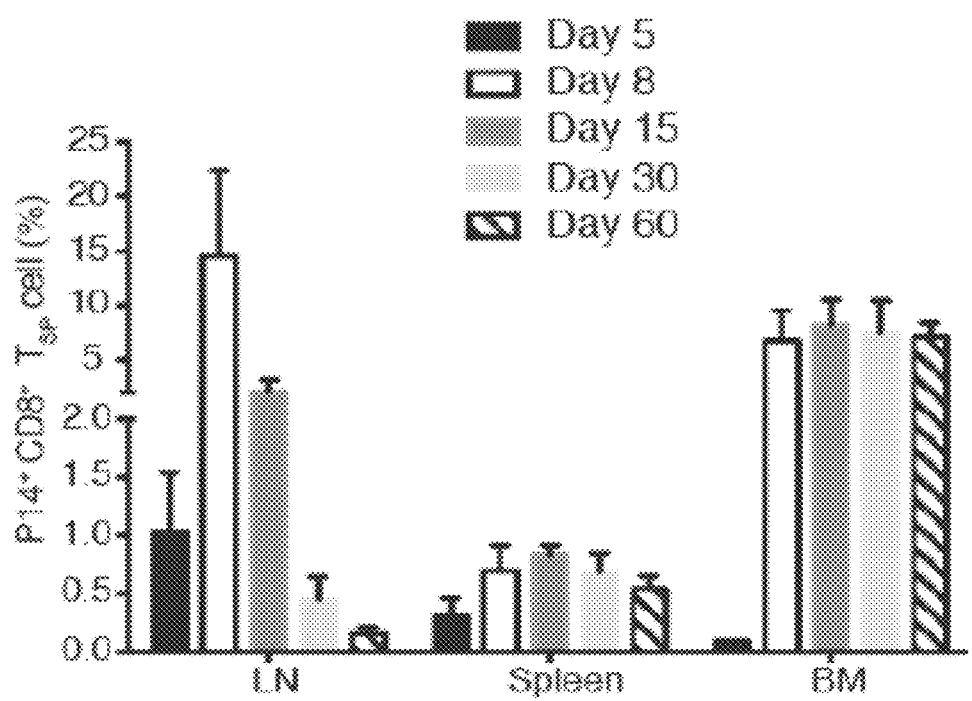
FIGS. 9A-9D are a series of graphs showing kinetics of CD8 $T_{sp}$ in mice. P14 chimeras were infected with LCMV-arm and analyzed sequentially.
Figure 9B:
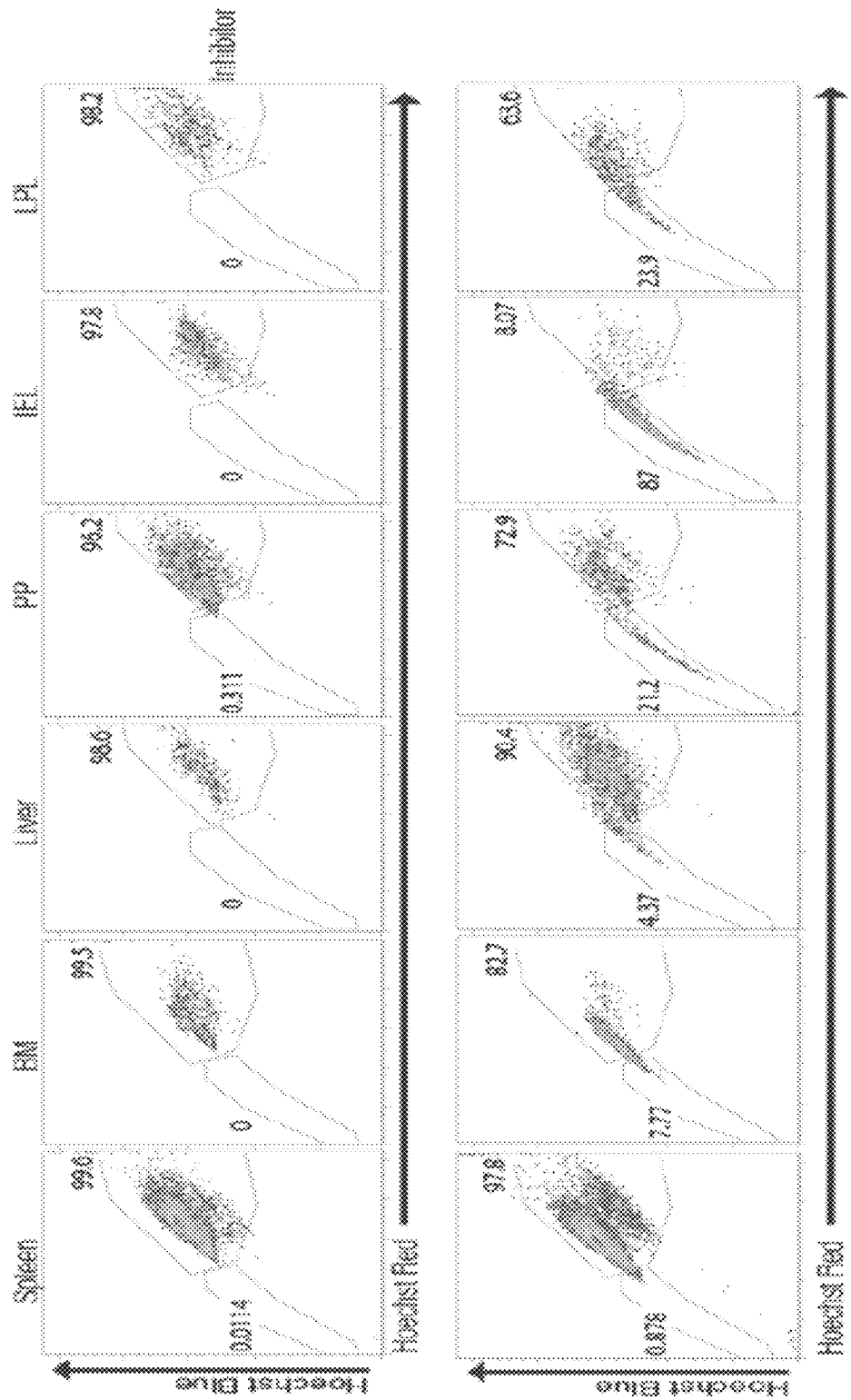
Figure 9C:
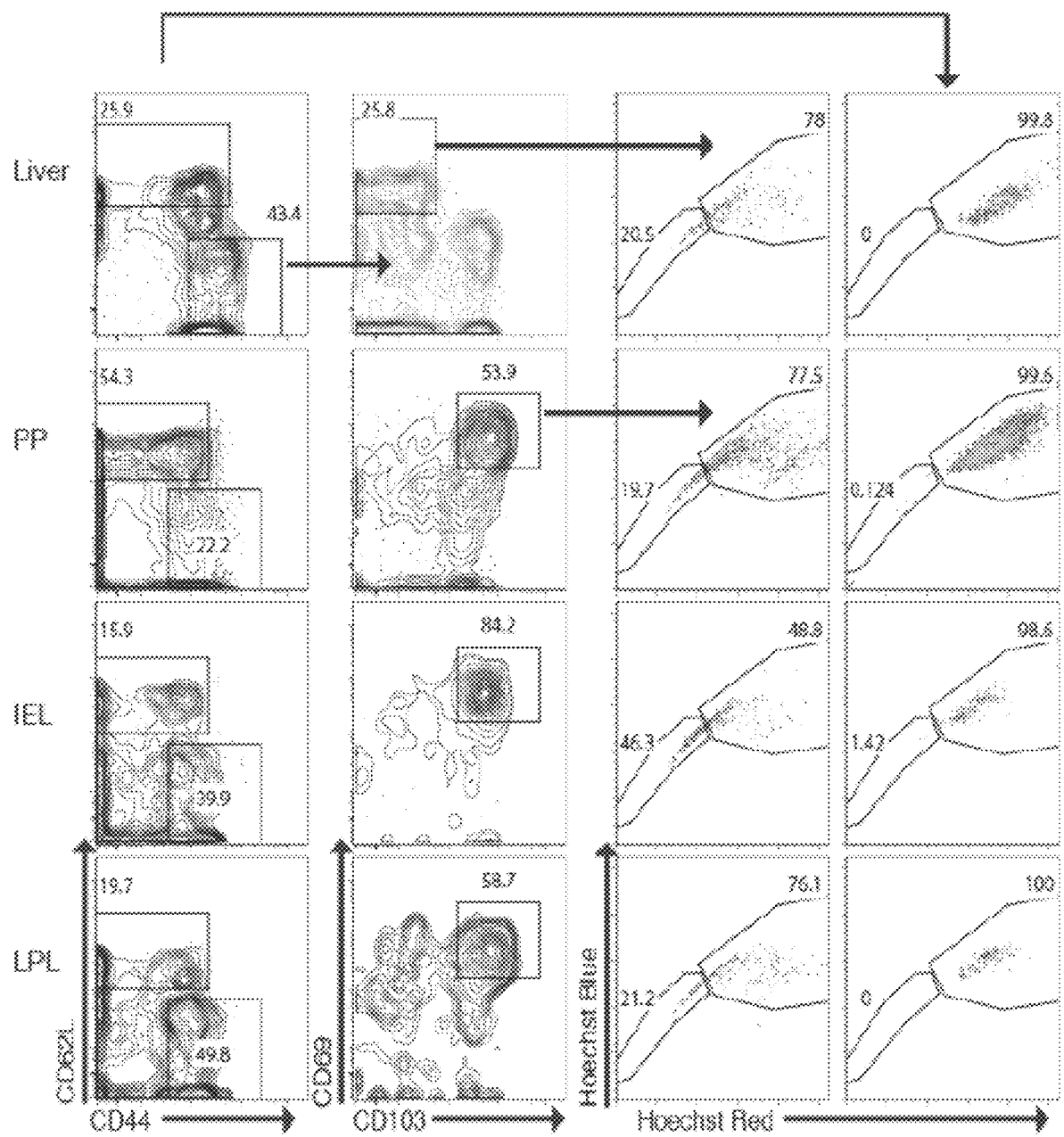
Figure 9D:
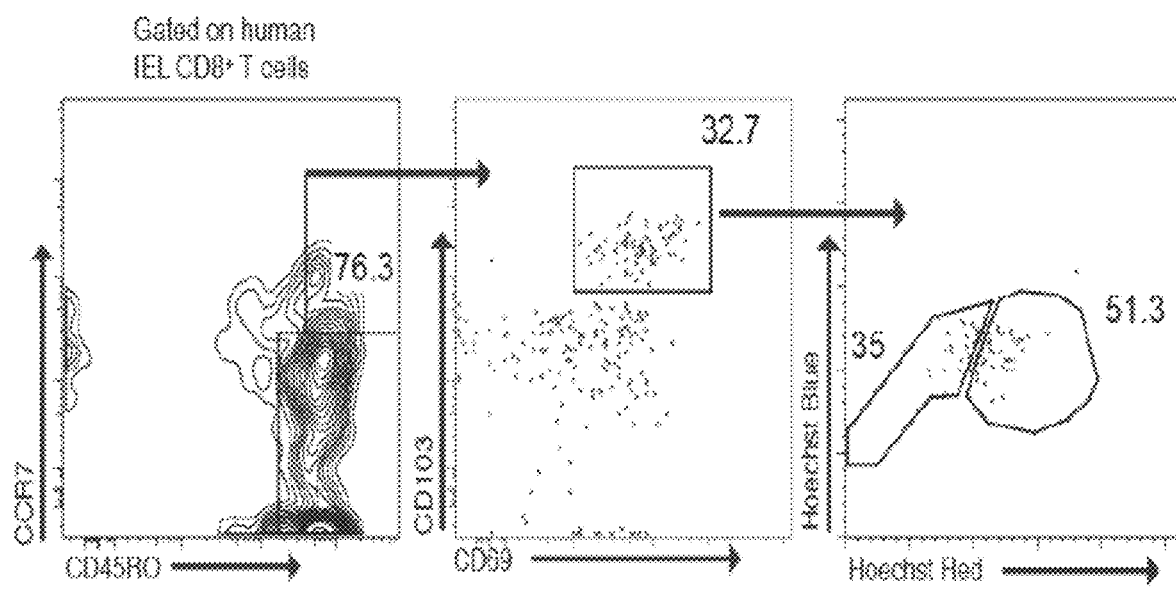

The generation and tissue localization of murine CD8+ memory $T_{SP}$ cells was evaluated using a lymphocytic choriomeningitis virus (LCMV) infection model. Thy1.1+P14+ CD8+ T cells were transferred into naïve B6 mice and analyzed at different time points following LCMV infection. $T_{SP}$ CD8+ T cells were initially detected in the lymphoid tissues at day 8 following infection, but declined by day 30 (FIG. 9A). In contrast, enrichment of $T_{SP}$ cells was detected in the bone marrow up to 60 days following infection (FIG. 9A). Detailed analysis of tissues at 30 days following infection revealed that $T_{SP}$ cells were enriched within the bone marrow, liver and the gut, but not the spleen (FIG. 9B). Interestingly, P14+ CD8 $T_{SP}$ cells were mostly confined to CD69+ T cells in the liver and CD69+CD103+ T cells in Peyer's patches (PP), IEL and lamina propria lymphocytes (LPL) (FIG. 9C). Enrichment of $T_{SP}$ cells was also documented within gp33-tetramer+ T cells in the gut (FIGS. 2A-2B) and the majority of gut-resident $T_{SP}$ cells were enriched for $T_{RM}$ phenotype (CD69+CD103+) (FIGS. 2C-2D). In accordance with this finding, similar enrichment of CD8 $T_{SP}$ cells in human gut $T_{RM}$ cells was also observed (FIG. 9D). Taken together these data show that antigen-specific murine $T_{SP}$ memory CD8 T cells emerge at an early stage of immune response and progressively accumulate in the mucosal tissues enriched for $T_{RM}$ phenotype.

Example 3: Slow Cycling Phenotype of Human and Murine $T_{SP}$ Cells

Figure 3A:
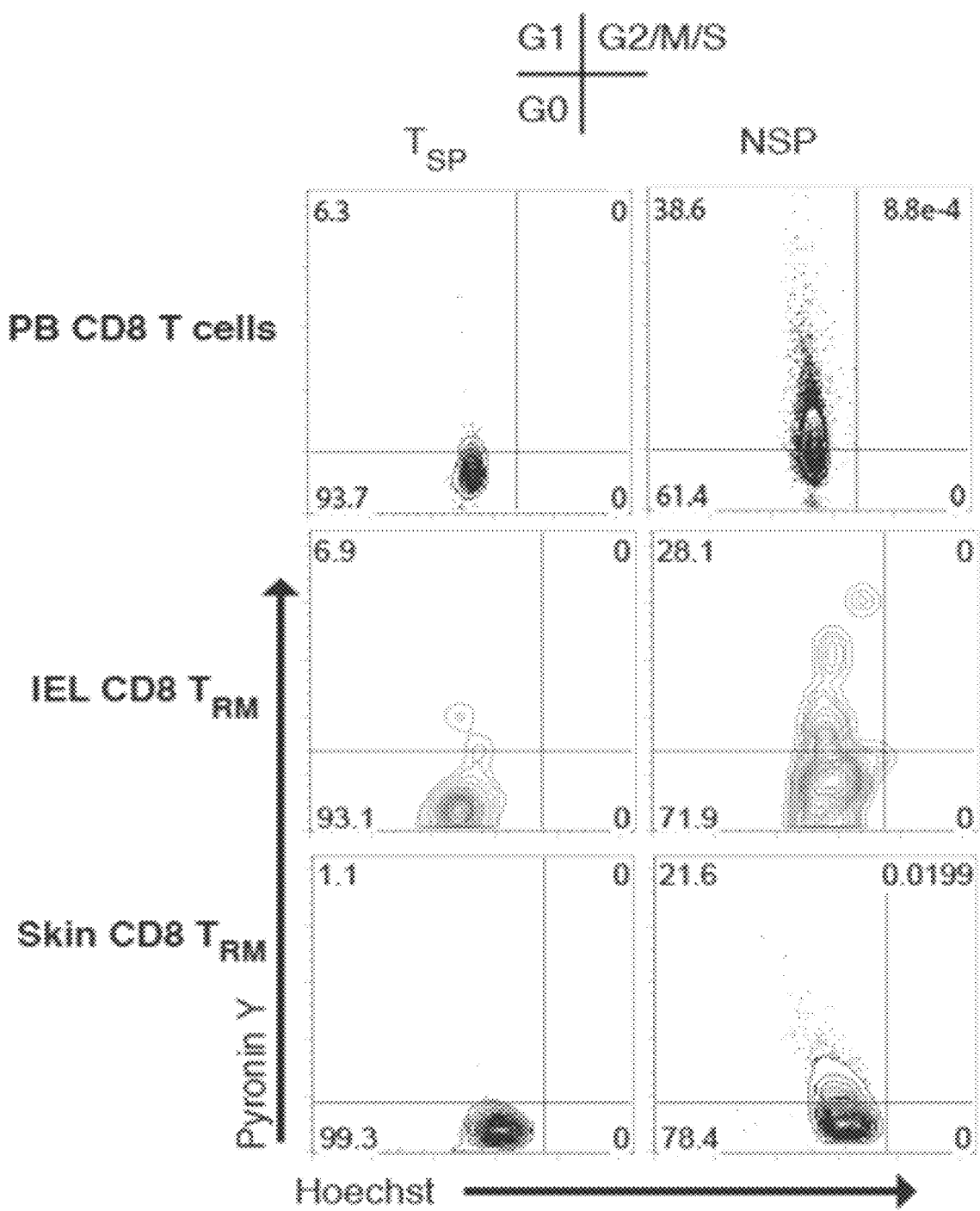
FIGS. 3A-3G are a series of graphs and images showing cell cycle analysis of $T_{SP}$ cells.
Figure 3B:
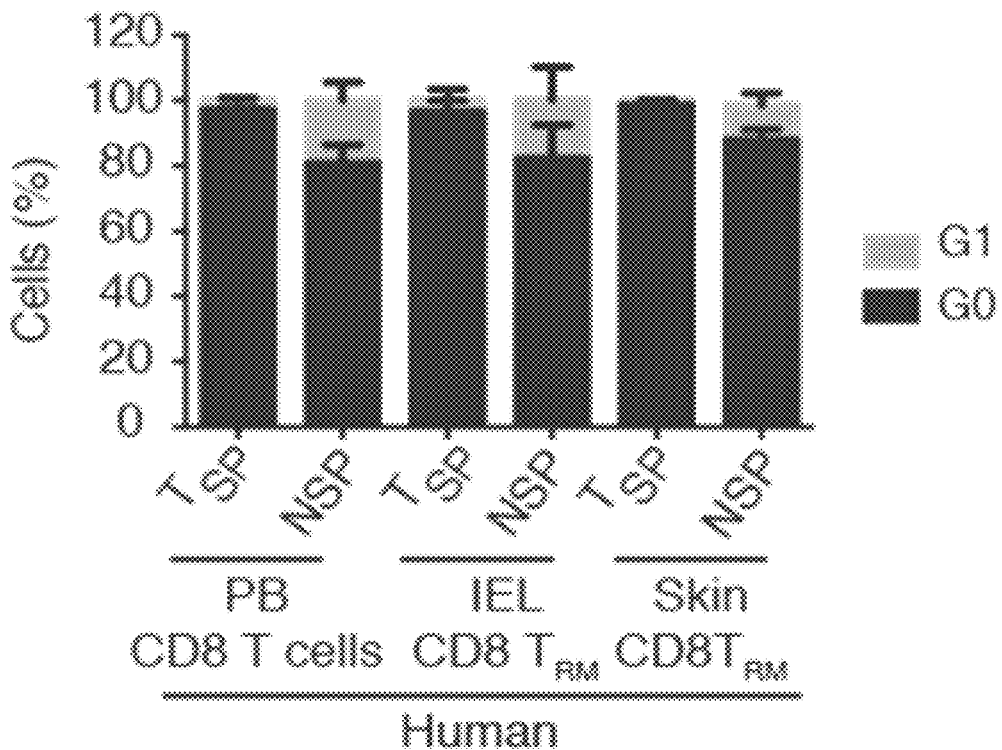
Figure 3C:
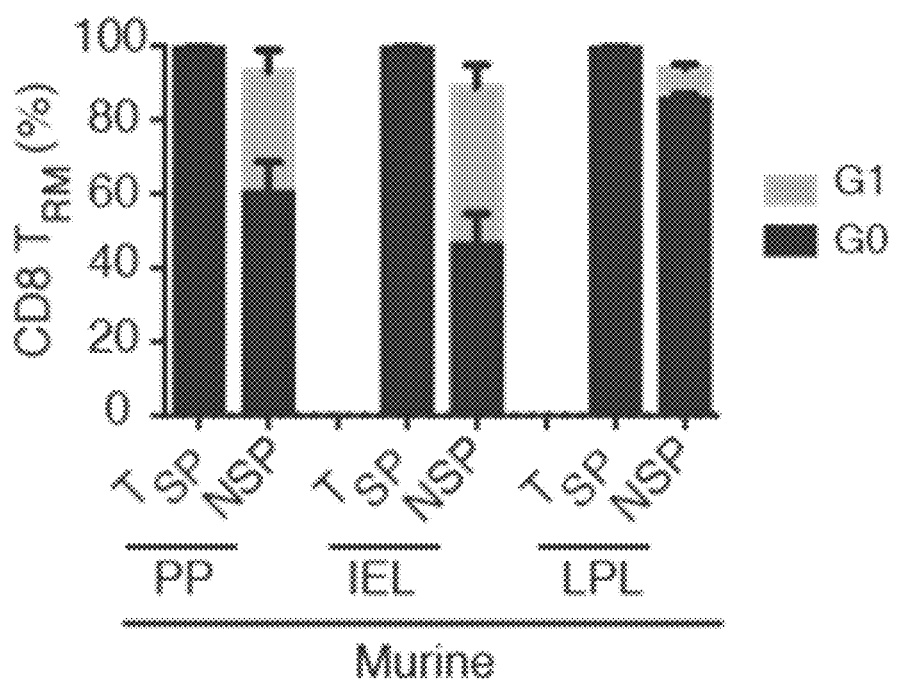

In order to ascertain whether $T_{SP}$ cells represent a functionally distinct subset of human/murine T cells, their cell cycle status was compared with NSP counterparts. SP phenotype cells in hematopoietic stem cells and adult tissue stem cells are characterized as being in a non-cycling state (G0 phase) of the cell cycle (Liu et al. *Cell stem cell.* 2009; 4(1):37-48). Nearly all of the CD4+ and CD8+ $T_{SP}$ cells in human PBMCs were enriched in G0 phase of cell cycle compared to NSP cells based on Hoechst and Pyronin Y staining (FIGS. 3A-3B). As with circulating human $T_{SP}$ cells, those in the bone marrow were also predominantly in the G0 stage of the cell cycle. Importantly, the CD8 $T_{SP}$ subset of $T_{RM}$ cells from human gut and skin were also enriched in G0 phase of cell cycle compared to CD8 NSP $T_{RM}$ cells within these tissues (FIGS. 3A-3B). This low-cycling phenotype of $T_{SP}$ cells was also observed within murine $T_{RM}$ cells. At 35 days following LCMV infection, nearly all GP33-tetramer+ CD8+ $T_{RM}$ cells with $T_{SP}$ phenotype in PP, IEL and LPL were in G0, while NSP counterparts were in both G0 and G1 phases of cell cycle (FIG. 3C).

Figure 3D:
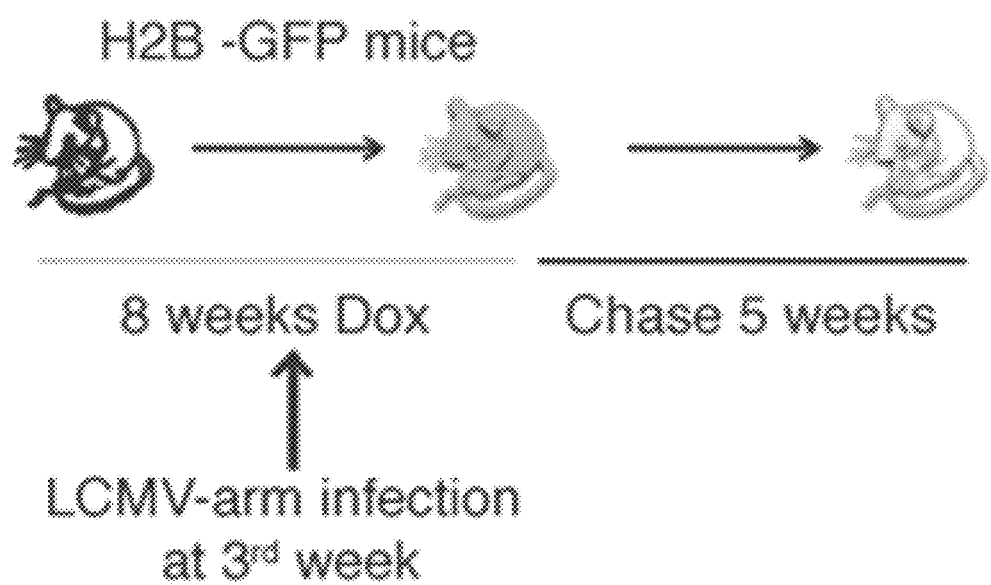
Figure 3E:
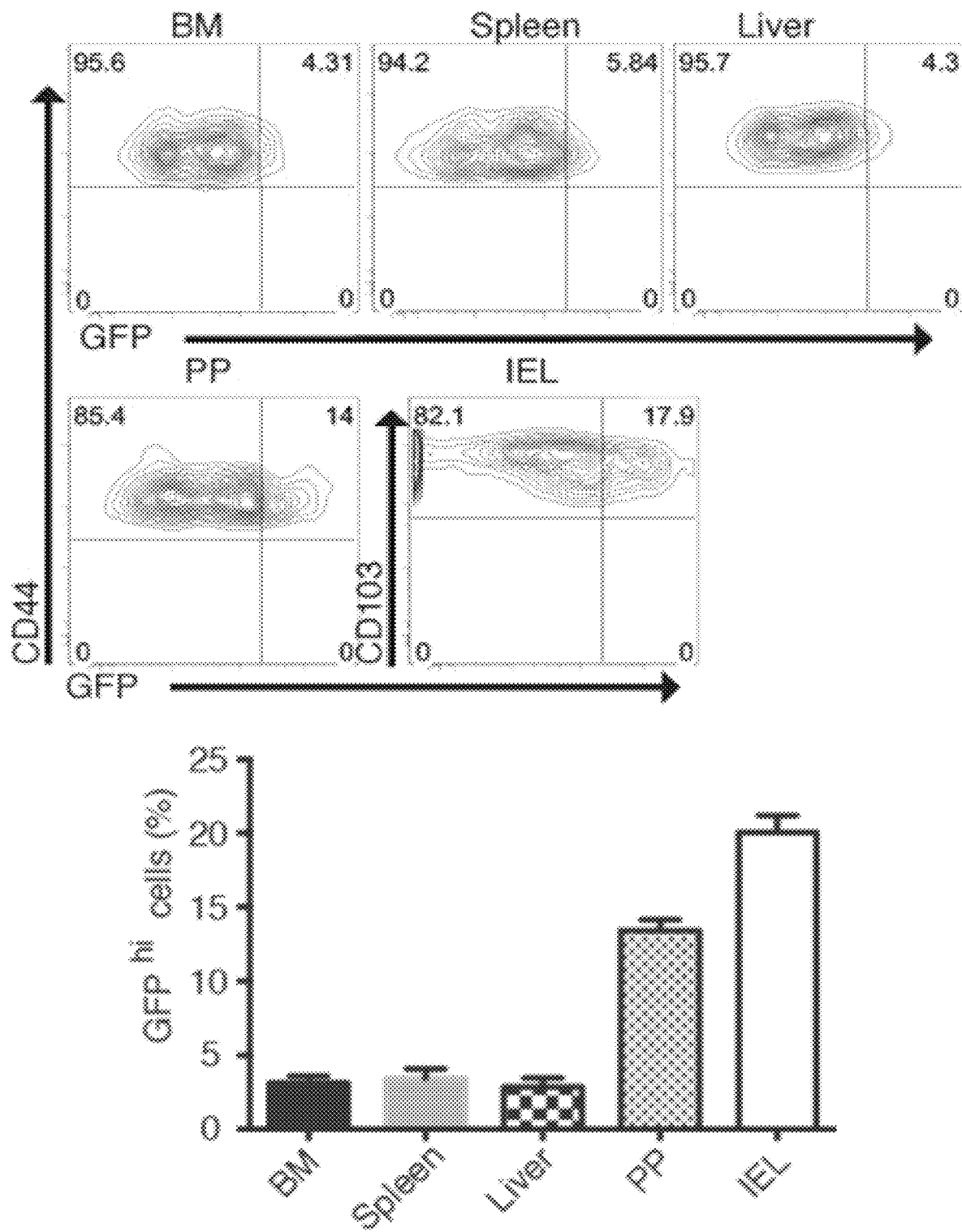
Figure 3F:
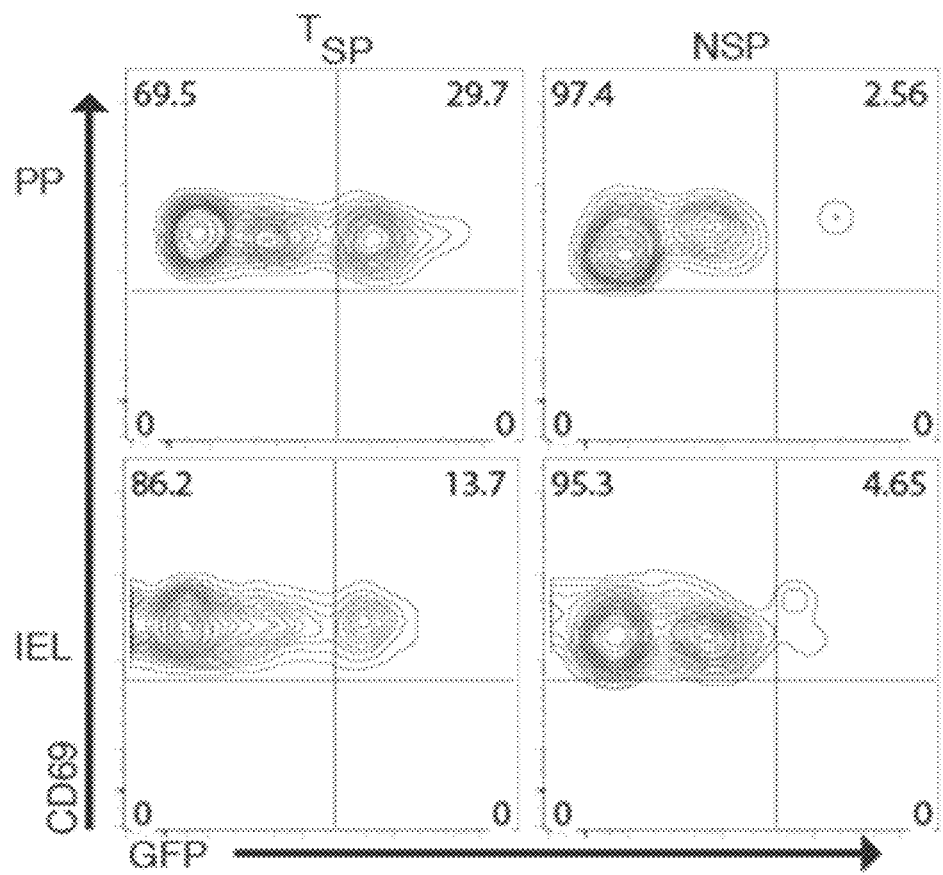
Figure 3G:
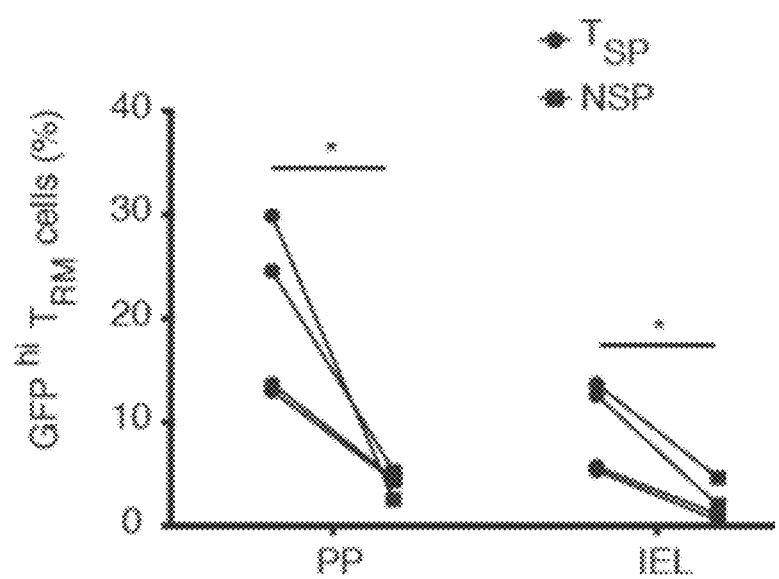
Figure 10A:
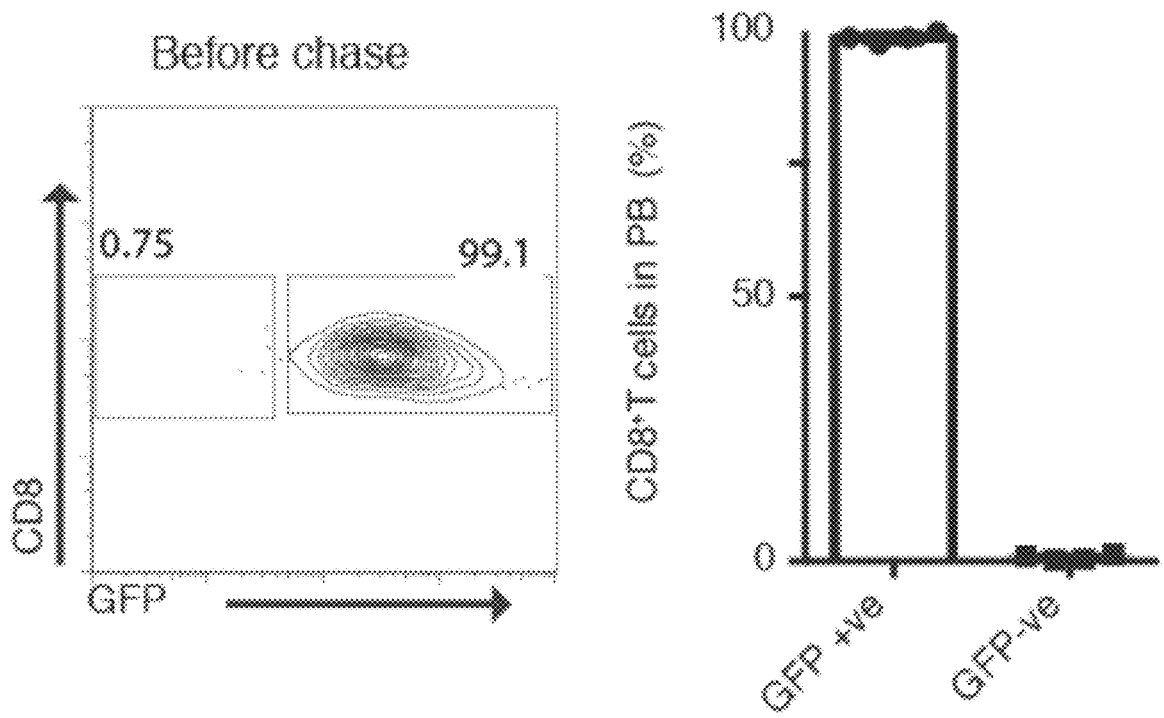
FIGS. 10A-10C are a series of graphs showing H2B GFP label retention analysis.
Figure 10B:
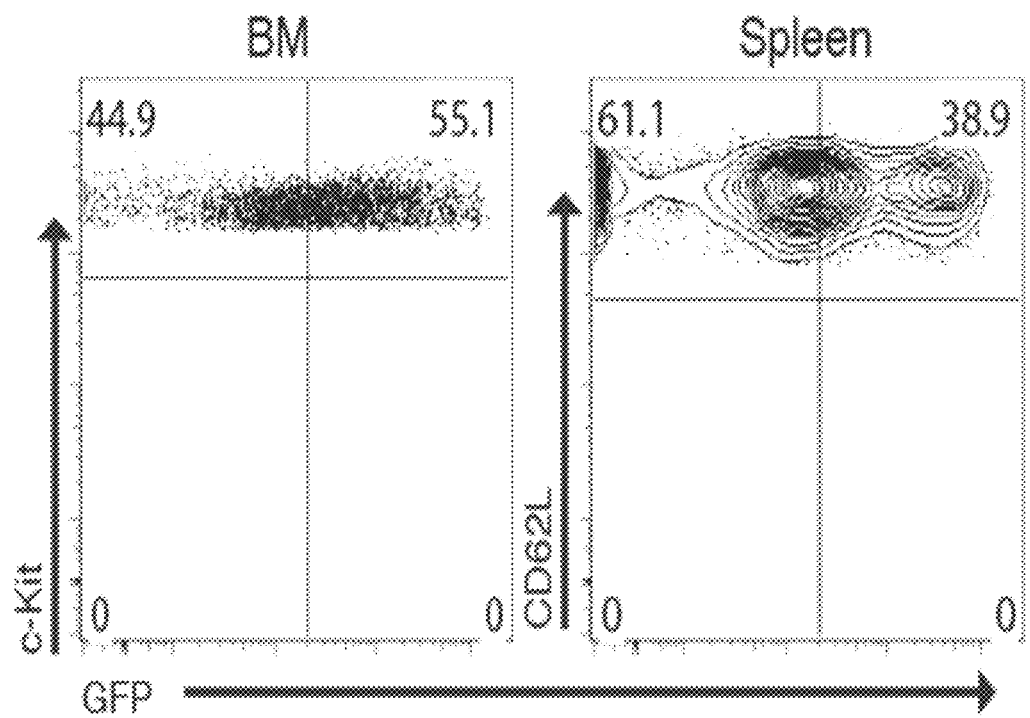
Figure 10C:
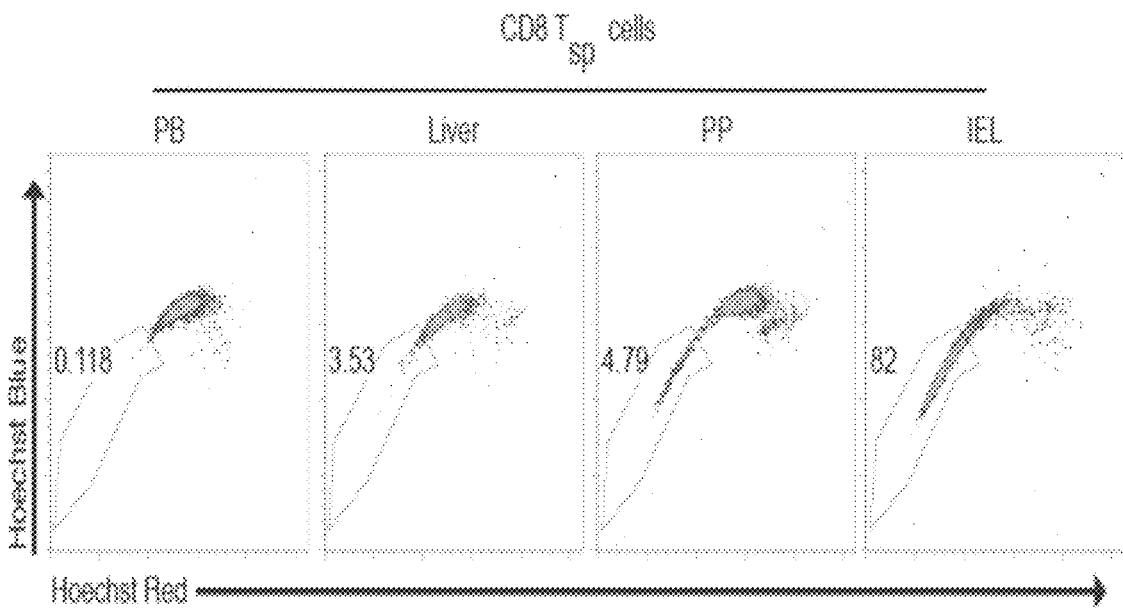

Pyronin-Y staining represents only a snapshot of cycling status. Label retention in doxycycline (Dox)-inducible histone H2B GFP mice has been utilized to identify quiescent/slow cycling populations of stem cells in adult tissues (Foudi et al. *Nat Biotechnol.* 2009; 27(1):84-90; Wilson et al. *Cell.* 2008; 135(6):1118-29), but is not yet comparably applied for the evaluation of quiescent compartment of murine memory T cells in vivo. Mice fed with Dox for 2 weeks were infected with LCMV in the presence of Dox for up to 6 weeks post infection and subsequently a 5 weeks chase was performed by removal of Dox treatment (FIG. 3D). Uniform labeling of $CD8^+$ T cells expressing GFP prior to chase was verified by flow cytometry (FIG. 10A). This strategy revealed that the majority of the lymphoid memory $CD8^+$ T cells in the spleen, liver or bone marrow have undergone cycling and are GFP$^-$ with very few GFP label retaining $CD8^+$ T cells (FIG. 3E). In contrast label retaining $CD8^+$ memory T cells could be detected in the PP and IEL (FIG. 3E). Also, higher percentages of GFP label retaining cells were found in the c-Kit$^+$ stem and progenitor cells in the bone marrow, as well as naïve CD8 T cells in the spleen (FIG. 10B). As $T_{SP}$ cells were particularly enriched within the $CD8^+$ gut $T_{RM}$ cells, the proportion of label retaining cells at the end of a 5 weeks chase within the $T_{SP}$ or NSP compartment of PP or IEL $T_{RM}$ cells was analyzed. SP $CD8^+$ $T_{RM}$ cells from PP and IEL had significantly higher proportions of label retaining cells compared to NSP cells (FIGS. 3F-3G). In contrast to murine tissues and human blood, $T_{SP}$ cells in murine blood were not detected (FIG. 10C). Together these data identify a distinct slow-cycling compartment within gut $T_{RM}$ cells and demonstrate that the $T_{SP}$ phenotype identifies a functionally distinct subset of human/murine T cells with a slow-cycling phenotype within the $T_{RM}$ compartment.

Example 4: Distinct Gene Expression Profile in Human $CD8^+$ $T_{SP}$ Cells

Figure 4A:
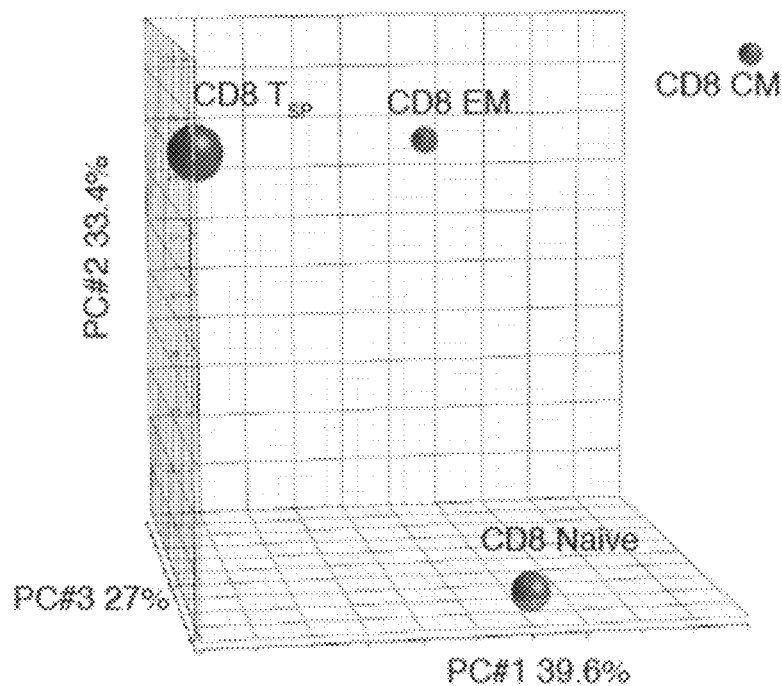
FIGS. 4A-4D are a series of plots and diagrams showing human CD8 $T_{SP}$ cells express a distinct gene expression profile.
Figure 4B:
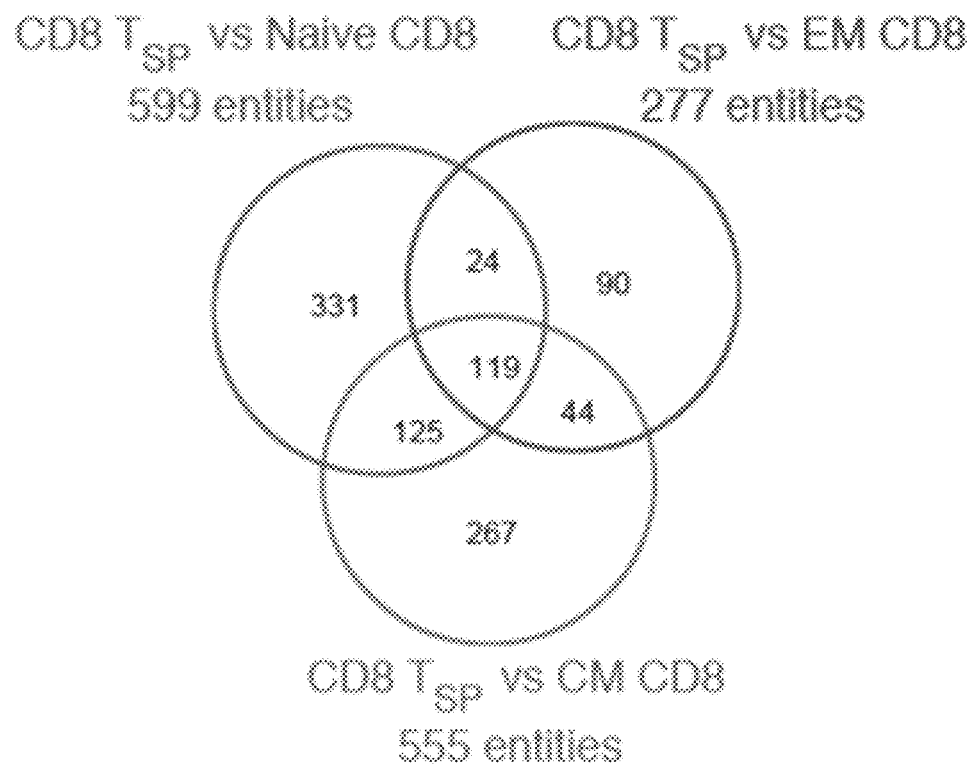
Figure 4C:
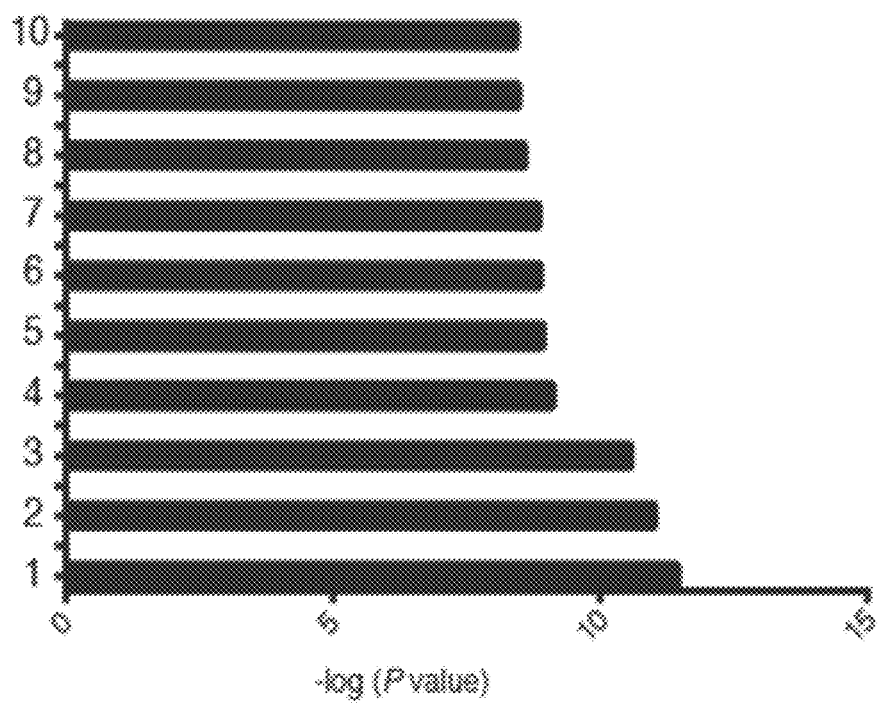
Figure 4D:
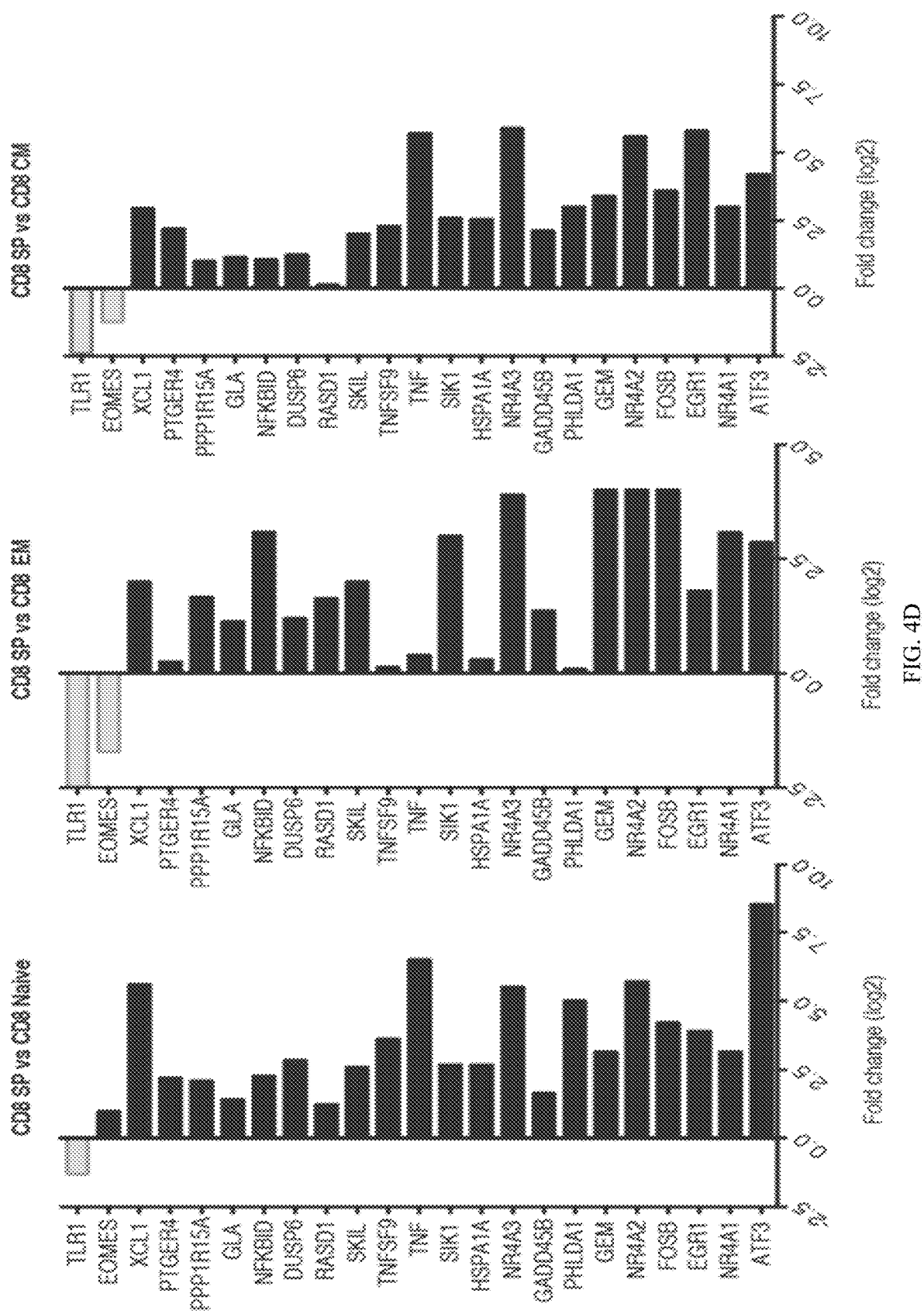
Figure 11:
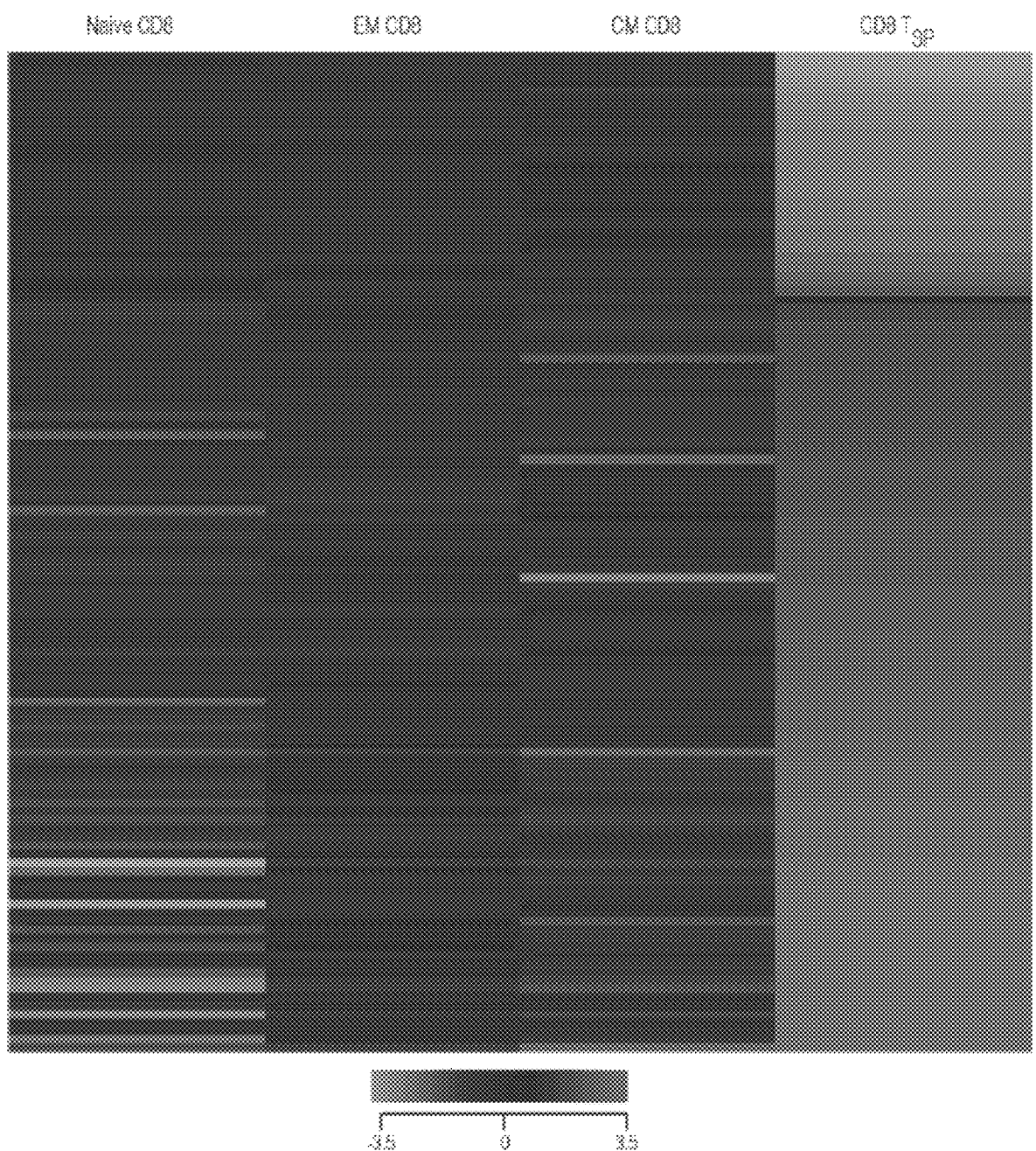
FIG. 11 is a heat map comparing the gene expression profile of $T_{SP}$ versus other T cell subsets. The heat map shows differentially expressed genes between $CD8^+ T_{SP}$ and nave, EM and CM (Fold change >4).

In order to better understand the functional properties of $T_{SP}$ cells, the transcriptome of purified human $CD8^+$ $T_{SP}$ cells was compared to $CD8^+$ naïve, T central memory ($T_{CM}$) and T effector memory ($T_{EM}$) cells isolated from the same donor. Principal component analysis revealed that $T_{SP}$ cells had a distinct gene expression profile more closely related to $T_{EM}$ $CD8^+$ T cells than $T_{CM}$ or naïve CD8 T cells (FIG. 4A, FIG. 11). Discriminant analysis for genes differentially regulated within the CD8 $T_{SP}$ compartment as compared to other CD8 T cell subsets identified 119 transcripts that formed the core $CD8^+$ $T_{SP}$ signature (FIG. 4B, FIG. 11). Metacore pathway analysis for GO terms revealed that the top $T_{SP}$-signature related pathways were metabolic regulation and cell cycle (FIG. 4C). Similar analysis for $CD4^+$ $T_{SP}$ cells revealed that the genes overexpressed within $CD4^+$ $T_{SP}$ cells are highly overlapping with those in $CD8^+$ $T_{SP}$ cells. Several of the genes overexpressed in $T_{SP}$ cells are associated with $T_{RM}$ cells and genes comprising the recently described core signature of human skin $T_{RM}$ cells (Li et al. *PLoS One*. 2016; 11(1):e0148351) were increased in CD8 $T_{SP}$ cells compared to naïve, $CD8^+$ $T_{EM}$ and $T_{CM}$ counterparts (FIG. 4D). This core human CD8 $T_{SP}$ signature included XCL1, SKIL, SIK1 and several members of nuclear hormone family of transcription factors NR4A1 (Nur77), NR4A2 and NR4A3, which are also overlapping with the genomic signature of murine $CD8^+$ $T_{RM}$ cells (Mackay et al. *Nat Immunol*. 2013; 14(12):1294-301)(FIG. 4D). Shared enrichment of NR4A and ABC transporters in $T_{SP}$ and $T_{RM}$ cells led to the hypothesis that these genes may play an important role in the biology of $T_{RM}$ cells.

Example 5: Impact of Nur77 on $CD8^+$ $T_{RM}$ Cells

Figure 5A:
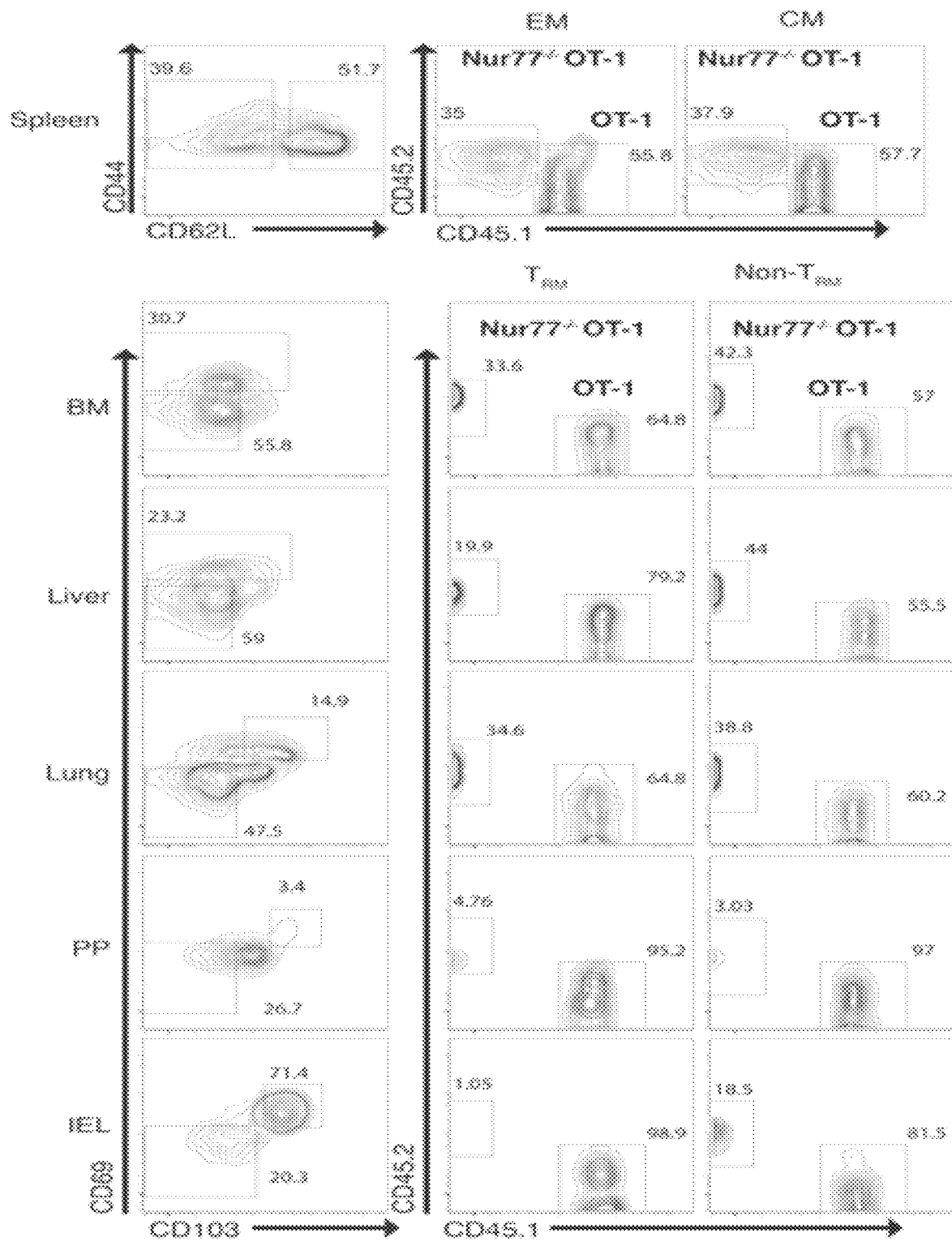
FIGS. 5A-5B are a series of graphs showing the impact of Nur77 on CD8$^+$ $T_{RM}$ cells. Flow cytometry on Vα2 CD8$^+$ T cells obtained from chimeras generated by reconstitution of wild-type mice with 1:1 mixture of WT OT-1 and Nur77$^{-/-}$ OT-1 cells and then assessed at day 35 after infection with flu X-31 ova.
Figure 5B:
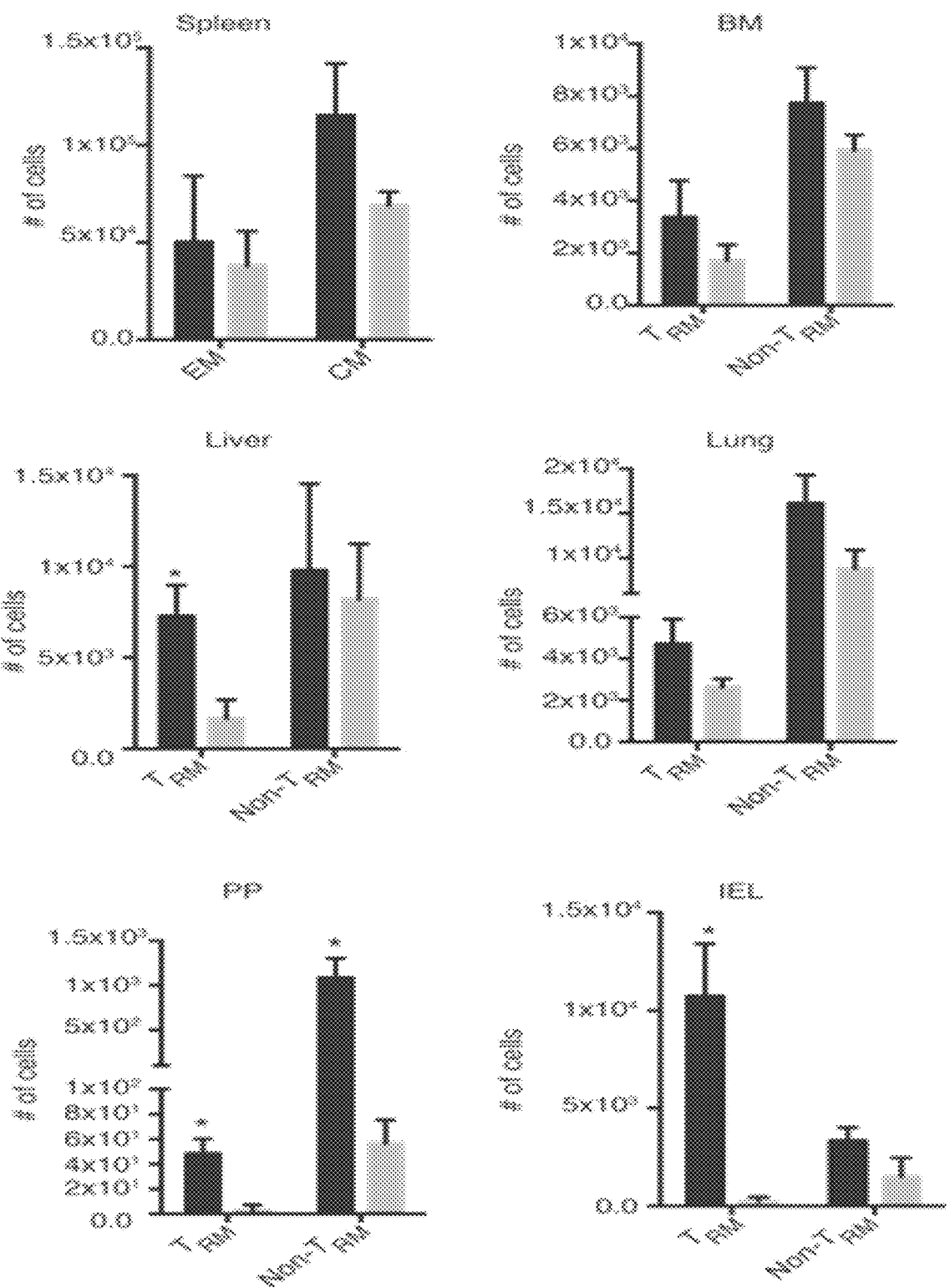
Figure 12A:
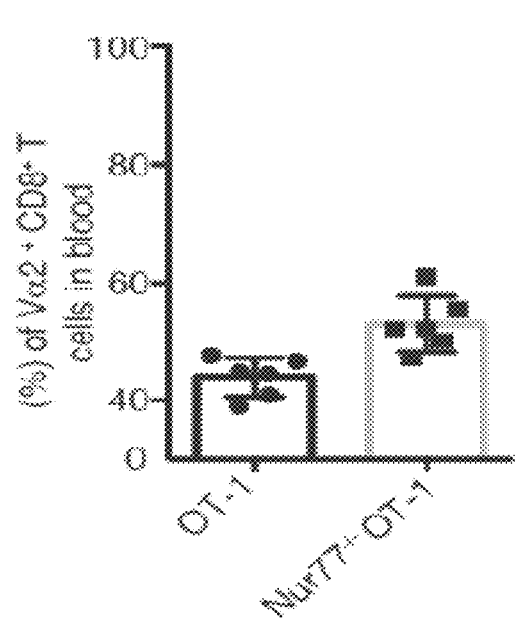
FIGS. 12A-12B show results from analysis of Flu-ova infected mice.
Figure 12B:
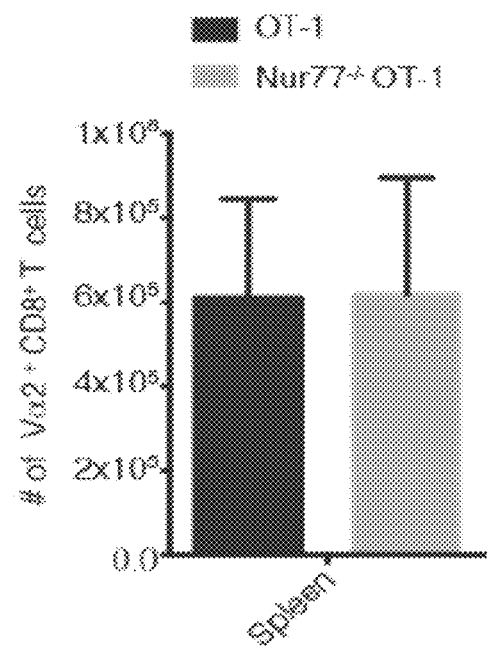

The NR4A family of transcription factors is implicated in the regulation of T cell development as well as quiescence of hematopoietic stem cells (HSCs), including the subset of HSCs with side population phenotype (Land et al. *Stem Cells*. 2015; 33(1):278-88; Sirin et al. *Nat Cell Biol*. 2010; 12(12):1213-9; Sekiya et al. *Nat Immunol*. 2013; 14(3):230-7; Winoto et al. *Cell*. 2002; 109 Suppl(S57-66)). As these genes also appear to be specifically overexpressed in $T_{SP}$ and $T_{RM}$ cells, the role of Nur77 in the generation of $T_{RM}$ cells was analyzed using adoptive transfer of Nur-77 deficient T cells in an influenza infection model. $CD8^+$ T cell chimeras were generated by transferring Vα2 naïve $CD8^+$ cells from CD45.1 wild type (WT)-OT-1 and CD45.2 Nur77$^{-/-}$ OT-1 cells at a 1:1 ratio and these mice were infected with Ova-expressing influenza virus. Both WT and Nur77$^{-/-}$ OT-1 $CD8^+$ T cells expanded comparably in the early (day 8-14) effector phase (FIGS. 12A-12B), but the proportion of Nur77$^{-/-}$ CD8 T cells was reduced by day 35 following infection. Difference between Nur77$^{-/-}$ and WT chimerism was most profound in the $T_{RM}$ compartment of liver, PP and IEL, with minimal effect on non-$T_{RM}$ cells except in the Peyer's patches (FIGS. 5A-5B). Together these data suggest that NR4A1/Nur77 plays an important role in regulating tissue residence of murine CD8 $T_{RM}$ cells.

Example 6: Alterations in Gut $T_{RM}$ Cells in ABC Transporter Deficient Mice

Figure 6A:
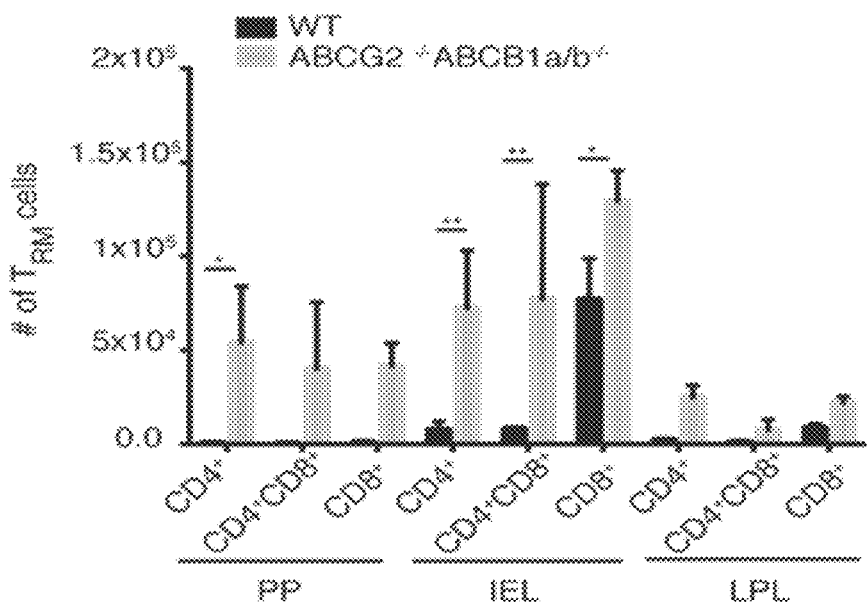
FIGS. 6A-6C are a series of graphs showing ABCG2$^{-/-}$ ABCB1 a/b$^{-/-}$ mice display increased inflammatory $T_{RM}$ compartments.
Figure 6B:
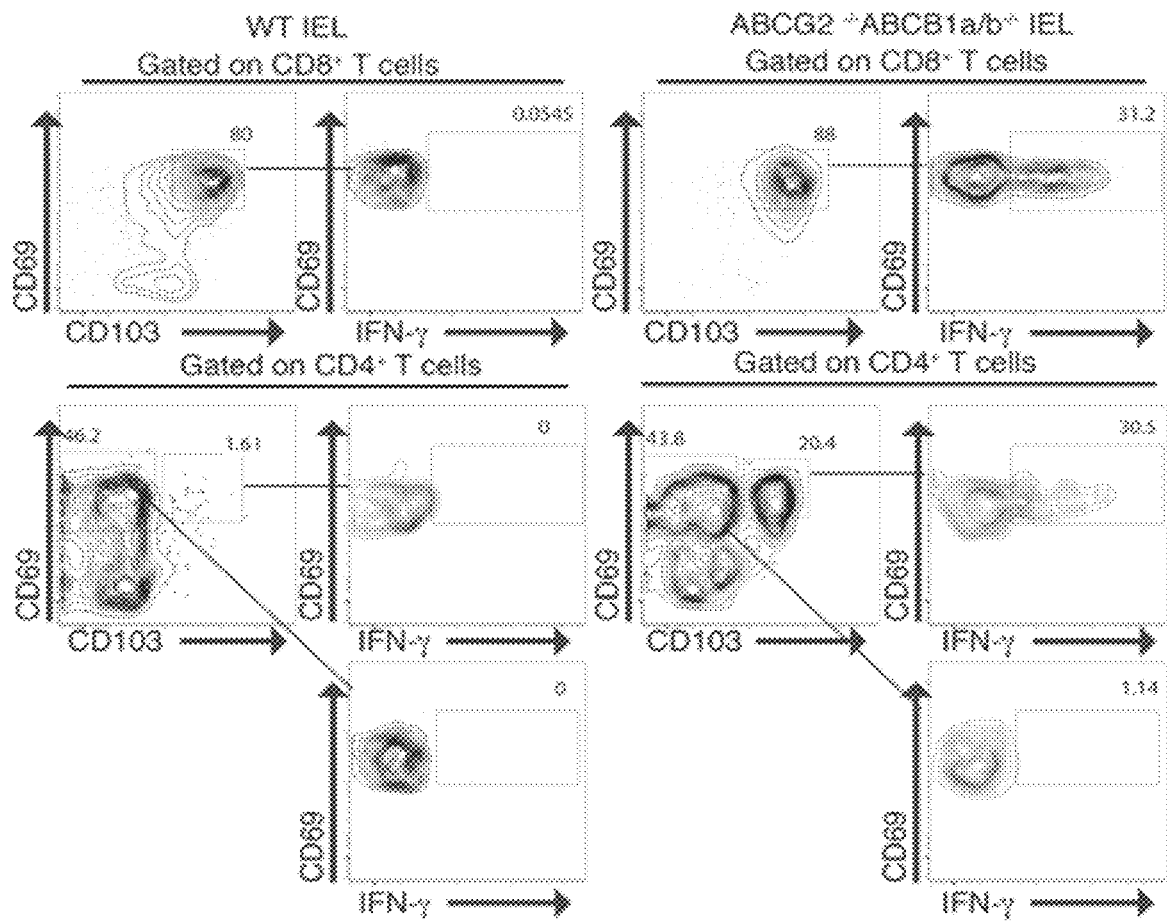
Figure 6C:
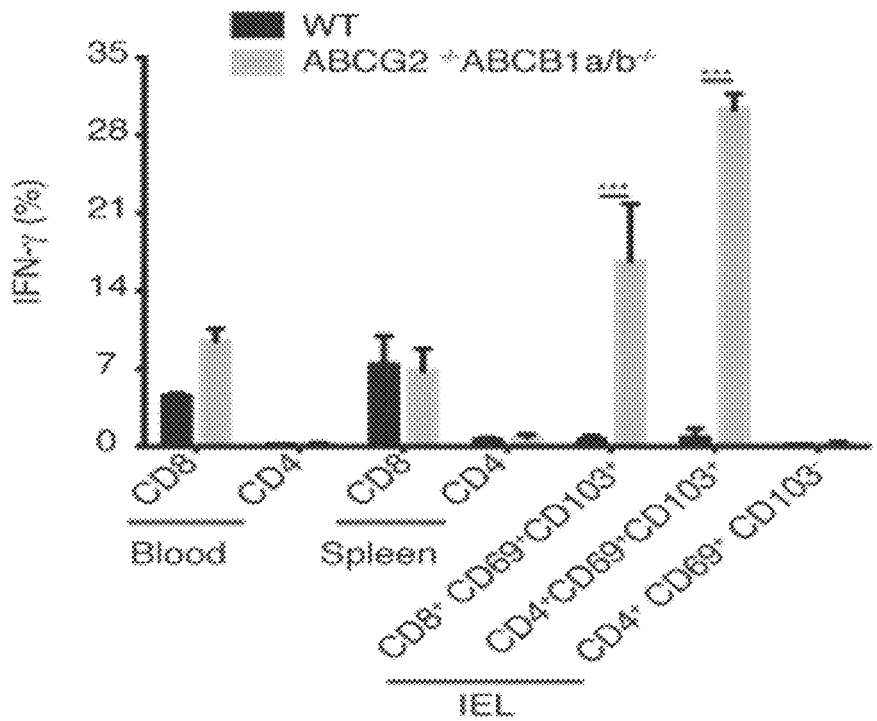
Figure 13A:
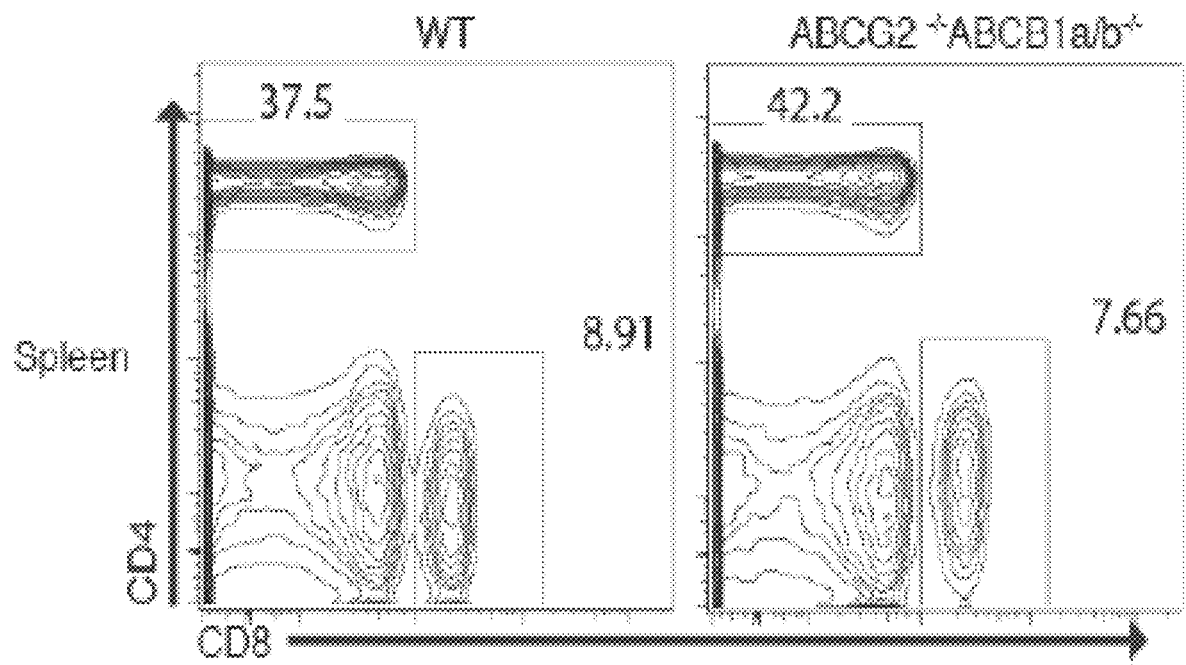
FIGS. 13A-13E are a series of graphs showing results from SP analysis in WT and $ABCG2^{-/-} ABCB1a/b^{-/-}$ mice.
Figure 13B:
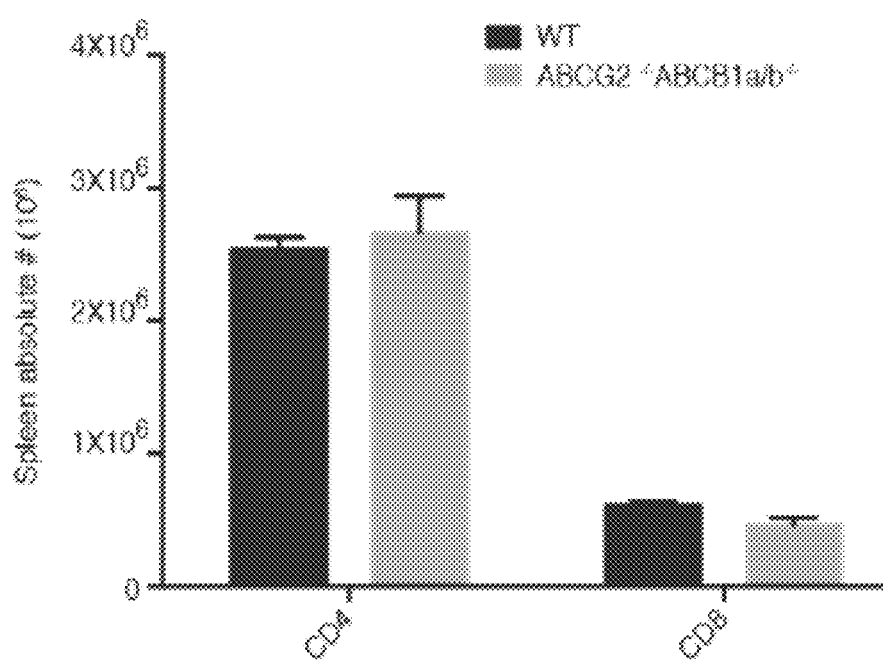
Figure 13C:
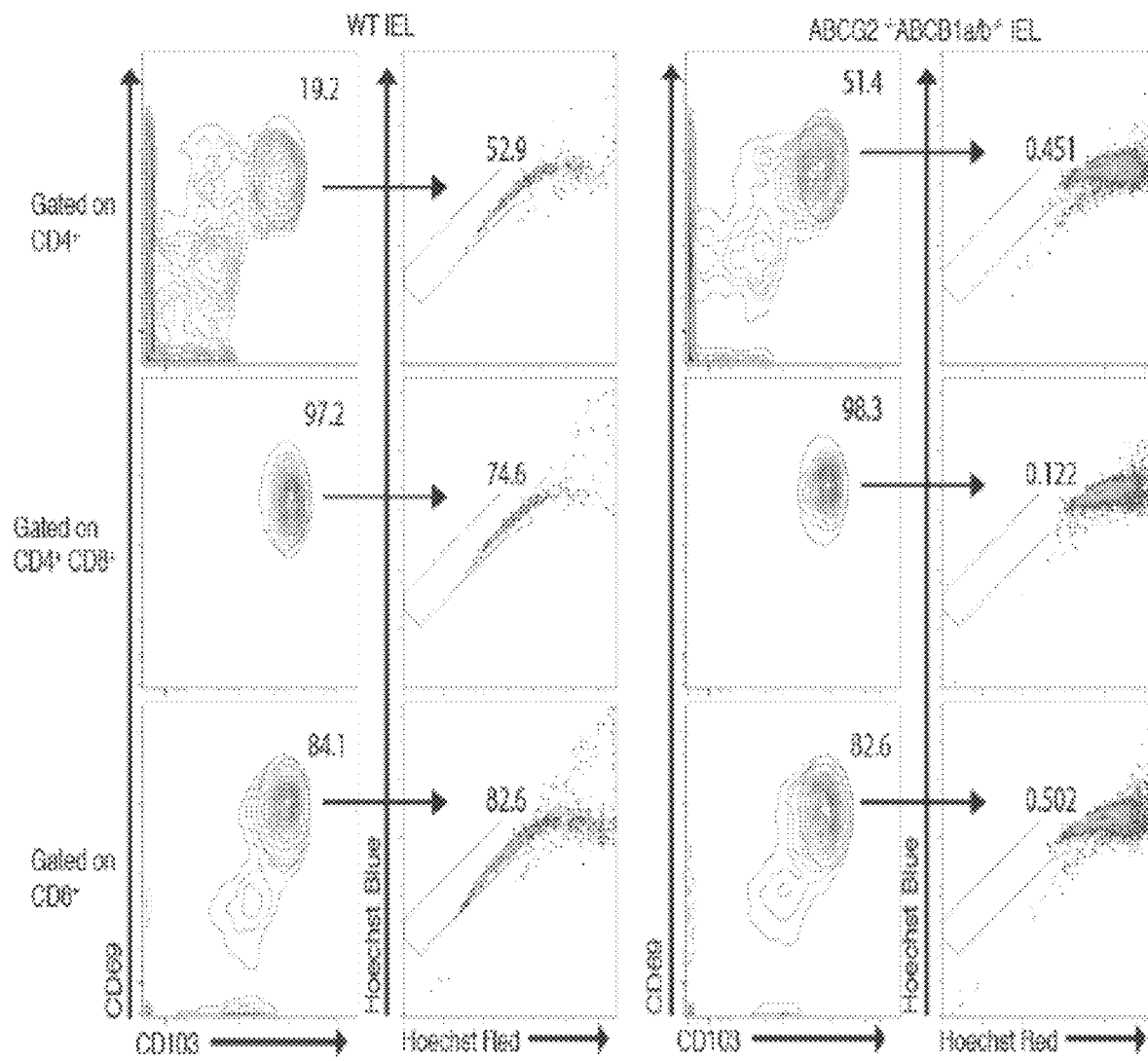
Figure 13D:
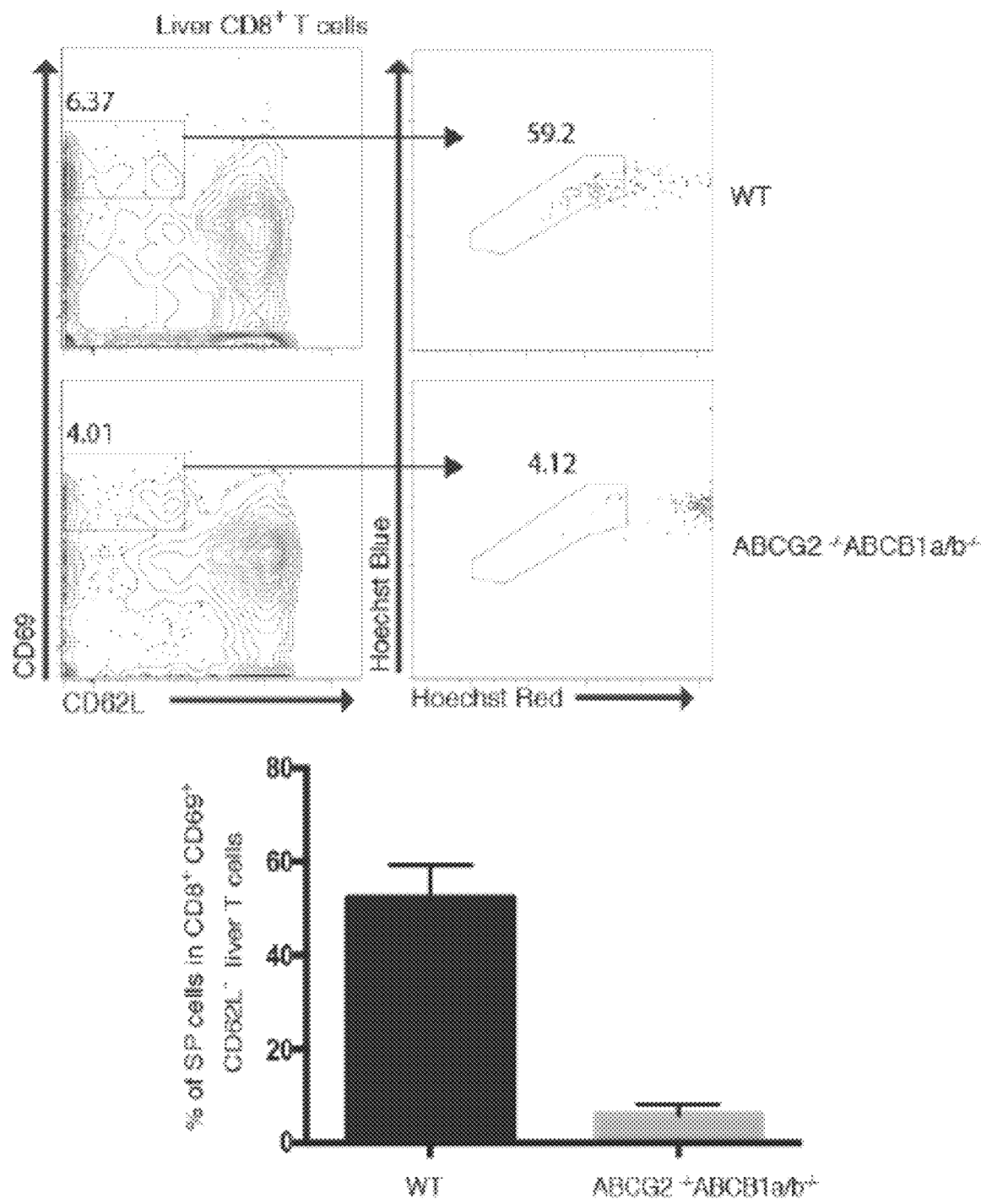
Figure 13E:
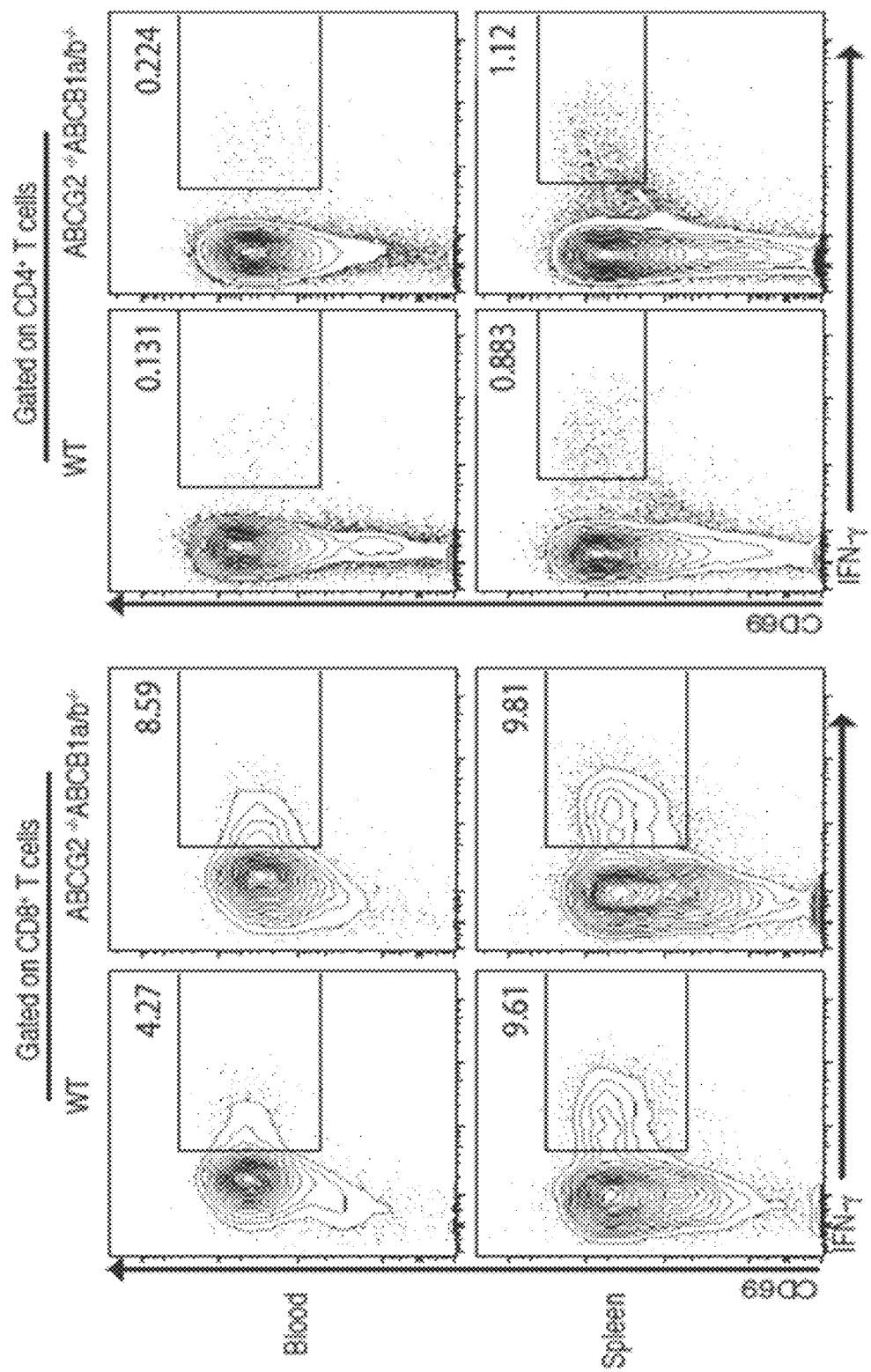

As the $T_{SP}$ phenotype primarily depends on the expression of ATP binding cassette (ABC) transporter family members, ABCB1a/b$^{-/-}$ ABCG2$^{-/-}$ double deficient mice were utilized to evaluate the role of these transporters in $T_{RM}$ biology. As Hoechst dye exclusion depends on these transporters, $T_{SP}$ phenotype cannot be detected in these mice. The hypothesis that lack of transporters may alter the homeostasis/function of $T_{RM}$ cells was tested. Marked increase in $CD4^+$, $CD4^+CD8^+$ and $CD8^+$ $T_{RM}$ cells was observed in the PP and IELs in ABCB1a/b$^{-/-}$ ABCG2$^{-/-}$ mice compared to WT mice, while the number of T cells in the spleen was comparable (FIG. 6A, FIGS. 13A-13B). $T_{RM}$ cells in IEL and liver of ABCB1a/b$^{-/-}$ ABCG2$^{-/-}$ mice lacked the SP phenotype (FIGS. 13C-13D). In order to better understand the differences in functional properties of these T cells, IFN-γ production in IEL $T_{RM}$ cells was compared from these mice. Freshly isolated $CD4^+$ and $CD8^+$ IEL $T_{RM}$ cells (but not blood and splenic T cells) from transporter deficient mice produced much more IFN-γ than those from WT mice (FIGS. 6B-6C). Interestingly, increased IFN-γ production in IELs of transporter-deficient mice was restricted to $CD69^+$ $CD103^+$ cells and not observed in $CD69^+CD103^-$ cells (FIGS. 6B-6C). Together these data demonstrate that ABC transporters may regulate homeostasis and functional properties of $T_{RM}$ cells in the gut.

Example 7: Mobilization and Adoptive Transfer of $T_{SP}$ Cells In Vivo

Figure 7A:
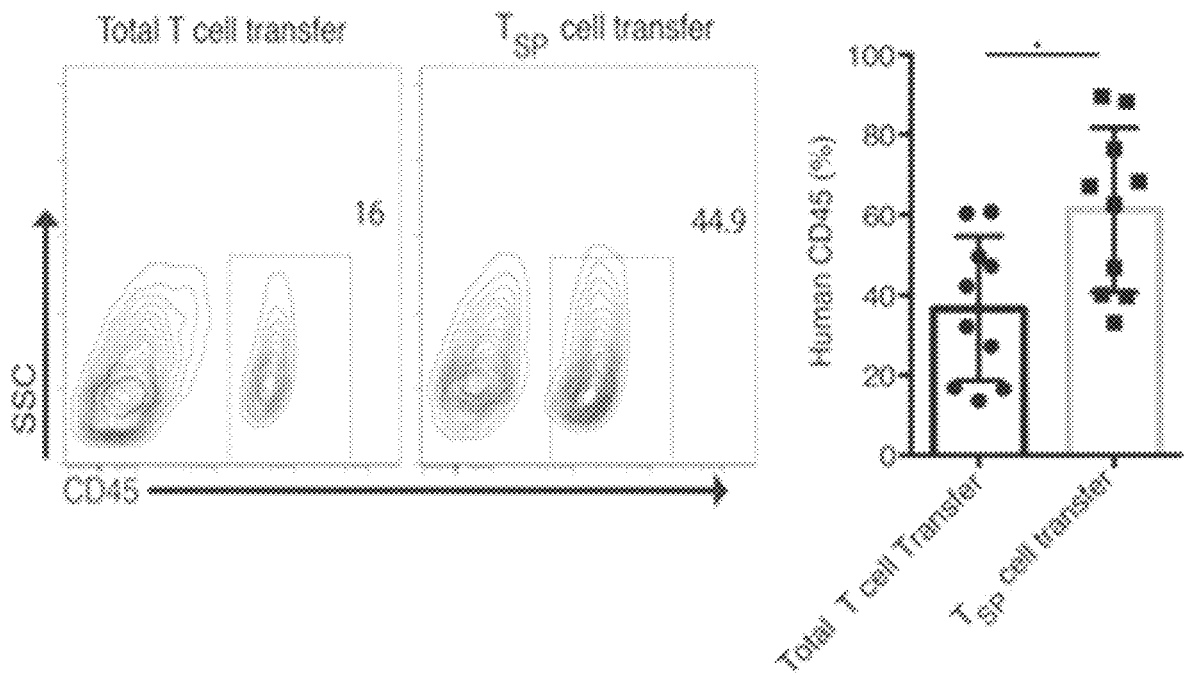
FIGS. 7A-7E are as series of graphs and images showing human $T_{SP}$ cells cause greater tissue pathology following adoptive transfer in mice and can be mobilized into circulation by Plerixafor. Sorted $T_{SP}$ cells and control T cells (total T cells), 100,000 each are retro oribitally transferred in to individual NSG mice and analyzed after 5-6 weeks.
Figure 7B:
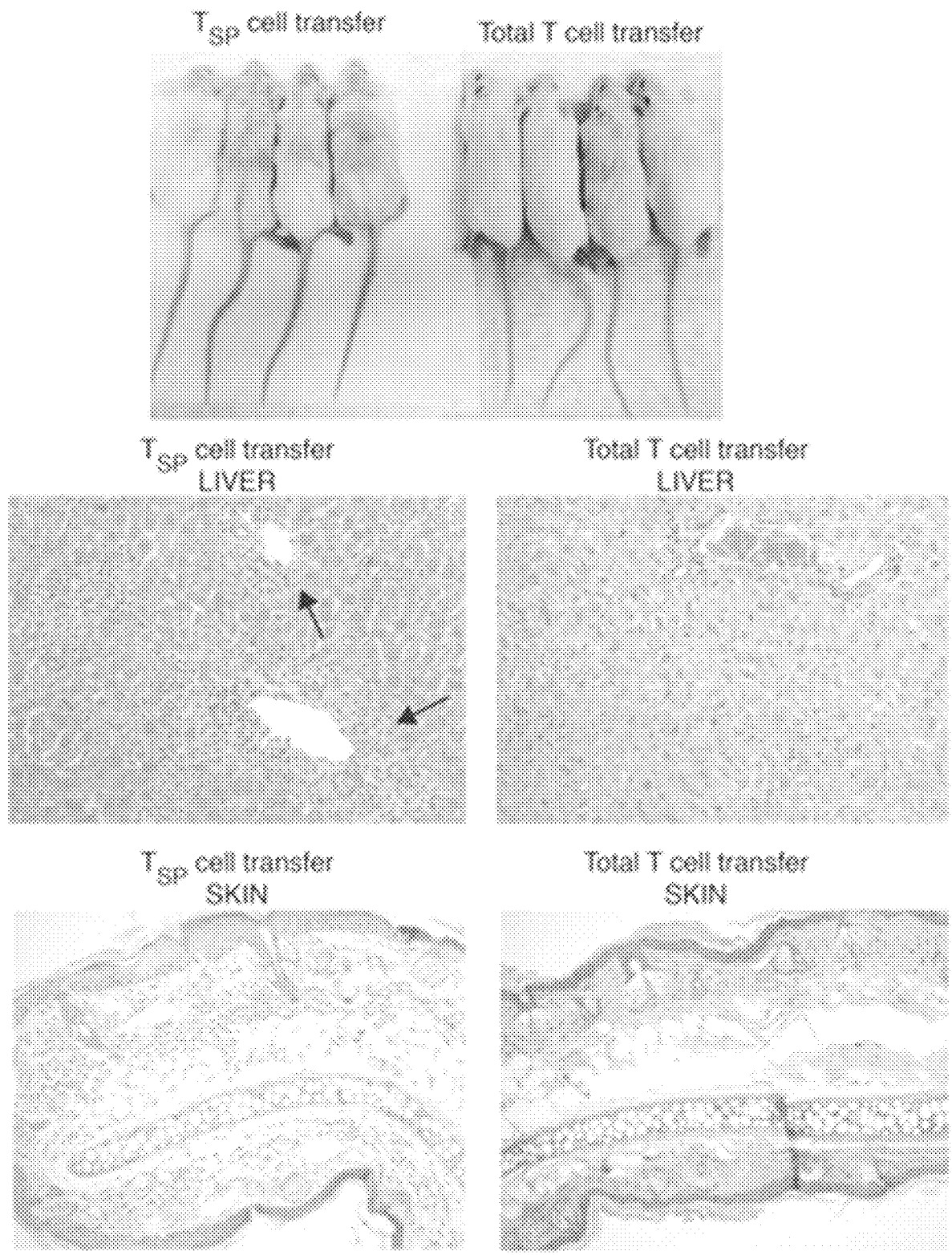
Figure 7C:
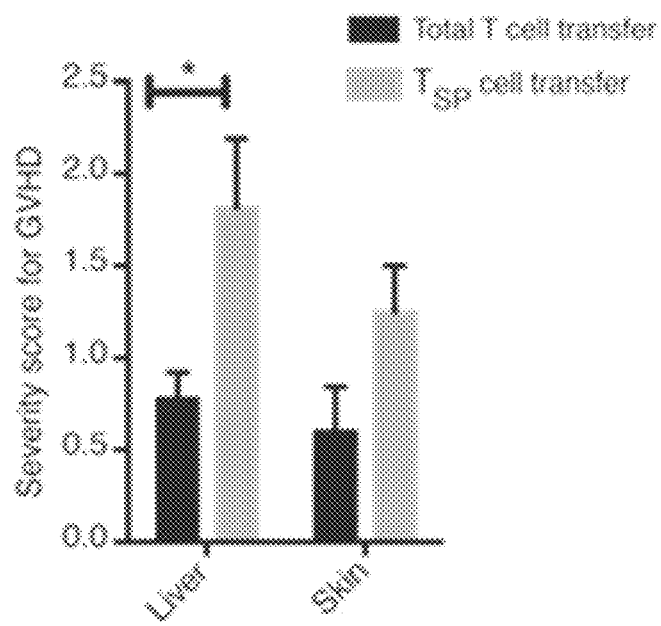

Adoptive transfer of T cells has emerged as a promising therapeutic strategy against human cancer, although there is a need to enhance infiltration and persistence of transferred cells in the tumor tissue, particularly in the setting of solid tumors. The finding that human $T_{SP}$ cells have a quiescent phenotype and shared biology with $T_{RM}$ cells makes them attractive candidates as vehicles for adoptive cellular therapy. The effect of adoptive transfer of human $T_{SP}$ cells in the context of a xeno-GVH model and their mobilization into circulation in patients was explored. In order to evaluate the in vivo proliferative potential and effector function of human $T_{SP}$ cells, sorted human $T_{SP}$ cells and control T cells (total T cells) were adoptively transferred into immune-deficient NOD.Cg-Prkdc$^{scid}$Il2rg$^{tm1Wjl}$/SzJ (NSG) mice. Human T cell engraftment and resultant tissue pathology was analyzed 6 weeks following adoptive transfer. Adoptive transfer of human T$_{SP}$ cells led to greater engraftment of human CD45$^+$ T cells compared to the injection of total T cells (FIG. 7A). This was also associated with greater degree of tissue infiltration (particularly in the liver) and severity score for GVHD (FIGS. 7B-7C).

Figure 7D:
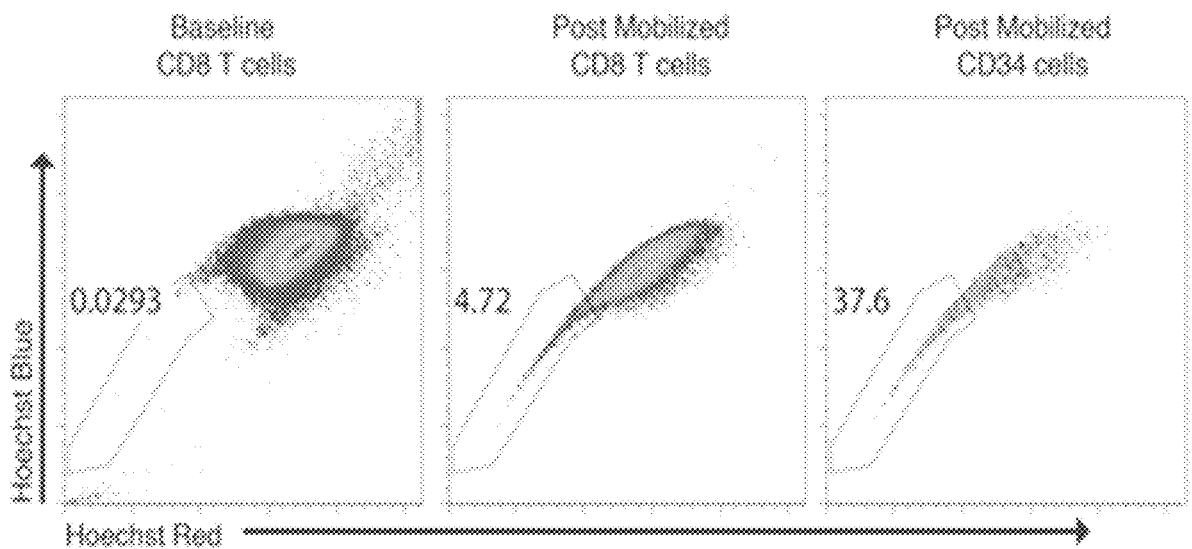
Figure 7E:
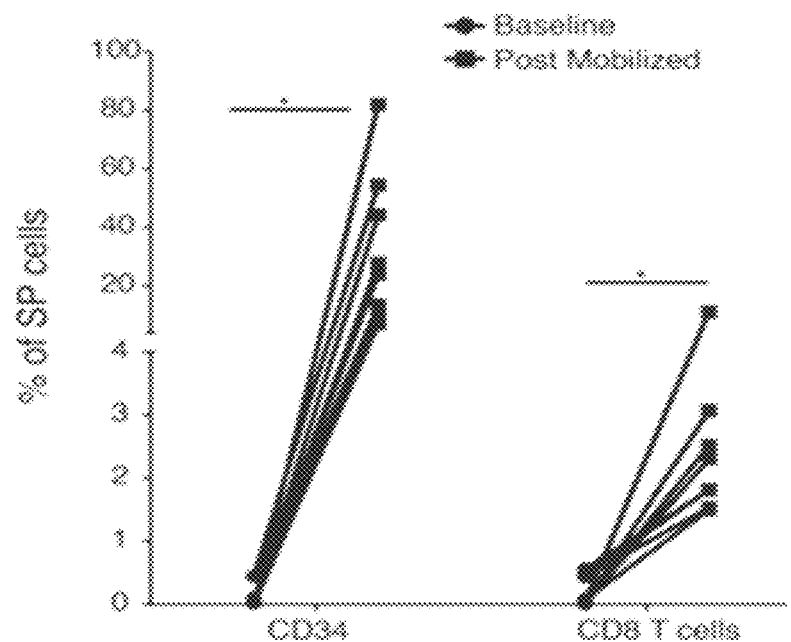
Figure 8A:
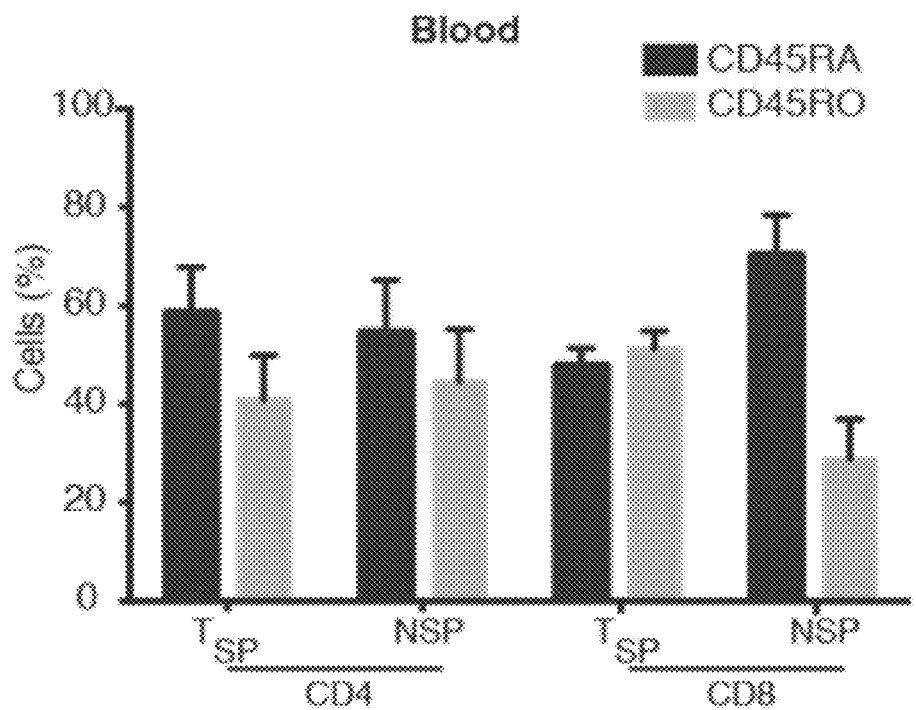
FIGS. 8A-8D are a series of graphs showing the phenotype of $T_{SP}$ and NSP cells from human blood, BM and skin.
Figure 8B:
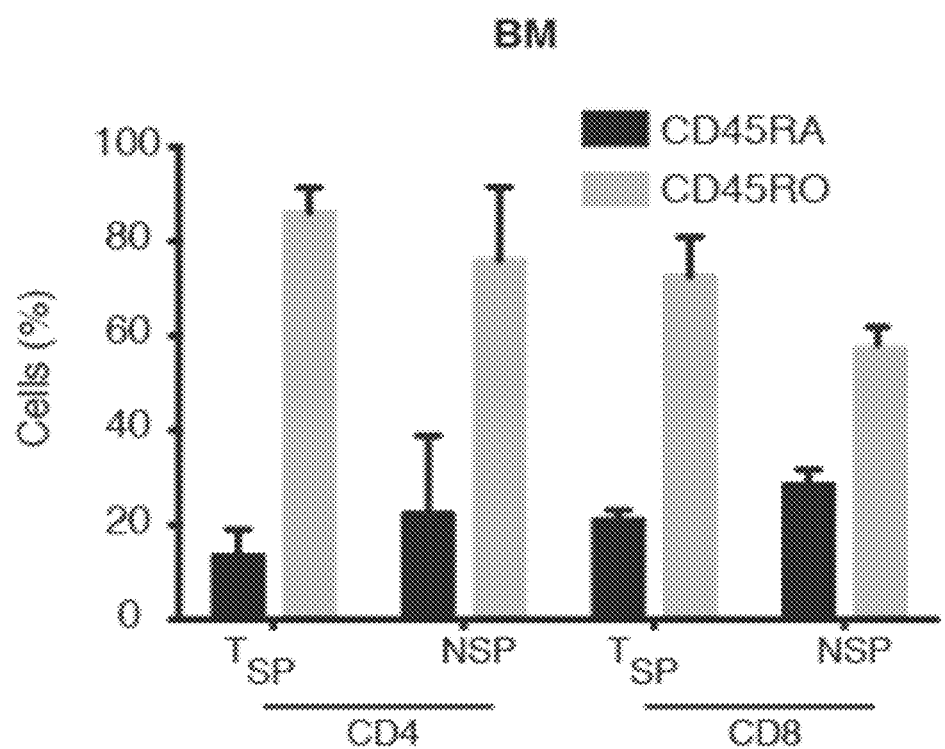
Figure 8C:
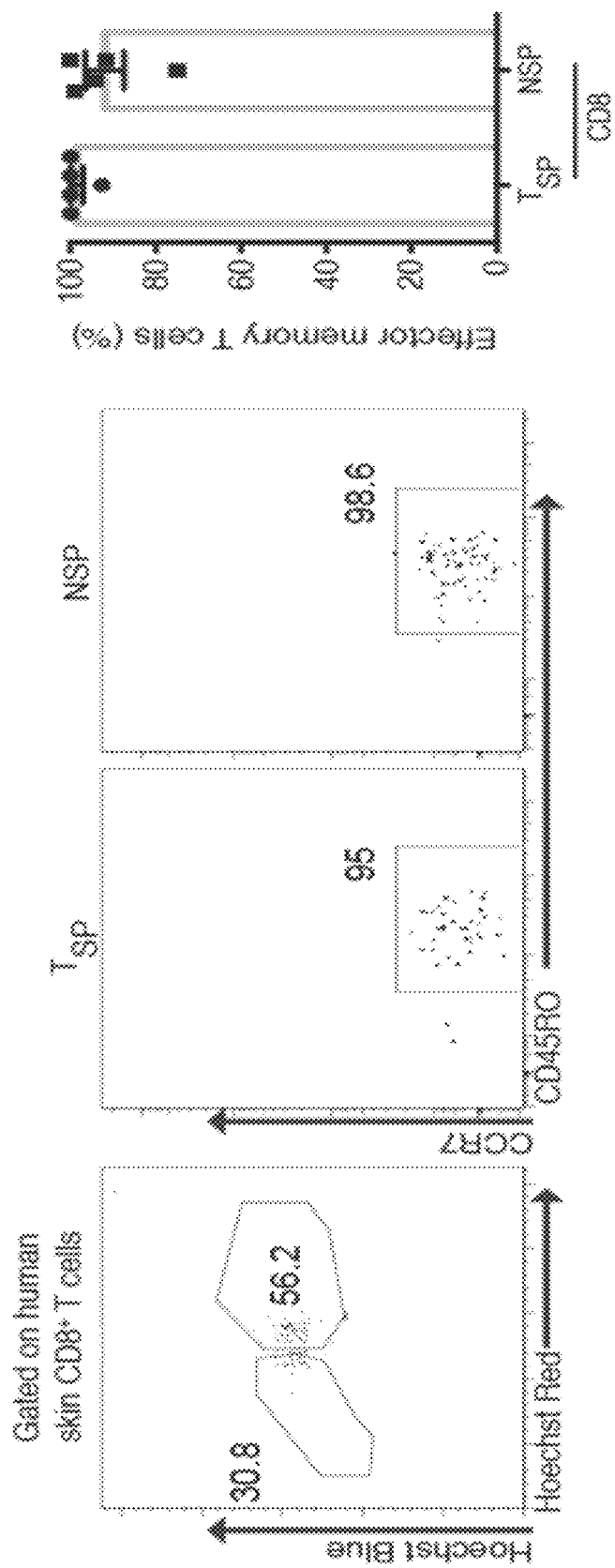
Figure 8D:
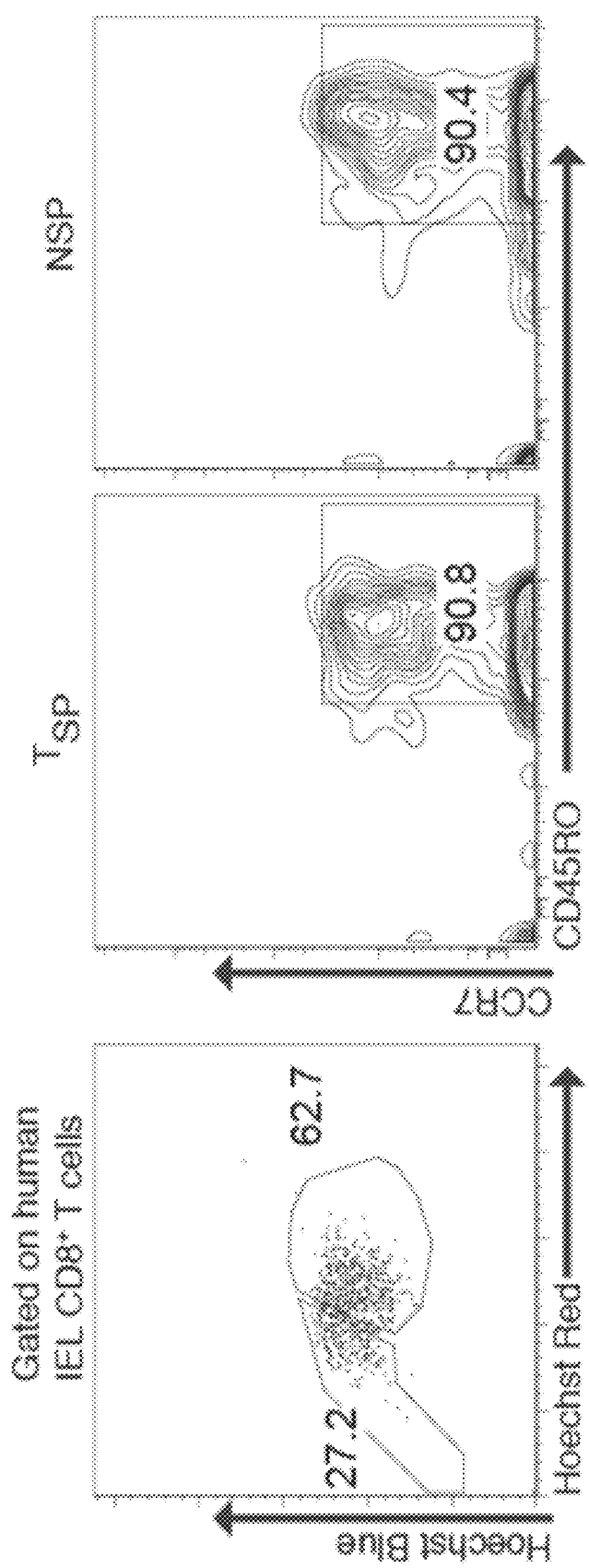

The finding that human T$_{SP}$ cells were capable of greater engraftment and tissue infiltration in vivo supported the hypothesis that these may be attractive vehicles to improve adoptive T cell therapy. However a potential obstacle with clinical application of such a strategy is that most human T$_{SP}$ cells are restricted to tissues, including the bone marrow. Human hematopoietic stem cells (HSCs) with SP phenotype and long-term repopulation potential can be mobilized from the bone marrow with CXCR4 antagonist, plerixafor. Therefore, whether this strategy can also lead to concurrent mobilization of human T$_{SP}$ cells in vivo was examined. Injection of plerixafor led to a marked increase in circulating CD8$^+$ T$_{SP}$ cells within 24 hours, concurrent with mobilization of CD34$^+$ SP$^+$ HSCs. Together, these studies demonstrate that mobilization of human CD8$^+$ T$_{SP}$ cells is possible using routine methodology and as such, can permit their potential application as a novel platform for adoptive T cell therapy in humans (FIGS. 7D-7E).

Figure 14A:
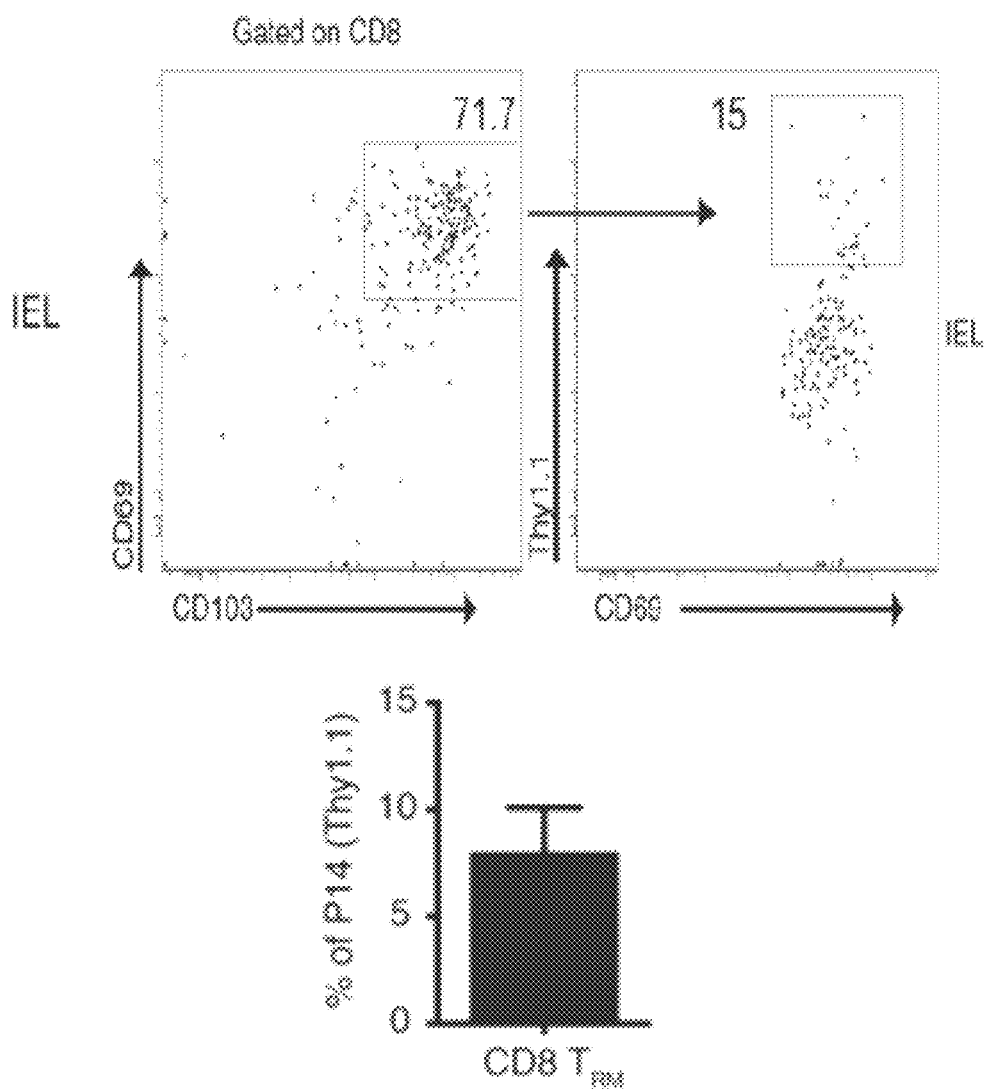
FIGS. 14A-14B are a series of graphs showing the generation of gut tissue resident memory ($T_{RM}$) cells by adoptive transfer of SP CD8 T cells.
Figure 14B:
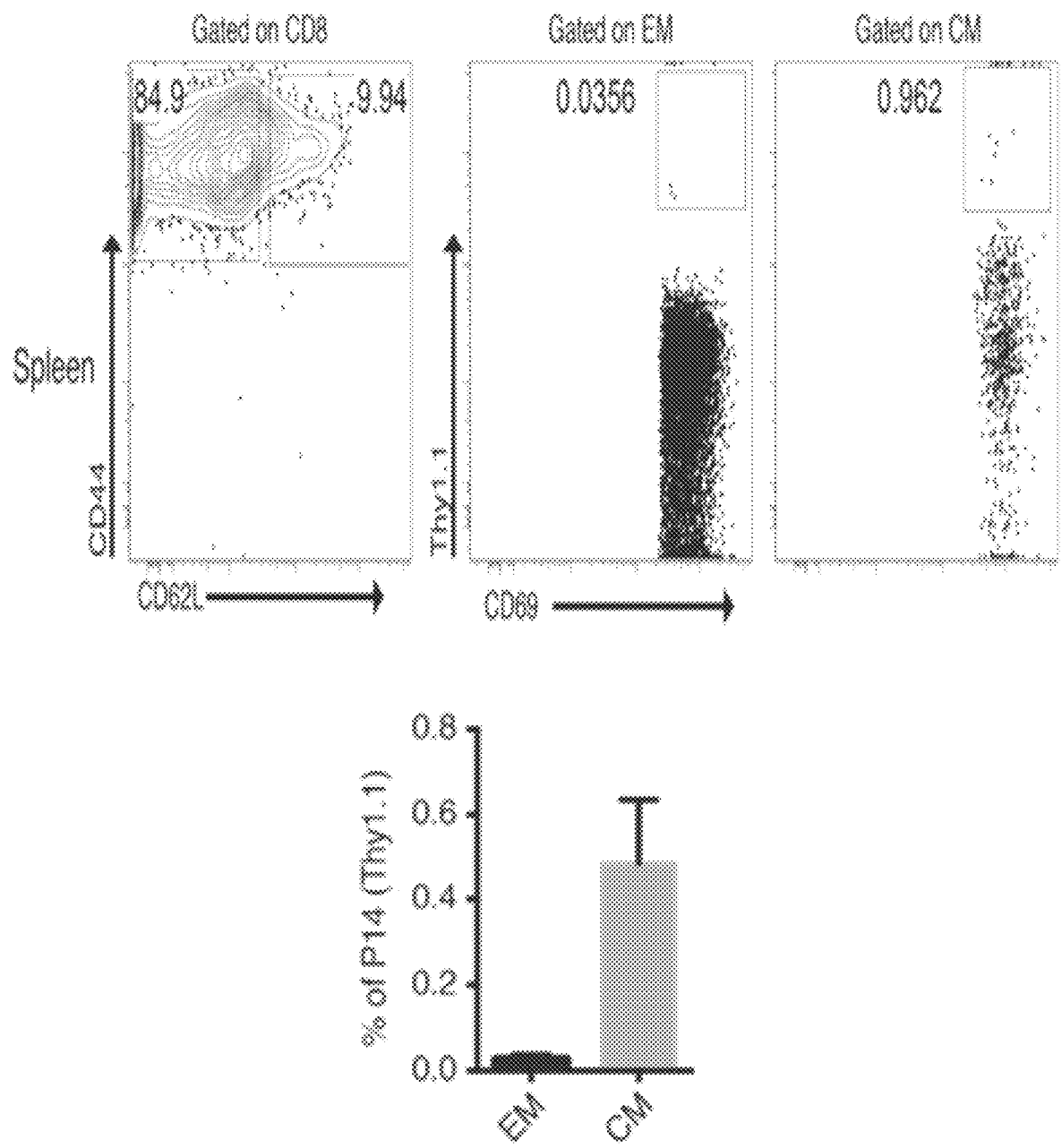

In order to further evaluate whether CD8 T$_{SP}$ cells could differentiate into T$_{RM}$ cells, murine T$_{SP}$ cells from P14 (Thy 1.1$^+$) chimeras were adoptively transferred into RAG$^{-/-}$ mice. Adoptively transferred LCMV-specific P14 (Thy1.1$^+$) T$_{SP}$ CD8+ T cells were able to generate CD8 T$_{RMs}$ in the gut, while the generation of TCM cells in the spleen was very low (FIGS. 14A-14B). Therefore these data indicate that T$_{SP}$ cells are able to generate T$_{RM}$ cells in vivo. The capacity to generate T$_{RM}$ cells may be particularly important for the application of adoptive T cell therapy as a tool to boost immunity in NLTs, such as in the setting of solid tumors.

As shown herein, a distinct subset of human/murine slow-cycling T cells were identified that efflux Hoechst dyes, and are enriched within a population of T cells that display canonical T$_{RM}$ properties. T cells with the SP phenotype (T$_{SP}$ cells) were enriched in tissues such as gut and skin known to be enriched in T$_{RM}$ cells, but were also enriched in the human bone marrow and could even be detected in human blood. Interestingly, even circulating human T$_{SP}$ cells express core genomic signatures of human T$_{RM}$ cells within tissues. The precise relationship between circulating T$_{SP}$ cells and classic tissue based T$_{RM}$ cells is currently unknown.

A unifying property of human/murine T$_{SP}$ cells in all tissues (as well as those in human blood) was their enrichment in the G0 phase of the cell cycle, indicating a quiescent/slow cycling phenotype. In adult stem cells, quiescence is intricately linked to long-term persistence and repopulating ability (Nakamura-Ishizu et al. Development. 2014; 141(24):4656-66). Without wishing to be bound by specific theory, it is possible that similar biology exists between adult stem cells and T cells; and the presence of slow-cycling T cells is essential for long-term maintenance of nave and memory T cell repertoires. Recent studies analyzing human T$_{RM}$ cells suggest that these cells may be stably maintained over decades of life with only minimal turnover and homeostatic proliferation relative to T$_{CM}$ cells in lymphoid tissues, although prospective studies of human tissues are lacking to date (Thome et al. Cell. 2014; 159(4):814-28). Therefore, the finding described herein that nearly all of the T$_{RM}$ cells with the T$_{SP}$ phenotype were in the G0 state provides evidence that the T$_{SP}$ subset reflects the quiescent compartment in T$_{RM}$ cells. It is notable that this is in contrast to most memory T cells in lymphoid tissues that are typically in G1, which permits homeostatic turnover (Allam et al., Blood. 2009; 114(10):2121-30; Veiga-Fernandes and Rocha, Nat Immunol. 2004; 5(1):31-7). Diminished homeostatic cycling of T$_{SP}$ cells was also confirmed herein based on the label-retaining fraction of T$_{RM}$ cells in histone 2B GFP mice. Label retention in these mice has also been utilized to identify quiescent compartments in other tissues (Foudi et al., Nat Biotechnol. 2009; 27(1):84-90). It is notable that gut T$_{RM}$ cells seem to have greater proportion of label retaining cells than memory T cells in lymphoid tissues. These studies therefore suggest that turnover in the T$_{RM}$ compartment may be lower than in T$_{CM}$ cells. Furthermore, there is heterogeneity relating to the cell cycle even within T$_{RM}$ cells and the T$_{SP}$ phenotype specifically marks the label retaining subset of CD8 T$_{RM}$ cells within tissues.

Two gene families enriched in the T$_{SP}$ core gene expression signature were ATP binding cassette (ABC) transporters and NR4A family of transcription factors. ABC transporters are directly responsible for the SP phenotype, and postulated to help protect stem cells from oxidative and genotoxic stress, although the nature of specific substrates may depend on the specific tissue (Tarling et al., Trends in endocrinology and metabolism: TEM. 2013; 24(7):342-50). It is likely that these transporters play a similar role in the context of T cells as well. Without wishing to be bound by specific theory, this may be particularly true in the setting of T$_{RM}$ cells at barrier sites such as the gut, where they may be needed to actively efflux substrates to keep gut T$_{RM}$ cells in quiescent state. Indeed, gut T$_{RM}$ cells from transporter deficient mice had an inflammatory phenotype. Notably, increased IFNγ production by gut T cells in these mice was restricted to only T$_{RM}$ cells, but not non-T$_{RM}$ cells, consistent with a T$_{RM}$-specific impact of transporter deficiency.

In addition to ABC transporters, the core gene expression signature of T$_{SP}$ cells was also enriched for the NR4A family of transcription factors. These nuclear receptors act as transcription factors to induce or repress gene expression. NR4A1 is activated as a part of early response, related in part to the strength of TCR signaling and implicated in regulating T cell differentiation. Recently, NR4A1 was shown to regulate expansion and effector function of murine CD8 effector T cells through direct repression of IRF4. The present study demonstrates a novel role for this factor in the biology of murine T$_{RM}$ cells. T cells from Nur77$^{-/-}$ mice demonstrated reduced capacity to generate T$_{RM}$ cells, indicating that this transcription factor may be important in regulating the generation/tissue residence of T$_{RM}$ cells. This dependence on NR4A1 is reminiscent of the situation in patrolling monocytes, which express all three NR4A genes, but depend only on NR4A1.

Findings described herein that human/murine T cells represent a quiescent T cell subpopulation, with a potential to be enriched in tissues over long term in vivo and can be mobilized into circulation in humans demonstrates that these cells provide a novel platform for immunotherapy, particularly for tumors in non-lymphoid tissues and bone marrow.

Other Embodiments

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

The disclosures of each and every patent, patent application, and publication cited herein are hereby incorporated herein by reference in their entirety. While this disclosure has been disclosed with reference to specific embodiments, it is apparent that other embodiments and variations of this disclosure may be devised by others skilled in the art without departing from the true spirit and scope of the disclosure. The appended claims are intended to be construed to include all such embodiments and equivalent variations.

What is claimed:

1. A method of obtaining a $T_{sp}$ cell from a subject, the method comprising:
    administering to the subject a CXCR4 antagonist, wherein the CXCR4 antagonist induces mobilization of the $T_{sp}$ cell from the subject's tissue or bone marrow into the subject's circulation, and
    isolating the $T_{sp}$ cell so mobilized from the subject's circulation.

2. The method of claim 1, wherein the CXCR4 antagonist comprises plerixafor.

3. The method of claim 1, further comprising administering granulocyte-colony stimulating factor (G-CSF) to the subject.

4. The method of claim 1, further comprising expanding the isolated $T_{sp}$ cell ex vivo.

5. A method of adoptive T cell transfer in a subject, the method comprising:
    administering to the subject a CXCR4 antagonist, wherein the CXCR4 antagonist induces mobilization of the $T_{sp}$ cell from the subject's tissue or bone marrow into the subject's circulation,
    isolating the $T_{sp}$ cell so mobilized from the subject's circulation,
    modifying the isolated $T_{sp}$ cell ex vivo, and
    administering the modified $T_{sp}$ cell to the subject.

6. The method of claim 5, wherein the CXCR4 antagonist comprises plerixafor.

7. The method of claim 5, further comprising administering granulocyte-colony stimulating factor (G-CSF) to the subject.

8. A method of adoptive T cell transfer in a subject, the method comprising:
    isolating a $T_{sp}$ cell from a subject, wherein the $T_{sp}$ cell displays a quiescent (GO) phenotype, and expresses at least one ABC transporter and at least one transcription factor from the NR4A family,
    modifying the isolated $T_{sp}$ cell ex vivo, and
    administering the modified $T_{sp}$ cell to the subject.

9. The method of claim 8, wherein the $T_{SP}$ cell is isolated from the subject's gut, liver, skin or bone marrow.

* * * * *